US012652729B2

(12) United States Patent
Nysen et al.

(10) Patent No.: US 12,652,729 B2
(45) Date of Patent: Jun. 9, 2026

(54) SYSTEM, METHOD, AND COMPUTER PROGRAM PRODUCT FOR DETERMINING A CHARACTERISTIC OF AN INDUCTION HEATING CIRCUIT

(71) Applicant: Philip Morris Products, S.A., Neuchåel (CH)

(72) Inventors: Peter Nysen, Morgan Hill, CA (US); Andrew L. Bleloch, Kenmore, WA (US)

(73) Assignee: Philip Morris Products S.A., Neuchatel (CH)

( * ) Notice: Subject to any disclaimer, the term of this patent is extended or adjusted under 35 U.S.C. 154(b) by 1039 days.

(21) Appl. No.: 17/780,447

(22) PCT Filed: Nov. 27, 2020

(86) PCT No.: PCT/US2020/062476
§ 371 (c)(1),
(2) Date: May 26, 2022

(87) PCT Pub. No.: WO2021/108749
PCT Pub. Date: Jun. 3, 2021

(65) Prior Publication Data
US 2023/0078194 A1 Mar. 16, 2023

Related U.S. Application Data

(60) Provisional application No. 62/940,987, filed on Nov. 27, 2019.

(51) Int. Cl.
*H05B 6/06* (2006.01)
*A24F 40/465* (2020.01)
(Continued)

(52) U.S. Cl.
CPC ............. *H05B 6/08* (2013.01); *A24F 40/465* (2020.01); *A24F 40/51* (2020.01); *A24F 40/57* (2020.01);
(Continued)

(58) Field of Classification Search
CPC .. H05B 6/08; H05B 6/105; H05B 6/06; A24F 40/465; A24F 40/51; A24F 40/57;
(Continued)

(56) References Cited

U.S. PATENT DOCUMENTS

| | | | |
|---|---|---|---|
| 4,025,912 A | 5/1977 | Rice | |
| 2007/0087465 A1 | 4/2007 | Stahl et al. | |

(Continued)

FOREIGN PATENT DOCUMENTS

| | | |
|---|---|---|
| EP | 2842724 A1 | 3/2015 |
| EP | 2330866 A2 | 11/2016 |

(Continued)

*Primary Examiner* — Tiffany T Tran
(74) *Attorney, Agent, or Firm* — Oblon, McClelland, Maier & Neustadt, L.L.P.

(57) ABSTRACT

Provided are systems that includes an a induction heating circuit and at least one processor programmed or configured to generate each line of a plurality of lines, where each line comprises a graphical representation of phase value versus frequency of a signal with which the induction heating circuit is driven, determine a line of the plurality of lines that has a maximum slope, determine an average frequency of the line having the maximum slope, determine a phase value corresponding to the average frequency of the line having the maximum slope, determine a time delay, determine a self-resonant frequency (SRF) value of the induction heating circuit based on the time delay, and determine a characteristic of the induction heating circuit based on the resonant frequency value. Methods and computer program products are also disclosed.

20 Claims, 19 Drawing Sheets

(51) Int. Cl.

| | |
|---|---|
| *A24F 40/51* | (2020.01) |
| *A24F 40/57* | (2020.01) |
| *A61M 11/04* | (2006.01) |
| *A61M 15/06* | (2006.01) |
| *G01K 7/36* | (2006.01) |
| *G01R 27/26* | (2006.01) |
| *H05B 6/08* | (2006.01) |
| *H05B 6/10* | (2006.01) |

(52) U.S. Cl.
CPC .......... *A61M 11/042* (2014.02); *A61M 15/06* (2013.01); *G01K 7/36* (2013.01); *G01R 27/2611* (2013.01); *H05B 6/105* (2013.01); *A61M 2205/3368* (2013.01)

(58) Field of Classification Search
CPC ................ A61M 11/042; A61M 15/06; A61M 2205/3368; G01K 7/36; G01R 27/2611
See application file for complete search history.

(56) References Cited

U.S. PATENT DOCUMENTS

| | | | |
|---|---|---|---|
| 2016/0234886 A1 | 8/2016 | Laghi et al. | |
| 2017/0055583 A1 | 3/2017 | Blandino et al. | |
| 2018/0297832 A1 | 10/2018 | Fabbri | |
| 2018/0329015 A1 | 11/2018 | Loussert et al. | |
| 2019/0289678 A1* | 9/2019 | Nam ................... | H05B 6/1209 |
| 2020/0022412 A1* | 1/2020 | Abi Aoun ................ | G01K 7/16 |
| 2020/0037402 A1* | 1/2020 | Abi Aoun .............. | H05B 6/105 |
| 2021/0338856 A1* | 11/2021 | Fritchie ................... | A61L 2/04 |

FOREIGN PATENT DOCUMENTS

| | | | |
|---|---|---|---|
| EP | 3355662 A1 | 8/2018 | |
| JP | 2002195890 A | 7/2002 | |
| JP | 2004144683 A | 5/2004 | |
| JP | 2016524777 A | 8/2016 | |
| WO | 2016065574 A1 | 5/2016 | |
| WO | 2018178113 A2 | 10/2018 | |
| WO | 2018178114 A2 | 10/2018 | |

* cited by examiner

200

202

Processor
204

Memory
206

Storage component
208

Input component
210

Output component
212

Communication
interface
214

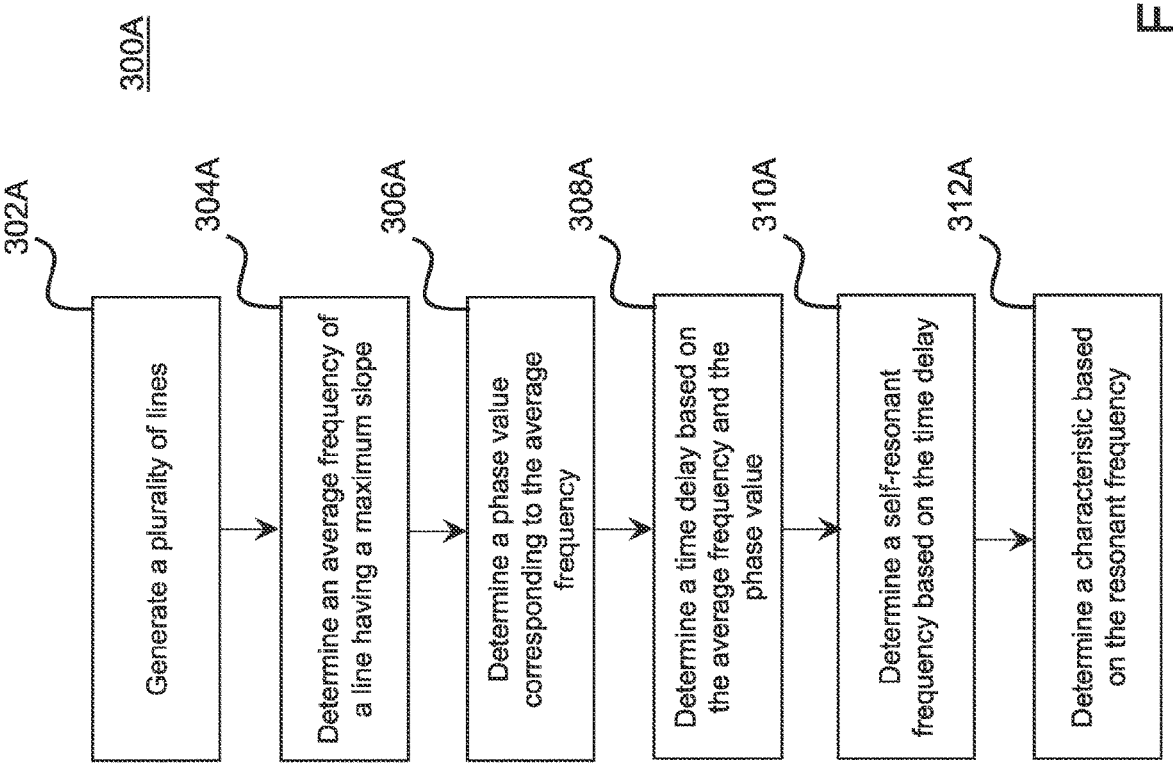

300A

302A — Generate a plurality of lines

304A — Determine an average frequency of a line having a maximum slope

306A — Determine a phase value corresponding to the average frequency

308A — Determine a time delay based on the average frequency and the phase value 310A — Determine a self-resonant frequency based on the time delay 312A — Determine a characteristic based on the resonant frequency

302B — Cause a susceptor element to generate heat

304B — Determine a response of an induction heating circuit

306B — Determine a characteristic of the susceptor element

300C

302C
Determine a response phase of an induction heating circuit

304C
Determine a function of phase versus frequency for the induction heating circuit 306C
Determine a frequency value where a phase value of the function is in quadrature 308C
Determine a temperature of a susceptor element Calibration of SRF delta with respect to a thermocouple temperature sensor

SYSTEM, METHOD, AND COMPUTER PROGRAM PRODUCT FOR DETERMINING A CHARACTERISTIC OF AN INDUCTION HEATING CIRCUIT

CROSS-REFERENCE TO RELATED APPLICATIONS

This application is the United States national phase of International Patent Application No. PCT/US2020/062476 filed Nov. 27, 2020, and claims priority to U.S. Provisional Application No. 62/940,987 filed Nov. 27, 2019, the disclosures of which are hereby incorporated by reference in their entirety.

BACKGROUND

Induction heating includes heating an object that is electrically conductive (e.g., a metal object) by electromagnetic induction. For example, induction heating includes heating the object based on heat generated in the object by eddy currents that flow in the object. In some instances, an induction heating system includes an induction heater and an electrically conductive object to be heated based on electromagnetic induction. The induction heater includes an electromagnet and an electronic oscillator that passes an alternating electrical current (AC) through the electromagnet so that the electromagnet produces a magnetic field (e.g., an H field). In some cases, the magnetic field is directed at the electrically conductive object and penetrates the electrically conductive object. Electric currents may be generated inside the electrically conductive object based on the magnetic field. The electric currents are sometimes referred to as eddy currents. The eddy currents may flow through the electrically conductive object and cause heat to be generated in the electrically conductive object based on Joule heating. In some instances, the electrically conductive object includes a ferromagnetic material (e.g., iron) and heat is generated in the electrically conductive object based on magnetic hysteresis (e.g., magnetic hysteresis losses).

In some instances, the electrically conductive object includes a susceptor. The susceptor includes a material that has the ability to absorb electromagnetic energy and convert the electromagnetic energy to heat. In addition, the susceptor may be configured to emit the heat as radiation (e.g., infrared thermal radiation). The electromagnetic energy includes radiation (e.g., electromagnetic radiation) in the radio frequency spectrum or microwave spectrum.

BRIEF DESCRIPTION OF THE DRAWINGS

Additional advantages and details of the disclosure are explained in greater detail below with reference to the exemplary embodiments that are illustrated in the accompanying schematic figures, in which:

FIG. 3A is a flowchart of a non-limiting embodiment of a method of determining a characteristic of an induction heating system;

DETAILED DESCRIPTION

Figure 1:
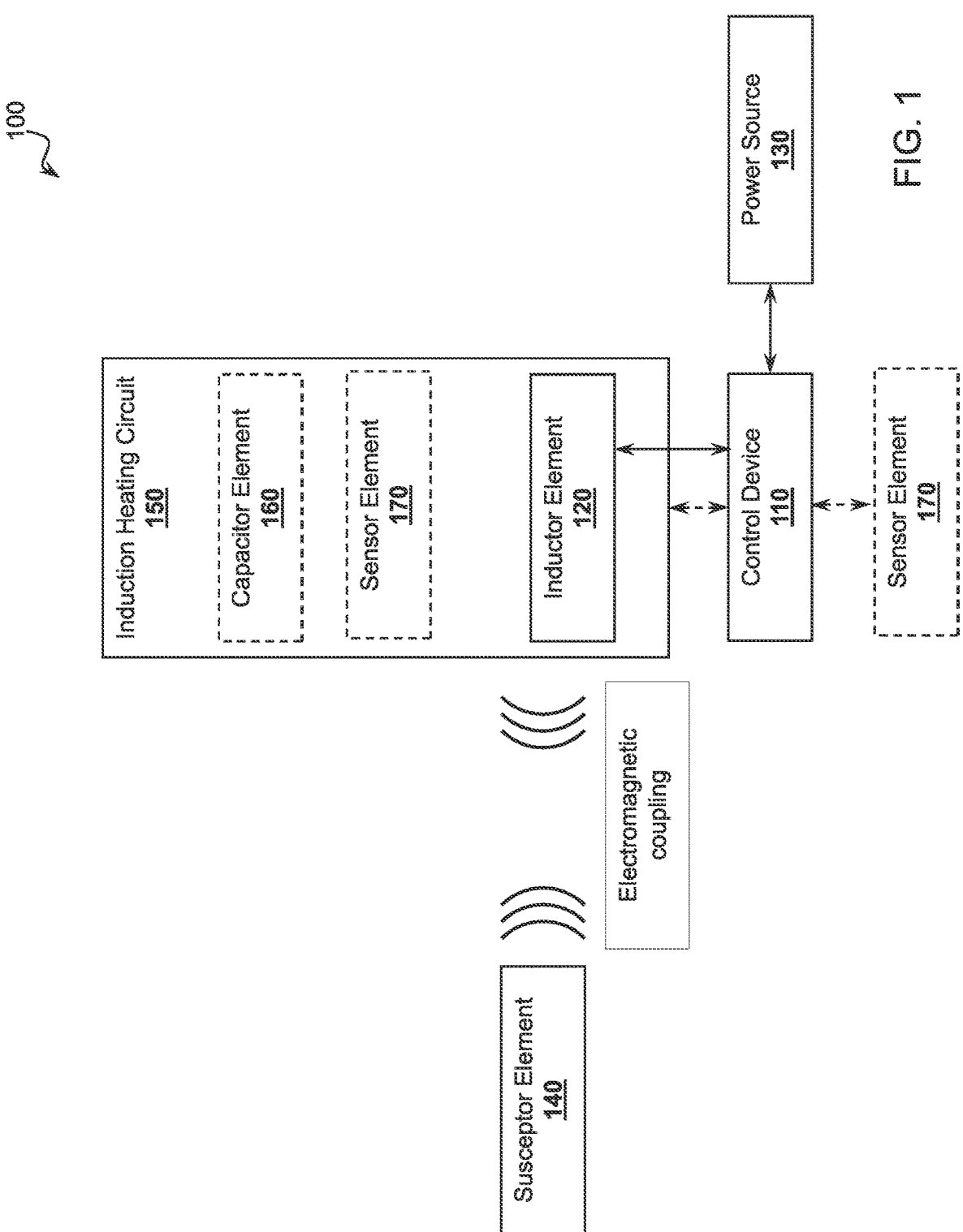
FIG. 1 is a diagram of a non-limiting embodiment of a system with which systems, methods, and/or products described herein, may be implemented according to the principles of the present disclosure.

The present disclosure relates generally to systems, methods, and products used for determining a characteristic of an induction heating circuit. Accordingly, various embodiments are disclosed herein of devices, systems, computer program products, apparatus, and/or methods for determining a characteristic of an induction heating circuit.

Clause 1: An induction heating system comprising: an induction heating circuit; and at least one processor programmed or configured to: generate each line of a plurality of lines, wherein each line comprises a graphical representation of phase value versus frequency of a signal with which the induction heating circuit is driven; determine a line of the plurality of lines that has a maximum slope; determine an average frequency of the line having the maximum slope; determine a phase value corresponding to the average frequency of the line having the maximum slope; determine a time delay, wherein the time delay is equal to a difference of the phase value corresponding the maximum slope and an assumed phase value at quadrature divided by a product of a full period of phase and the average frequency of the line having the maximum slope; determine a self-resonant frequency (SRF) value of the induction heating circuit based on the time delay; and determine a characteristic of the induction heating circuit based on the SRF value.

Clause 2: The induction heating system of clause 1, wherein when determining the SRF value of the induction heating circuit, the at least one processor is programmed or configured to: measure a preliminary first phase of a first AC voltage across an electrical component of the induction heating circuit based on a first driving AC voltage at a first driving frequency; adjust the preliminary first phase using the time delay to provide a corrected preliminary first phase; determine a first response phase of the induction heating circuit at the first driving frequency based on the corrected preliminary first phase, and wherein the first response phase is a value of phase difference between a phase value of a driving current at the first driving frequency and a phase value of the first AC voltage across the electrical component of the induction heating circuit at the first driving frequency; measure a preliminary second phase of a second AC voltage across the electrical component of the induction heating circuit based on a second driving AC voltage at a second driving frequency; adjust the preliminary second phase using the time delay to provide a corrected preliminary second phase; determine a second response phase of the induction heating circuit at the second driving frequency based on the corrected preliminary second phase, and wherein the second response phase is a value of phase difference between a phase value of a driving current at the second driving frequency and a phase value of the second AC voltage across the electrical component of the induction heating circuit at the second driving frequency; determine a function of phase versus frequency for the induction heating circuit based on the first response phase and the second response phase; and determine the SRF value where a phase value of the function of phase versus frequency is in quadrature.

Clause 3: The system of clauses 1 or 2, wherein when generating each line of the plurality of lines, the at least one processor is programmed or configured to: determine a first phase value of a first AC voltage across an electrical component of the induction heating circuit, wherein when determining the first phase of the first AC voltage across the electrical component of the induction heating circuit, the at least one programmed or configured to: drive the induction heating circuit with a first driving AC voltage at a first driving frequency; measure the first phase value of the first AC voltage across the electrical component of the induction heating circuit based on the first driving AC voltage at the first driving frequency; determine a second phase value of a second AC voltage across the electrical component of the induction heating circuit, wherein when determining the second phase value of the second AC voltage across the electrical component of the induction heating circuit, the at least one programmed or configured to: drive the induction heating circuit with a second driving AC voltage at a second driving frequency; measure the second phase value of the second AC voltage across the electrical component of the induction heating circuit based on the second driving AC voltage at the second driving frequency; generate a line of phase versus frequency based on the first phase value at the first driving frequency and the second phase value at the second driving frequency.

Clause 4: The system of any of clauses 1-3, wherein when determining the line of the plurality of lines that has the maximum slope, the at least one processor is programmed or configured to: determine a slope of each line of the plurality of lines, wherein when determining the slope of each line of the plurality of lines, the at least one processor is programmed or configured to: determine the slope of the line based on a difference of the first phase value and the second phase value divided by a difference of the first driving frequency and the second driving frequency; compare the slope of each line of the plurality of lines to a slope of all other lines of the plurality of lines to provide the line having the maximum slope.

Clause 5: The system of any of clauses 1-4, where the at least one processor is further programmed or configured to: determine the first phase value of the voltage across the electrical component of the induction heating circuit at the first driving frequency based on a first measurement of voltage across a capacitor element of the induction heating circuit; and determine the second phase value of the voltage across the electrical component of the induction heating circuit at the second driving frequency based on a second measurement of voltage across the capacitor element.

Clause 6: The system of any of clauses 1-5 wherein the induction heating circuit comprises: an inductor element; and a capacitor element.

Clause 7: The system of any of clauses 1-6 wherein the induction heating circuit comprises an electrical component and wherein the electrical component of the induction heating circuit comprises: an inductor element, a capacitor element, or a component of the induction heating circuit that provides a phase that is the same as the phase of a voltage across the inductor element or the capacitor element.

Clause 8: The system of any of clauses 1-7, wherein the at least one processor is further programmed or configured to: measure a preliminary third phase of a third AC voltage across the electrical component of the induction heating circuit based on a fourth driving AC voltage at a third driving frequency; adjust the preliminary third phase using the time delay to provide a corrected preliminary third phase; determine a third response phase of the induction heating circuit at the third driving frequency based on the corrected preliminary third phase, and wherein the third response phase is a value of phase difference between a phase of a driving current at the third driving frequency and a phase of a voltage across the electrical component of the induction heating circuit at the third driving frequency; measure a preliminary fourth phase of a fourth AC voltage across the electrical component of the induction heating circuit based on a fourth driving AC voltage at a fourth driving frequency; adjust the preliminary fourth phase using the time delay to provide a corrected preliminary fourth phase; determine a fourth response phase of the induction heating circuit, and wherein the fourth response phase is a value of phase difference between a phase of a driving current at the fourth driving frequency and a phase of a voltage across the electrical component of the induction heating circuit at the fourth driving frequency; and wherein, when determining the function of phase versus frequency for the induction heating circuit, the at least one processor is programmed or configured to: determine the function of phase versus frequency for the induction heating circuit based on the first response phase, the second response phase, the third response phase, and the fourth response phase.

Clause 9: The system of any of clauses 1-8, wherein the function of phase versus frequency comprises a polynomial, and wherein, when determining the function of phase versus frequency, the at least one processor is programmed or configured to: determine polynomial coefficients of the polynomial that is fit to the first response phase of the induction heating circuit, the second response phase of the induction heating circuit, the third response phase of the induction heating circuit, and the fourth response phase of the induction heating circuit, and wherein, when determining the frequency value where the response phase value of the function is in quadrature, the at least one processor is programmed or configured to: determine a frequency value where the phase value of the function of phase versus frequency is in quadrature based on the polynomial coefficients of the polynomial.

Clause 10: The system of any of clauses 1-9, wherein, when determining the function of phase versus frequency based on the first response phase and the second response phase, the at least one processor is programmed or configured to: determine polynomial coefficients of a polynomial that is fit to the first response phase of the induction heating circuit and the second response phase of the induction heating circuit, and wherein, when determining the frequency value where the response phase value of the function is in quadrature, the at least one processor is programmed or configured to: determine the frequency value where the phase value of the function of phase versus frequency is in quadrature based on the polynomial coefficients of the polynomial.

Clause 11: The system of any of clauses 1-10, wherein the at least one processor is further programmed or configured to: determine a temperature of a susceptor element.

Clause 12: The system of any of clauses 1-11, wherein, when determining the temperature of the susceptor element, the at least one processor is programmed or configured to: determine the temperature of the susceptor element based on a measurement of a magnetic field generated by the inductor element and a frequency value where the phase value of the function of phase versus frequency is in quadrature.

Clause 13: The system of any of clauses 1-12, wherein the at least one processor is further programmed or configured to: determine a measurement of a magnetic field generated by the inductor element, wherein, when determining the temperature of the susceptor element, the at least one processor is programmed or configured to: determine the temperature of the susceptor element based on the measurement of the magnetic field generated by the inductor element and the frequency value where the phase value of the function of phase versus frequency is in quadrature.

Clause 14: The system of any of clauses 1-13, wherein, when determining the temperature of the susceptor element, the at least one processor is programmed or configured to: determine a measurement of a magnetic field generated by the inductor element based on a measurement of: an amplitude of an A/C voltage across the capacitor element, and a frequency of the A/C voltage across the capacitor element; and wherein, when determining the temperature of the susceptor element, the at least one processor is programmed or configured to: determine the temperature of the susceptor element based on the measurement of the magnetic field generated by the inductor element and the frequency value where the phase value of the function is in quadrature.

Clause 15: The system of any of clauses 1-14, wherein, when determining the temperature of the susceptor element, the at least one processor is programmed or configured to: determine an amplitude of an A/C voltage across the capacitor element and a frequency of the A/C voltage across the capacitor element; determine a measurement of a magnetic field generated by the inductor element based on the amplitude of an A/C voltage across the capacitor element and the frequency of the A/C voltage across the capacitor element; and determine the temperature of the susceptor element based on the measurement of the magnetic field generated by the inductor element and the frequency value where the phase value of the function is in quadrature.

Clause 16: The system of any of clauses 1-15, further comprising: at least one temperature sensor; and wherein, when determining the temperature of the susceptor element, the at least one processor is programmed or configured to: determine the temperature of the susceptor element based on a frequency value where the phase value of the function of phase versus frequency is in quadrature and an output of the at least one temperature sensor.

Clause 17: The system of any of clauses 1-16, further comprising: at least one temperature sensor in thermal contact with at least one of: the inductor element, the capacitor element, or any combination thereof; and wherein, when determining the temperature of the susceptor element, the at least one processor is programmed or configured to: determine the temperature of the susceptor element based on the frequency value where the phase value of the function is in quadrature and an output of the at least one temperature sensor.

Clause 18: The system of any of clauses 1-17, wherein the at least one processor is further programmed or configured to: determine a temperature of a susceptor element; wherein, when determining the temperature of the susceptor element, the at least one processor is programmed or configured to: determine the temperature of the susceptor element based on the frequency value where the phase value of the function is in quadrature and a temperature of an inductor element, a capacitor element, or any combination thereof.

Clause 19: The system of any of clauses 1-18, wherein the at least one processor is further programmed or configured to: determine a temperature of a susceptor element; wherein, when determining the temperature of the susceptor element, the at least one processor is programmed or configured to: determine the temperature of the susceptor element based on an amount of power absorbed by the susceptor element.

Clause 20: The system of any of clauses 1-19, wherein the at least one processor is further programmed or configured to: control the temperature of the susceptor element.

Clause 21: The system of any of clauses 1-20, wherein, when controlling the temperature of the susceptor element, the at least one processor is programmed or configured to: control a rate at which the temperature of the susceptor element changes based on an amount of power absorbed by the susceptor element.

Clause 22: The system of any of clauses 1-21, wherein the at least one processor is further programmed or configured to: determine whether a susceptor element is in proximity to an inductor element based on an amount of power absorbed by the susceptor element.

Clause 23: The system of any of clauses 1-22, wherein the at least one processor is further programmed or configured to: determine an amount of power absorbed by a susceptor element based on the function of phase versus frequency; and wherein, when determining the temperature of the susceptor element, the at least one processor is programmed or configured to: determine the temperature of the susceptor element based on the amount of power absorbed by the susceptor element.

Clause 24: The system of any of clauses 1-23, wherein the at least one processor is further programmed or configured to: provide an amount of electrical current to the inductor element based on a time average value of electrical current to be provided to the inductor element to maintain a specified temperature of the susceptor element.

Clause 25: The system of any of clauses 1-24, wherein, when determining the temperature of the susceptor element, the at least one processor is programmed or configured to: determine the temperature of the susceptor element based on a result of at least one calibration process.

Clause 26: The system of any of clauses 1-25, wherein the result of the at least one calibration process comprises: a reference set of a plurality of values of temperature of the susceptor element and a plurality of frequency values for each of a plurality of phase values of the function that are in quadrature, wherein each of the plurality of frequency values corresponds to each of the plurality of values of temperature of the susceptor element; wherein, when determining the temperature of the susceptor element, the at least one processor is programmed or configured to: compare the frequency value where the phase value of the function is in quadrature to the reference set; and determine the temperature of the susceptor element based on a value of temperature in the reference set that corresponds to the frequency value where the phase value of the function is in quadrature.

Clause 27: A method comprising: generating, with at least one processor, each line of a plurality of lines, wherein each line comprises a graphical representation of phase value versus frequency of a signal with which the induction heating circuit is driven; determining, with at least one processor, a line of the plurality of lines that has a maximum slope; determining, with at least one processor, an average frequency of the line having the maximum slope; determining, with at least one processor, a phase value corresponding to the average frequency of the line having the maximum slope; determining, with at least one processor, a time delay, wherein the time delay is equal to a difference of the phase value corresponding the maximum slope and an assumed phase value at quadrature divided by a product of a full period of phase and the average frequency of the line having the maximum slope; determining, with at least one processor, a self-resonant frequency (SRF) value of the induction heating circuit based on the time delay; and determining, with at least one processor, a characteristic of the induction heating circuit based on the SRF value.

Clause 28: The method of clause 27, wherein determining the SRF value of the induction heating circuit comprises: measuring a preliminary first phase of a first AC voltage across an electrical component of the induction heating circuit based on a first driving AC voltage at a first driving frequency; adjusting the preliminary first phase using the time delay to provide a corrected preliminary first phase; determining a first response phase of the induction heating circuit at the first driving frequency based on the corrected preliminary first phase, and wherein the first response phase is a value of phase difference between a phase value of a driving current at the first driving frequency and a phase value of the first AC voltage across the electrical component of the induction heating circuit at the first driving frequency; measuring a preliminary second phase of a second AC voltage across the electrical component of the induction heating circuit based on a second driving AC voltage at a second driving frequency; adjusting the preliminary second phase using the time delay to provide a corrected preliminary second phase; determining a second response phase of the induction heating circuit at the second driving frequency based on the corrected preliminary second phase, and wherein the second response phase is a value of phase difference between a phase value of a driving current at the second driving frequency and a phase value of the second AC voltage across the electrical component of the induction heating circuit at the second driving frequency; determining a function of phase versus frequency for the induction heating circuit based on the first response phase and the second response phase; and determining the SRF value where a phase value of the function of phase versus frequency is in quadrature.

Clause 29: The method of clauses 27 or 28, wherein generating each line of the plurality of lines comprises: determining a first phase value of a first AC voltage across an electrical component of the induction heating circuit, wherein determining the first phase of the first AC voltage across the electrical component of the induction heating circuit comprises: driving the induction heating circuit with a first driving AC voltage at a first driving frequency; measuring the first phase value of the first AC voltage across the electrical component of the induction heating circuit based on the first driving AC voltage at the first driving frequency; determining a second phase value of a second AC voltage across the electrical component of the induction heating circuit, wherein when determining the second phase value of the second AC voltage across the electrical component of the induction heating circuit, the at least one programmed or configured to: driving the induction heating circuit with a second driving AC voltage at a second driving frequency; measuring the second phase value of the second AC voltage across the electrical component of the induction heating circuit based on the second driving AC voltage at the second driving frequency; generating a line of phase versus frequency based on the first phase value at the first driving frequency and the second phase value at the second driving frequency.

Clause 30: The method of any of clauses 27-29, wherein determining the line of the plurality of lines that has the maximum slope comprises: determining a slope of each line of the plurality of lines, wherein determining the slope of each line of the plurality of lines comprises: determining the slope of the line based on a difference of the first phase value and the second phase value divided by a difference of the first driving frequency and the second driving frequency; comparing the slope of each line of the plurality of lines to a slope of all other lines of the plurality of lines to provide the line having the maximum slope.

Clause 31: The method of any of clauses 27-30, further comprising: determining the first phase value of the voltage across the electrical component of the induction heating circuit at the first driving frequency based on a first measurement of voltage across a capacitor element of the induction heating circuit; and determining the second phase value of the voltage across the electrical component of the induction heating circuit at the second driving frequency based on a second measurement of voltage across the capacitor element.

Clause 32: The method of any of clauses 27-31 wherein the induction heating circuit comprises: an inductor element; and a capacitor element.

Clause 33: The method of any of clauses 27-32 wherein the induction heating circuit comprises an electrical component and wherein the electrical component of the induction heating circuit comprises: an inductor element, a capacitor element, or a component of the induction heating circuit that provides a phase that is the same as the phase of a voltage across the inductor element or the capacitor element.

Clause 34: The method of any of clauses 27-33, further comprising: measuring a preliminary third phase of a third AC voltage across the electrical component of the induction heating circuit based on a fourth driving AC voltage at a third driving frequency; adjusting the preliminary third phase using the time delay to provide a corrected preliminary third phase; determining a third response phase of the induction heating circuit at the third driving frequency based on the corrected preliminary third phase, and wherein the third response phase is a value of phase difference between a phase of a driving current at the third driving frequency and a phase of a voltage across the electrical component of the induction heating circuit at the third driving frequency; measuring a preliminary fourth phase of a fourth AC voltage across the electrical component of the induction heating circuit based on a fourth driving AC voltage at a fourth driving frequency; adjusting the preliminary fourth phase using the time delay to provide a corrected preliminary fourth phase; determining a fourth response phase of the induction heating circuit, and wherein the fourth response phase is a value of phase difference between a phase of a driving current at the fourth driving frequency and a phase of a voltage across the electrical component of the induction heating circuit at the fourth driving frequency; and wherein determining the function of phase versus frequency for the induction heating circuit comprises: determining the function of phase versus frequency for the induction heating circuit based on the first response phase, the second response phase, the third response phase, and the fourth response phase.

Clause 35: The method of any of clauses 27-34, wherein the function of phase versus frequency comprises a polynomial, and wherein determining the function of phase versus frequency comprises: determining polynomial coefficients of the polynomial that is fit to the first response phase of the induction heating circuit, the second response phase of the induction heating circuit, the third response phase of the induction heating circuit, and the fourth response phase of the induction heating circuit, and wherein determining the frequency value where the response phase value of the function is in quadrature comprises: determining a frequency value where the phase value of the function of phase versus frequency is in quadrature based on the polynomial coefficients of the polynomial.

Clause 36: The method of any of clauses 27-35, wherein determining the function of phase versus frequency based on the first response phase and the second response phase comprises: determining polynomial coefficients of a polynomial that is fit to the first response phase of the induction heating circuit and the second response phase of the induction heating circuit, and wherein determining the frequency value where the response phase value of the function is in quadrature comprises: determining the frequency value where the phase value of the function of phase versus frequency is in quadrature based on the polynomial coefficients of the polynomial.

Clause 37: The method of any of clauses 27-36, further comprising: determining a temperature of a susceptor element.

Clause 38: The method of any of clauses 27-37, wherein determining the temperature of the susceptor element comprises: determining the temperature of the susceptor element based on a measurement of a magnetic field generated by the inductor element and a frequency value where the phase value of the function of phase versus frequency is in quadrature.

Clause 39: The method of any of clauses 27-38, further comprising: determining a measurement of a magnetic field generated by the inductor element, wherein determining the temperature of the susceptor element comprises: determining the temperature of the susceptor element based on the measurement of the magnetic field generated by the inductor element and the frequency value where the phase value of the function of phase versus frequency is in quadrature.

Clause 40: The method of any of clauses 27-39, wherein determining the temperature of the susceptor element comprises: determining a measurement of a magnetic field generated by the inductor element based on a measurement of: an amplitude of an A/C voltage across the capacitor element, and a frequency of the A/C voltage across the capacitor element; and wherein determining the temperature of the susceptor element comprises: determining the temperature of the susceptor element based on the measurement of the magnetic field generated by the inductor element and the frequency value where the phase value of the function is in quadrature.

Clause 41: The method of any of clauses 27-40, wherein determining the temperature of the susceptor element comprises: determining an amplitude of an A/C voltage across the capacitor element and a frequency of the A/C voltage across the capacitor element; determining a measurement of a magnetic field generated by the inductor element based on the amplitude of an A/C voltage across the capacitor element and the frequency of the A/C voltage across the capacitor element; and determining the temperature of the susceptor element based on the measurement of the magnetic field generated by the inductor element and the frequency value where the phase value of the function is in quadrature.

Clause 42: The method of any of clauses 27-41, wherein determining the temperature of the susceptor element comprises: determining the temperature of the susceptor element based on a frequency value where the phase value of the function of phase versus frequency is in quadrature and an output of at least one temperature sensor.

Clause 43: The method of any of clauses 27-42, wherein determining the temperature of the susceptor element comprises: determining the temperature of the susceptor element based on the frequency value where the phase value of the function is in quadrature and an output of at least one temperature sensor.

Clause 44: The method of any of clauses 27-43, further comprising: determining a temperature of a susceptor element; wherein determining the temperature of the susceptor element comprises: determining the temperature of the susceptor element based on the frequency value where the phase value of the function is in quadrature and a temperature of an inductor element, a capacitor element, or any combination thereof.

Clause 45: The method of any of clauses 27-44, further comprising: determining a temperature of a susceptor element; wherein determining the temperature of the susceptor element comprises: determining the temperature of the susceptor element based on an amount of power absorbed by the susceptor element.

Clause 46: The method of any of clauses 27-45, further comprising: controlling the temperature of the susceptor element.

Clause 47: The method of any of clauses 27-46, wherein controlling the temperature of the susceptor element comprises: controlling a rate at which the temperature of the susceptor element changes based on an amount of power absorbed by the susceptor element.

Clause 48: The method of any of clauses 27-47, further comprising: determining whether a susceptor element is in proximity to an inductor element based on an amount of power absorbed by the susceptor element.

Clause 49: The method of any of clauses 27-48, further comprising: determining an amount of power absorbed by a susceptor element based on the function of phase versus frequency; and wherein determining the temperature of the susceptor element comprises: determining the temperature of the susceptor element based on the amount of power absorbed by the susceptor element.

Clause 50: The method of any of clauses 27-49, further comprising: providing an amount of electrical current to the inductor element based on a time average value of electrical current to be provided to the inductor element to maintain a specified temperature of the susceptor element.

Clause 51: The method of any of clauses 27-50, wherein determining the temperature of the susceptor element comprises: determining the temperature of the susceptor element based on a result of at least one calibration process.

Clause 52: The method of any of clauses 27-51, wherein the result of the at least one calibration process comprises: a reference set of a plurality of values of temperature of the susceptor element and a plurality of frequency values for each of a plurality of phase values of the function that are in quadrature, wherein each of the plurality of frequency values corresponds to each of the plurality of values of temperature of the susceptor element; wherein determining the temperature of the susceptor element comprises: comparing the frequency value where the phase value of the function is in quadrature to the reference set; and determining the temperature of the susceptor element based on a value of temperature in the reference set that corresponds to the frequency value where the phase value of the function is in quadrature.

Clause 53: A computer program product, the computer program product comprising at least one non-transitory computer-readable medium including one or more instructions that, when executed by at least one processor, cause the at least one processor to: generate each line of a plurality of lines, wherein each line comprises a graphical representation of phase value versus frequency of a signal with which an induction heating circuit is driven; determine a line of the plurality of lines that has a maximum slope; determine an average frequency of the line having the maximum slope; determine a phase value corresponding to the average frequency of the line having the maximum slope; determine a time delay, wherein the time delay is equal to a difference of the phase value corresponding the maximum slope and an assumed phase value at quadrature divided by a product of a full period of phase and the average frequency of the line having the maximum slope; determine a self-resonant frequency (SRF) value of the induction heating circuit based on the time delay; and determine a characteristic of the induction heating circuit based on the SRF value.

Clause 54: The computer program product of clause 53, wherein the one or more instructions that cause the at least one processor to determine the SRF value of the induction heating circuit, the at least one processor is programmed or configured to: measure a preliminary first phase of a first AC voltage across an electrical component of the induction heating circuit based on a first driving AC voltage at a first driving frequency; adjust the preliminary first phase using the time delay to provide a corrected preliminary first phase; determine a first response phase of the induction heating circuit at the first driving frequency based on the corrected preliminary first phase, and wherein the first response phase is a value of phase difference between a phase value of a driving current at the first driving frequency and a phase value of the first AC voltage across the electrical component of the induction heating circuit at the first driving frequency; measure a preliminary second phase of a second AC voltage across the electrical component of the induction heating circuit based on a second driving AC voltage at a second driving frequency; adjust the preliminary second phase using the time delay to provide a corrected preliminary second phase; determine a second response phase of the induction heating circuit at the second driving frequency based on the corrected preliminary second phase, and wherein the second response phase is a value of phase difference between a phase value of a driving current at the second driving frequency and a phase value of the second AC voltage across the electrical component of the induction heating circuit at the second driving frequency; determine a function of phase versus frequency for the induction heating circuit based on the first response phase and the second response phase; and determine the SRF value where a phase value of the function of phase versus frequency is in quadrature.

Clause 55: The computer program product of clauses 53 or 54, wherein the one or more instructions that cause the at least one processor to generating each line of the plurality of lines, the at least one processor is programmed or configured to: determine a first phase value of a first AC voltage across an electrical component of the induction heating circuit, wherein the one or more instructions that cause the at least one processor to determine the first phase of the first AC voltage across the electrical component of the induction heating circuit, the at least one programmed or configured to: drive the induction heating circuit with a first driving AC voltage at a first driving frequency; measure the first phase value of the first AC voltage across the electrical component of the induction heating circuit based on the first driving AC voltage at the first driving frequency; determine a second phase value of a second AC voltage across the electrical component of the induction heating circuit, wherein the one or more instructions that cause the at least one processor to determine the second phase value of the second AC voltage across the electrical component of the induction heating circuit, the at least one programmed or configured to: drive the induction heating circuit with a second driving AC voltage at a second driving frequency; measure the second phase value of the second AC voltage across the electrical component of the induction heating circuit based on the second driving AC voltage at the second driving frequency; generate a line of phase versus frequency based on the first phase value at the first driving frequency and the second phase value at the second driving frequency.

Clause 56: The computer program product of any of clauses 53-55, wherein the one or more instructions that cause the at least one processor to determine the line of the plurality of lines that has the maximum slope, cause the at least one processor to: determine a slope of each line of the plurality of lines, wherein the one or more instructions that cause the at least one processor to determine the slope of each line of the plurality of lines, cause the at least one processor to: determine the slope of the line based on a difference of the first phase value and the second phase value divided by a difference of the first driving frequency and the second driving frequency; compare the slope of each line of the plurality of lines to a slope of all other lines of the plurality of lines to provide the line having the maximum slope.

Clause 57: The computer program product of any of clauses 53-56, where the at least one processor is further programmed or configured to: determine the first phase value of the voltage across the electrical component of the induction heating circuit at the first driving frequency based on a first measurement of voltage across a capacitor element of the induction heating circuit; and determine the second phase value of the voltage across the electrical component of the induction heating circuit at the second driving frequency based on a second measurement of voltage across the capacitor element.

Clause 58: The computer program product of any of clauses 53-57, wherein the induction heating circuit comprises: an inductor element; and a capacitor element.

Clause 59: The computer program product of any of clauses 53-58, wherein the induction heating circuit comprises an electrical component and wherein the electrical component of the induction heating circuit comprises: an inductor element, a capacitor element, or a component of the induction heating circuit that provides a phase that is the same as the phase of a voltage across the inductor element or the capacitor element.

Clause 60: The computer program product of any of clauses 53-59, wherein the at least one processor is further programmed or configured to: measure a preliminary third phase of a third AC voltage across the electrical component of the induction heating circuit based on a fourth driving AC voltage at a third driving frequency; adjust the preliminary third phase using the time delay to provide a corrected preliminary third phase; determine a third response phase of the induction heating circuit at the third driving frequency based on the corrected preliminary third phase, and wherein the third response phase is a value of phase difference between a phase of a driving current at the third driving frequency and a phase of a voltage across the electrical component of the induction heating circuit at the third driving frequency; measure a preliminary fourth phase of a fourth AC voltage across the electrical component of the induction heating circuit based on a fourth driving AC voltage at a fourth driving frequency; adjust the preliminary fourth phase using the time delay to provide a corrected preliminary fourth phase; determine a fourth response phase of the induction heating circuit, and wherein the fourth response phase is a value of phase difference between a phase of a driving current at the fourth driving frequency and a phase of a voltage across the electrical component of the induction heating circuit at the fourth driving frequency; and wherein, the one or more instructions that cause the at least one processor to determine the function of phase versus frequency for the induction heating circuit, cause the at least one processor to: determine the function of phase versus frequency for the induction heating circuit based on the first response phase, the second response phase, the third response phase, and the fourth response phase.

Clause 61: The computer program product of any of clauses 53-60, wherein the function of phase versus frequency comprises a polynomial, and wherein, the one or more instructions that cause the at least one processor to determine the function of phase versus frequency, cause the at least one processor to: determine polynomial coefficients of the polynomial that is fit to the first response phase of the induction heating circuit, the second response phase of the induction heating circuit, the third response phase of the induction heating circuit, and the fourth response phase of the induction heating circuit, and wherein, the one or more instructions that cause the at least one processor to determine the frequency value where the response phase value of the function is in quadrature, cause the at least one processor is to: determine a frequency value where the phase value of the function of phase versus frequency is in quadrature based on the polynomial coefficients of the polynomial.

Clause 62: The computer program product of any of clauses 53-61, wherein, the one or more instructions that cause the at least one processor to determine the function of phase versus frequency based on the first response phase and the second response phase, cause the at least one processor to: determine polynomial coefficients of a polynomial that is fit to the first response phase of the induction heating circuit and the second response phase of the induction heating circuit, and wherein, the one or more instructions that cause the at least one processor to determine the frequency value where the response phase value of the function is in quadrature, cause the at least one processor to: determine the frequency value where the phase value of the function of phase versus frequency is in quadrature based on the polynomial coefficients of the polynomial.

Clause 63: The computer program product of any of clauses 53-62, wherein the one or more instructions further cause the at least one processor to: determine a temperature of a susceptor element.

Clause 64: The computer program product of any of clauses 53-63, wherein, the one or more instructions that cause the at least one processor to determine the temperature of the susceptor element, the at least one processor is programmed or configured to: determine the temperature of the susceptor element based on a measurement of a magnetic field generated by the inductor element and a frequency value where the phase value of the function of phase versus frequency is in quadrature.

Clause 65: The computer program product of any of clauses 53-64, wherein the at least one processor is further programmed or configured to: determine a measurement of a magnetic field generated by the inductor element, wherein, the one or more instructions that cause the at least one processor to determine the temperature of the susceptor element, cause the at least one processor to: determine the temperature of the susceptor element based on the measurement of the magnetic field generated by the inductor element and the frequency value where the phase value of the function of phase versus frequency is in quadrature.

Clause 66: The computer program product of any of clauses 53-65, wherein, the one or more instructions that cause the at least one processor to determine the temperature of the susceptor element, the at least one processor is programmed or configured to: determine a measurement of a magnetic field generated by the inductor element based on a measurement of: an amplitude of an A/C voltage across the capacitor element, and a frequency of the A/C voltage across the capacitor element; and wherein, the one or more instructions that cause the at least one processor to determine the temperature of the susceptor element, cause the at least one processor to: determine the temperature of the susceptor element based on the measurement of the magnetic field generated by the inductor element and the frequency value where the phase value of the function is in quadrature.

Clause 67: The computer program product of any of clauses 53-66, wherein, the one or more instructions that cause the at least one processor to determine the temperature of the susceptor element, cause the at least one processor to: determine an amplitude of an AC voltage across the capacitor element and a frequency of the A/C voltage across the capacitor element; determine a measurement of a magnetic field generated by the inductor element based on the amplitude of an A/C voltage across the capacitor element and the frequency of the A/C voltage across the capacitor element; and determine the temperature of the susceptor element based on the measurement of the magnetic field generated by the inductor element and the frequency value where the phase value of the function is in quadrature.

Clause 68: The computer program product of any of clauses 53-67, further comprising: at least one temperature sensor; and wherein, the one or more instructions that cause the at least one processor to determine the temperature of the susceptor element, cause the at least one processor to: determine the temperature of the susceptor element based on a frequency value where the phase value of the function of phase versus frequency is in quadrature and an output of the at least one temperature sensor.

Clause 69: The computer program product of any of clauses 53-68, wherein, the one or more instructions that cause the at least one processor to determine the temperature of the susceptor element, cause the at least one processor to: determine the temperature of the susceptor element based on the frequency value where the phase value of the function is in quadrature and an output of the at least one temperature sensor.

Clause 70: The computer program product of any of clauses 53-69, wherein the one or more instructions further cause the at least one processor to: determine a temperature of a susceptor element; wherein, the one or more instructions that cause the at least one processor to determine the temperature of the susceptor element, cause the at least one processor to: determine the temperature of the susceptor element based on the frequency value where the phase value of the function is in quadrature and a temperature of an inductor element, a capacitor element, or any combination thereof.

Clause 71: The computer program product of any of clauses 53-70, wherein the one or more instructions further cause the at least one processor to: determine a temperature of a susceptor element; wherein, the one or more instructions that cause the at least one processor to determine the temperature of the susceptor element, cause the at least one processor to: determine the temperature of the susceptor element based on an amount of power absorbed by the susceptor element.

Clause 72: The computer program product of any of clauses 53-71, wherein the one or more instructions further cause the at least one processor to: control the temperature of the susceptor element.

Clause 73: The computer program product of any of clauses 53-72, wherein, the one or more instructions that cause the at least one processor to control the temperature of the susceptor element, cause the at least one processor to: control a rate at which the temperature of the susceptor element changes based on an amount of power absorbed by the susceptor element.

Clause 74: The computer program product of any of clauses 53-73, wherein the one or more instructions further cause the at least one processor to: determine whether a susceptor element is in proximity to an inductor element based on an amount of power absorbed by the susceptor element.

Clause 75: The computer program product of any of clauses 53-74, wherein the one or more instructions further cause the at least one processor to: determine an amount of power absorbed by a susceptor element based on the function of phase versus frequency; and wherein, the one or more instructions that cause the at least one processor to determine the temperature of the susceptor element, cause the at least one processor to: determine the temperature of the susceptor element based on the amount of power absorbed by the susceptor element.

Clause 76: The computer program product of any of clauses 53-75, wherein the one or more instructions further cause the at least one processor to: provide an amount of electrical current to the inductor element based on a time average value of electrical current to be provided to the inductor element to maintain a specified temperature of the susceptor element.

Clause 77: The computer program product of any of clauses 53-76, wherein, the one or more instructions that cause the at least one processor to determine the temperature of the susceptor element, cause the at least one processor to: determine the temperature of the susceptor element based on a result of at least one calibration process.

Clause 78: The computer program product of any of clauses 53-77, wherein the result of the at least one calibration process comprises: a reference set of a plurality of values of temperature of the susceptor element and a plurality of frequency values for each of a plurality of phase values of the function that are in quadrature, wherein each of the plurality of frequency values corresponds to each of the plurality of values of temperature of the susceptor element; wherein, the one or more instructions that cause the at least one processor to determine the temperature of the susceptor element, cause the at least one processor to: compare the frequency value where the phase value of the function is in quadrature to the reference set; and determine the temperature of the susceptor element based on a value of temperature in the reference set that corresponds to the frequency value where the phase value of the function is in quadrature.

For purposes of the description hereinafter, the terms "end," "upper," "lower," "right," "left," "vertical," "horizontal," "top," "bottom," "lateral," "longitudinal," and derivatives thereof shall relate to the disclosure as it is oriented in the drawing figures. However, it is to be understood that the disclosure may assume various alternative variations and step sequences, except where expressly specified to the contrary. It is also to be understood that the specific devices and processes illustrated in the attached drawings, and described in the following specification, are simply exemplary embodiments or aspects of the disclosure. Hence, specific dimensions and other physical characteristics related to the embodiments or aspects of the embodiments disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" and "based at least in part on" unless explicitly stated otherwise. The phrase "based on" may also mean "in response to" where appropriate.

In some non-limiting embodiments, a device, such as a vaporizer device, includes an induction heating circuit. In some non-limiting embodiments, the induction heating circuit includes an inductor element and a susceptor element. The induction heating circuit may be used to heat an object, such as a material (e.g., an organic material, a synthetic material, etc.) that is in thermal contact with the susceptor element. For example, the inductor element provides an electromagnetic field that causes the susceptor element to generate heat and the susceptor element may be used to heat an object that is in thermal contact with the susceptor element (e.g., adjacent the susceptor element so that an object can be heated by the susceptor element, in contact with the susceptor element so that an object can be heated by the susceptor element, etc.).

In some non-limiting embodiments, the temperature of the susceptor element is controlled based on measuring the temperature of the susceptor element. In some non-limiting embodiments, the temperature of the susceptor element is controlled so that a chemical composition of a vapor or aerosol produced by a material (e.g., a vaporizable substance or a substance for vaping) that is heated by the induction heating circuit is within a desired temperature range based on the chemical composition. In some non-limiting embodiments, the desired temperature range includes a sufficiently high temperature to produce an aerosol that is satisfying to the user while not exposing any material to excess temperature. In particular, the desired temperature range can depend on the chemistry of the particular material to be vaped. For example, for an e-liquid containing propylene glycol, vegetable glycerin and nicotine, the desired temperature range includes the region of 188 C but not to exceed 250 C. In some non-limiting embodiments, a vaporizable substance is a dry herbal material such as tobacco or herbal medicines that, similarly, when heated to the correct temperature provides the desired effect of delivering an aerosol to be inhaled with no or minimal combustion of the vaporizable substance.

In some applications, the use of temperature sensing devices can pose certain challenges. For example, using a temperature sensing device, such as a thermocouple, a sensor chip, and/or an infrared thermometer to sense the temperature of an element (e.g., a susceptor element in a device, such as a vaporizer device) may be difficult based on the size of the susceptor element and/or the size of the temperature sensing device used to measure the temperature of the susceptor element.

As an example, in a vaporizer device where an induction heating circuit is compact, the size of a temperature sensing device may prevent the temperature sensing device from being able to be used to sense the temperature of the susceptor element because the temperature sensing device cannot be in thermal contact with the susceptor element. In addition, the temperature sensing device may not be able to accurately sense the temperature of the susceptor element because the temperature sensing device is not able to be in thermal contact with the susceptor element. Further, in some instances, the temperature sensing device may not be able to be in thermal contact with the susceptor element because the temperature sensing device may not be able to withstand the temperature of the susceptor element. In other instances, a control device of a vaporizer device may not be able to receive information from a temperature sensing device. For example, the control device may not be able to receive information from the temperature sensing device because of a physical impediment (e.g., an amount of material on a component, such as a cartridge, in which the temperature sensing device is positioned) that interferes with communication between the control device and the temperature sensing device.

To address at least some of these issues, the present disclosure includes non-limiting embodiments that are directed to systems, methods, and computer program products for determining a characteristic of an induction heating circuit. In some non-limiting embodiments, a system may include an induction heating circuit; and at least one processor programmed or configured to generate each line of a plurality of lines, wherein each line comprises a graphical representation of phase value versus frequency of a signal with which the induction heating circuit is driven, determine a line of the plurality of lines that has a maximum slope, determine an average frequency of the line having the maximum slope, determine a phase value corresponding to the average frequency of the line having the maximum slope, determine a time delay, where the time delay is equal to the difference of the phase value corresponding the maximum slope and an assumed phase value at quadrature divided by a product of a full period of phase and the average frequency of the line having the maximum slope, determine a self-resonant frequency (SRF) value of the induction heating circuit based on the time delay, and determine a characteristic of the induction heating circuit based on the resonant frequency value.

In this way, embodiments of the present disclosure allow for an accurate determination of a characteristic of an induction heating circuit based on a response of the induction heating circuit (e.g., based on a response of an inductor element or a capacitor element of the induction heating circuit) to an excitation, without any components of the system being in thermal contact (e.g., physical contact such that heat transfer would occur based on conduction between the susceptor element and the component) with a susceptor element. In addition, embodiments of the present disclosure allow for reducing the cost associated with disposal components that include a susceptor element, such as a cartridge that includes a susceptor element and a vaporizable material. The cartridge may be disposable and may be replaced in a vaporizer device when the vaporizable material within the cartridge is used up. The cartridge may be of a reduced cost to manufacture compared to a component that includes additional circuitry, such as a cartridge with a circuit, temperature sensor, and/or the like, to determine a temperature of a susceptor within the cartridge.

FIG. 1 is a diagram of a non-limiting embodiment of system 100 in which systems, methods, and/or computer program products as disclosed herein may be implemented. In some non-limiting embodiments, system 100 is a component within a device, a system, and/or the like. For example, system 100 may be a component within a vaporizer device as described herein. In some non-limiting embodiments, system 100 may be implemented as an induction heating system and/or a system.

As shown in FIG. 1, system 100 includes control device 110, inductor element 120, power source 130, and susceptor element 140. In some non-limiting embodiments, as further shown in FIG. 1, system 100 includes induction heating circuit 150, capacitor element 160, and sensor element 170. In some non-limiting embodiments, induction heating circuit 150 includes inductor element 120 and capacitor element 160.

In some non-limiting embodiments, control device 110 includes one or more devices capable of controlling power source 130 to provide power to one or more components (e.g., inductor element 120) of system 100, and/or determining a characteristic of susceptor element 140. In one example, control device 110 is configured to determine a characteristic (e.g., a temperature) of susceptor element 140 based on a magnetic field associated with inductor element 120 (e.g., a response of the magnetic field to a change of a magnetic property of susceptor element 140). For example, control device 110 includes a computing device, such as a computer, a processor, a microprocessor, a controller, and/or the like. In some non-limiting embodiments, control device 110 includes one or more electrical circuits that provide power conditioning for power provided by power source 130.

In some non-limiting embodiments, inductor element 120 includes one or more electrical components and/or one or more devices capable of providing electromagnetic energy to susceptor element 140 and/or receiving electromagnetic energy from susceptor element 140. For example, inductor element 120 includes an induction coil such as a planar or pancake inductor, or a spiral inductor. In some non-limiting embodiments, inductor element 120 is configured to provide electromagnetic energy (e.g., in the form of a magnetic field, such as a magnetic induction field, in the form of electromagnetic radiation, etc.) to susceptor element 140 to cause susceptor element 140 to generate heat based on receiving the electromagnetic energy. In some non-limiting embodiments, inductor element 120 is separate from another inductor element that provides electromagnetic energy to susceptor element 140. In some non-limiting embodiments, inductor element 120 has a size and configuration (e.g., a design) based on the application for which induction heating circuit 150 is applied. In some non-limiting embodiments, inductor element 120 has a length in the range between 4 mm to 20 mm. In one example, inductor element 120 has a length of about 8 mm. In some non-limiting embodiments, inductor element 120 has a width (e.g., a diameter) in the range between 2 mm to 20 mm. In one example, inductor element 120 has a width of about 7 mm. In one example, inductor element 120 includes an induction coil that has 12 turns of 22 gauge wire in 2 layers with an inside diameter of about 6 mm. In some non-limiting embodiments, inductor element 120 has an inductance value in the range between 0.5 µH to 6 µH. In one example, inductor element 120 has an inductance value of about 0.9 µH.

In some non-limiting embodiments, power source 130 includes one or more devices capable of providing power to induction heating circuit 150 and/or control device 110. For example, power source 130 includes an alternating electrical current (AC) power supply (e.g., a generator, an alternator, etc.) and/or a direct current (DC) power supply (e.g., a battery, a capacitor, a fuel cell, etc.). In some non-limiting embodiments, power source 130 is configured to provide power to one or more components of system 100. In some non-limiting embodiments, power source 130 includes one or more electrical circuits that provide power conditioning for power provided by power source 130.

In some non-limiting embodiments, susceptor element 140 includes one or more devices capable of absorbing electromagnetic energy, generating heat based on electromagnetic energy that is absorbed, and/or providing heat (e.g., providing heat via conduction, providing heat via radiation, etc.) to an object (e.g., a substance, a device, a component, etc.) that is in thermal contact with the one or more devices. For example, susceptor element 140 includes a device constructed of a material that is electrically conductive. In some non-limiting embodiments, susceptor element 140 is electromagnetically coupled to inductor element 120. In some non-limiting embodiments, susceptor element 140 includes a metallic conductor that heats by eddy currents, iron, steel (e.g., stainless steel), a ceramic magnet (e.g., ferrite), an FeCrAl alloy, Kanthal, and/or a semiconductor. In some non-limiting embodiments, susceptor element 140 has a length in the range between 5 mm to 18 mm. In one example, susceptor element 140 includes 430 alloy stainless steel and has a length of about 15 mm. In some non-limiting embodiments, inductor element 120 is electromagnetically coupled to susceptor element 140.

In some non-limiting embodiments, susceptor element 140 has a configuration that is based on a geometry (e.g., a shape) of susceptor element 140. Additionally or alternatively, the configuration of susceptor element 140 is based on a predetermined type and/or amount of one or more materials from which susceptor element 140 is constructed. In some non-limiting embodiments, the configuration of susceptor element 140 defines the magnetic properties associated with susceptor element 140, such as magnetization of susceptor element 140 and/or an amplitude of a magnetic field generated by susceptor element 140. In some non-limiting embodiments, susceptor element 140 has a configuration that includes a stranded wire, a stranded rope of material, a mesh, a mesh tube, several concentric mesh tubes, a cloth, a sheet of material, a porous solid (e.g., a foam), a roll of metal mesh, fibers of metal, or any other geometry that is appropriately sized and/or configured. In some non-limiting embodiments, susceptor element 140 includes fins, protrusions, or other details that are configured to hold a solid and/or semi-solid material in thermal contact with susceptor element 140.

In some non-limiting embodiments, susceptor element 140 is constructed of a combination of materials to achieve an appropriate effect. For example, susceptor element 140 includes an interwoven cloth (or otherwise intimately mixed combination) of fine induction heating wires, strands, and/or threads with wicking wires, strands, and/or threads. Additionally or alternatively, susceptor element 140 comprises materials combined in the form of a rope or foam, or suitably deployed thin sheets of material. In some non-limiting embodiments, susceptor element 140 includes rolled up alternating foils of material. Additionally or alternatively, susceptor element 140 is surrounded (e.g., partially, completely, and/or the like) by inductor element 120, which is not necessarily in contact with susceptor element 140. In some non-limiting embodiments, susceptor element 140 includes a mesh wick. In some non-limiting embodiments, the mesh wick is constructed of a material that is efficiently heated by induction (e.g., a FeCrAl alloy or ferritic stainless steel alloy). In some non-limiting embodiments, the mesh wick is formed using a Kanthal mesh. Additionally or alternatively, susceptor element 140 is removable from a cartridge so that susceptor element 140 can be cleaned, reused, and/or replaced separate from the cartridge.

In some non-limiting embodiments, the materials used in construction of susceptor element 140 include a magnetic material and/or a metallic conductor. Additionally or alternatively, susceptor element 140 includes materials that produce heat based on eddy currents and/or magnetic hysteresis when susceptor element 140 is exposed to electromagnetic energy. For example, magnetic and/or metallic conductor materials that have considerable hysteresis in the range between electromagnetic fields are used in the construction of susceptor element 140. In some non-limiting embodiments, susceptor element 140 includes a material such that heating is carried out both by eddy currents and also by movement of the magnetic domain walls. In some non-limiting embodiments, the material from which susceptor element 140 is constructed includes iron. In some non-limiting embodiments, susceptor element 140 includes ceramic magnets, such as ferrite. In some non-limiting embodiments, susceptor element 140 includes a semiconductor.

In some non-limiting embodiments, susceptor element 140 is configured to transfer a vaporizable substance from the reservoir based on a capillary action of susceptor element 140. In some non-limiting embodiments, the vaporizable substance is a viscous substance (e.g., a liquid), and as the viscous substance is vaporized, more of the viscous substance moves from the reservoir to a heated part of susceptor element 140. In some non-limiting embodiments, inductor element 120 is configured to create a magnetic field around susceptor element 140. In some non-limiting embodiments, at least a portion of susceptor element 140 is positioned within a cartridge and at least a portion of the cartridge is positioned within inductor element 120. In some non-limiting embodiments, susceptor element 140 is positioned within a cartridge and the cartridge is positioned within inductor element 120 (e.g., as shown by susceptor element 540 positioned within cartridge 518 in FIG. 5).

Figure 4A:
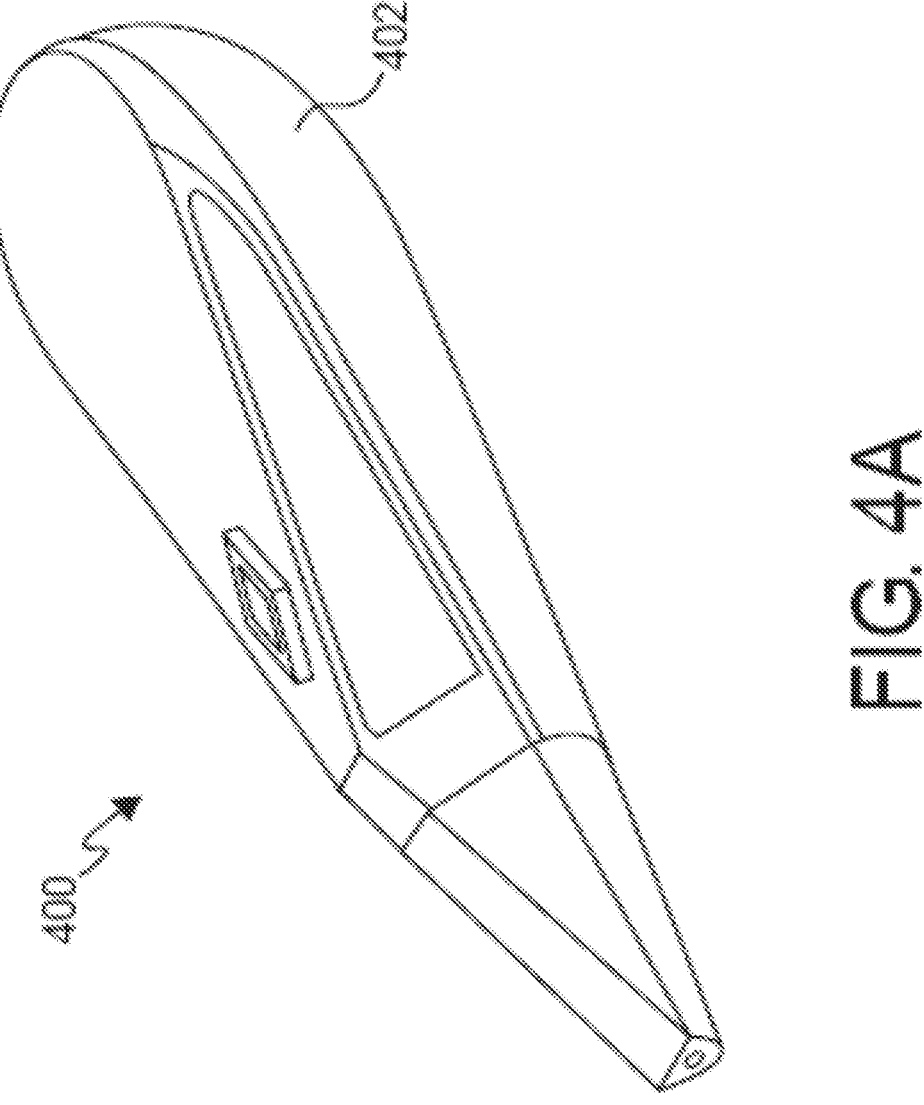
FIGS. 4A-4C are diagrams of a non-limiting embodiment of a vaporizer device.
Figure 4B:
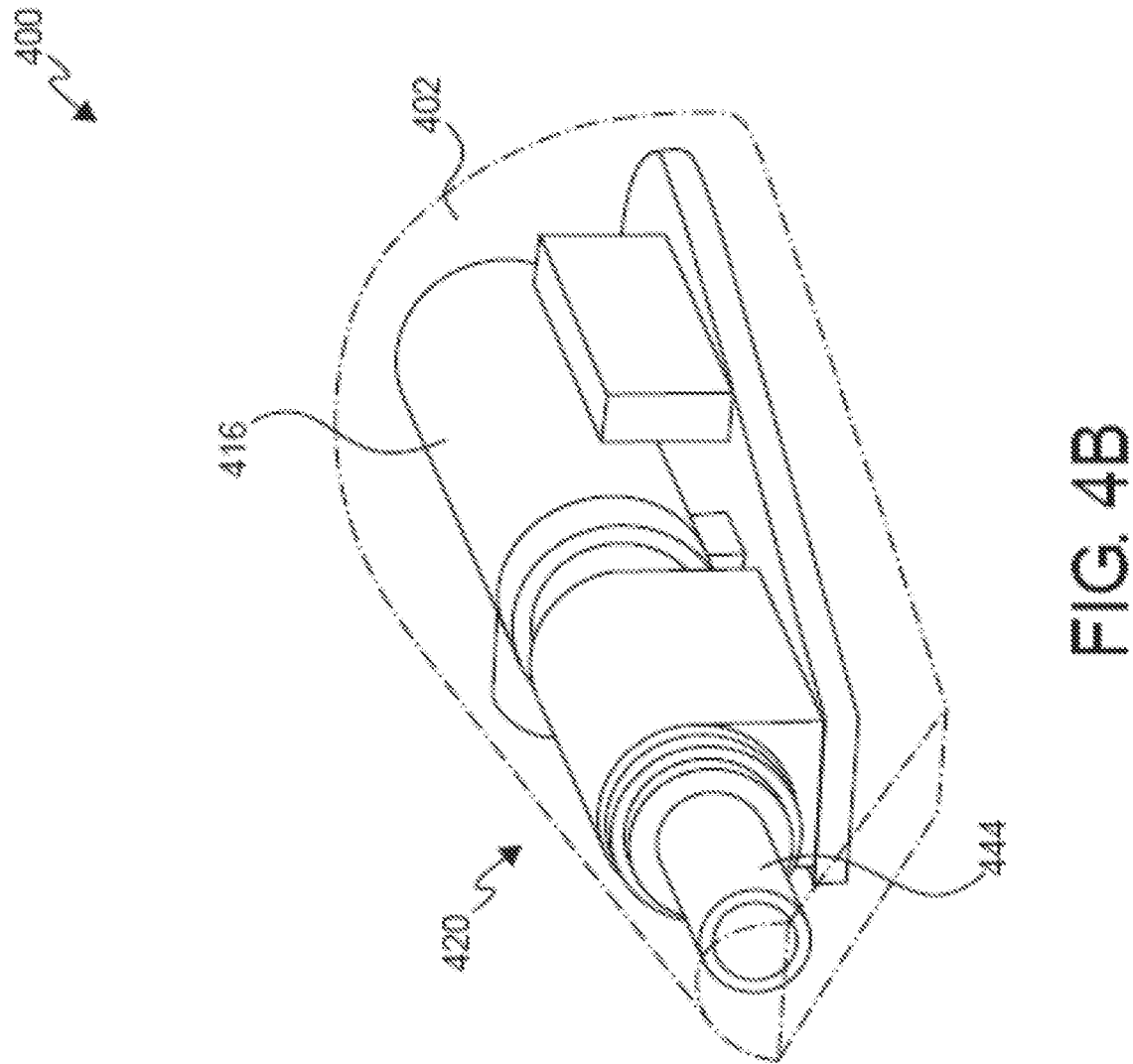
Figure 4C:
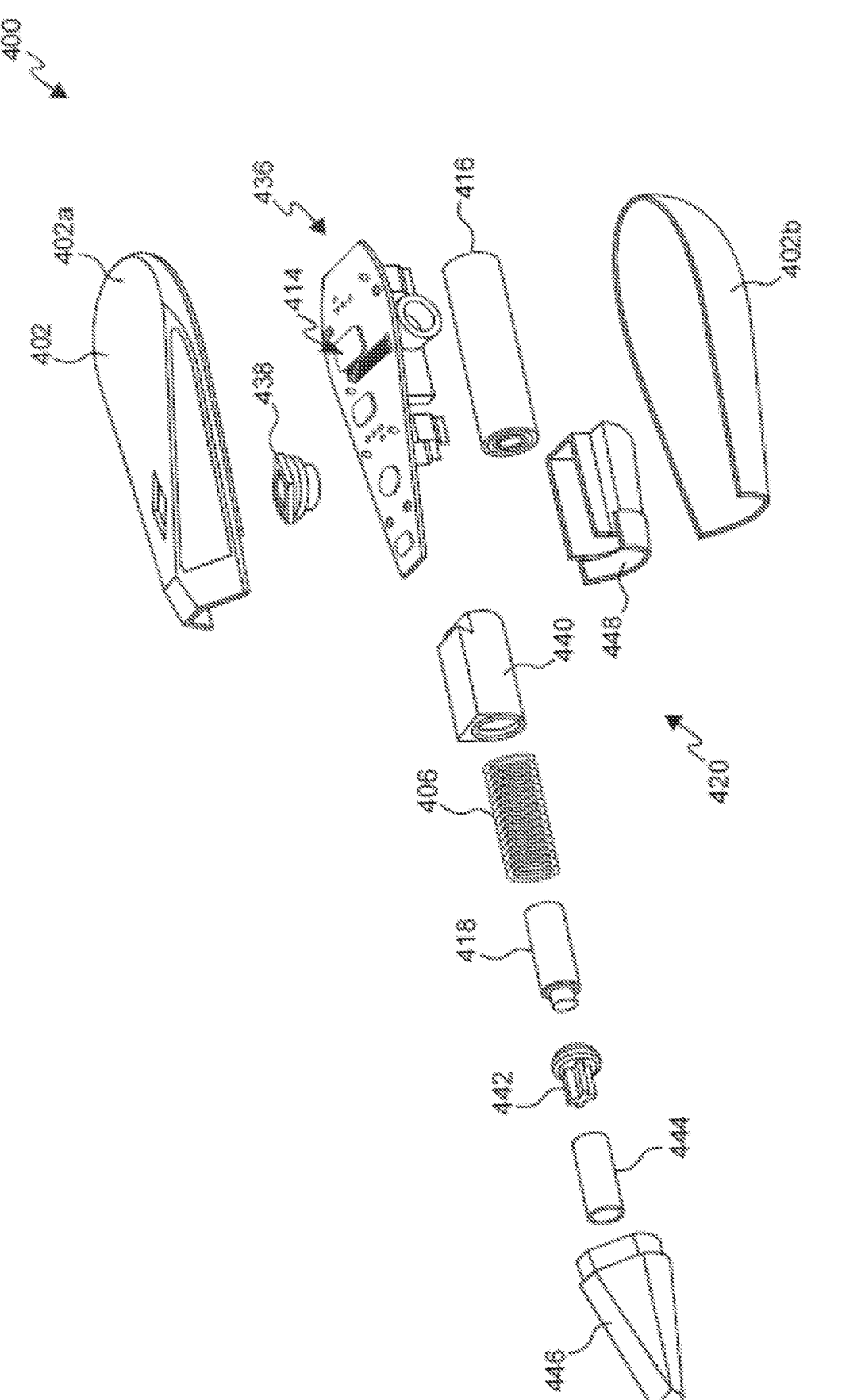

In some non-limiting embodiments, susceptor element 140 is associated with a vaporizer device (e.g., vaporizer device 400 shown in FIGS. 4A-4C). In some non-limiting embodiments, control device 110 is configured to detect a change in a magnetic property of susceptor element 140.

In some non-limiting embodiments, system 100 includes an induction heating circuit 150 and inductor element 120 is a component of induction heating circuit 150. In some non-limiting embodiments, induction heating circuit 150 includes inductor element 120 and capacitor element 160. In some non-limiting embodiments, inductor element 120 and capacitor element 160 are electrically connected. For example, induction heating circuit 150 includes inductor element 120 electrically connected in parallel with capacitor element 160. In another example, induction heating circuit 150 includes inductor element 120 electrically connected in series with capacitor element 160. In some non-limiting embodiments, induction heating circuit 150 is configured to cause susceptor element 140 to generate heat.

In some non-limiting embodiments, capacitor element 160 includes one or more electrical components and/or one or more devices capable of providing an amount of capacitance in an electrical circuit. For example, capacitor element 160 includes a capacitor such as a parallel-plate capacitor. In some non-limiting embodiments, capacitor element 160 has a size and configuration based on the application for which induction heating circuit 150 is applied. In some non-limiting embodiments, capacitor element 160 has a length in the range between 3.3 mm to 16 mm. In one example, capacitor element 160 has a length of about 6 mm. In some non-limiting embodiments, capacitor element 160 has a width in the range between 1.7 mm to 15 mm. In one example, capacitor element 160 has a width of about 5 mm. In one example, capacitor element 160 includes a surface mount capacitor or more than one surface mount capacitor in parallel or series, such as a surface mount capacitor or capacitors of a standard size 2220 (e.g., 5.6 mm×5 mm). In some non-limiting embodiments, capacitor element 160 has a capacitance value in the range between 0.1 μF to 10 μF. In one example, capacitor element 160 has a capacitance value of about 1.36 μF.

In some non-limiting embodiments, system 100 includes sensor element 170. In some non-limiting embodiments, sensor element 170 is connected to control device 110. In some non-limiting embodiments, sensor element 170 is a component of induction heating circuit 150. In some non-limiting embodiments, sensor element 170 includes one or more electrical components and/or one or more devices capable of detecting a magnetic field (e.g., one or more characteristics of a magnetic field) associated with inductor element 120. For example, sensor element 170 includes a sensor, such as a semiconductor sensor that senses a magnetic field and/or a hall-effect sensor. In some non-limiting embodiments, sensor element 170 includes a temperature sensor. Additionally or alternatively, sensor element 170 includes an inductor element (e.g., another inductor element 120).

In some non-limiting embodiments, control device 110 is configured to determine a response of induction heating circuit 150 to a change in a magnetic property of susceptor element 140 and to determine a temperature of susceptor element 140 based on the response of induction heating circuit 150. In some non-limiting embodiments, control device 110 is configured to determine whether susceptor element 140 is near (e.g., in proximity to) induction heating circuit 150. For example, control device 110 is configured to determine whether susceptor element 140 is near induction heating circuit 150 and/or inductor element 120 based on the response of induction heating circuit 150.

In some non-limiting embodiments, control device 110 is configured to determine a response of induction heating circuit 150 to a change of a magnetic property of susceptor element 140. For example, control device 110 is configured to determine a self-resonant frequency (SRF) value associated with induction heating circuit 150. In some non-limiting embodiments, control device 110 is configured to determine a temperature of susceptor element 140 based on the response of induction heating circuit 150. For example, control device 110 is configured to determine the temperature of susceptor element 140 based on an SRF value associated with induction heating circuit 150.

In some non-limiting embodiments, control device 110 is configured to determine a response of induction heating circuit 150 to a change in a magnetic property of susceptor element 140 by determining an SRF value associated with induction heating circuit 150 and compare the SRF value to a frequency value associated with susceptor element 140. In some non-limiting embodiments, control device 110 is configured to determine whether susceptor element 140 is near induction heating circuit 150 based on comparing the SRF value to the frequency value associated with susceptor element 140. In some non-limiting embodiments, control device 110 is configured to determine a temperature of the susceptor element based on the response of the induction heating circuit and based on determining that susceptor element 140 is near induction heating circuit 150.

In some non-limiting embodiments, control device 110 is configured to determine a response of induction heating circuit 150 to a change of a magnetic property of susceptor element 140 by determining an SRF value associated with induction heating circuit 150 and determine a first temperature of susceptor element 140 based on the response of the induction heating circuit. In some non-limiting embodiments, control device 110 is configured to adjust an amount of electrical energy (e.g., electrical current and/or voltage) provided to induction heating circuit 150 to cause susceptor element 140 to change from the first temperature to a second temperature based on determining the first temperature of susceptor element 140.

Figure 2:
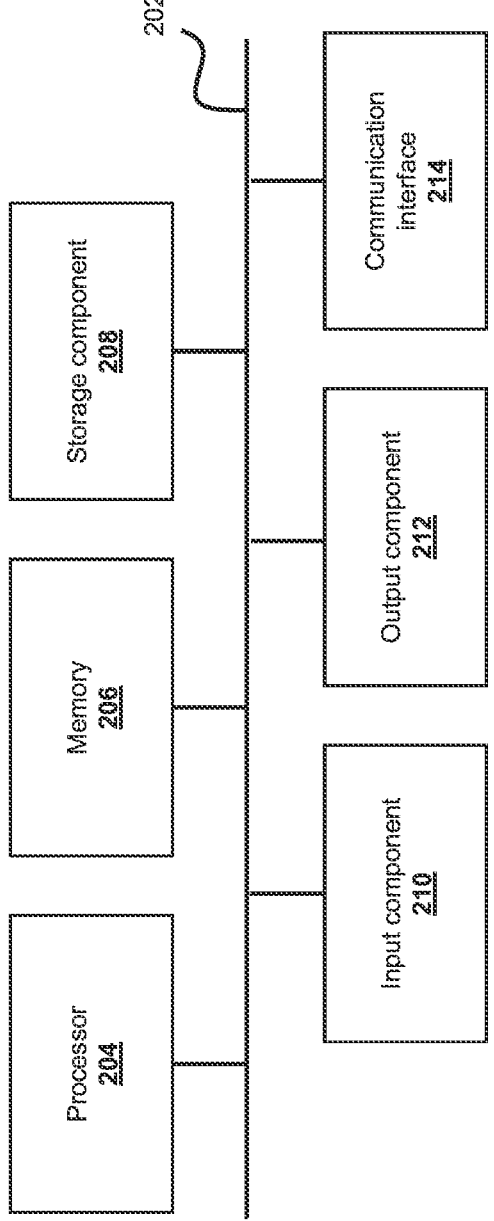
FIG. 2 is a diagram of a non-limiting embodiment of components of one or more devices of FIG. 1.

Referring now to FIG. 2, FIG. 2 is a diagram of example components of a device 200. Device 200 may correspond to control device 110. In some non-limiting embodiments, control device 110 includes at least one device 200 and/or at least one component of device 200. As shown in FIG. 2, device 200 includes bus 202, processor 204, memory 206, storage component 208, input component 210, output component 212, and communication interface 214.

Bus 202 includes a component that permits communication among the components of device 200. In some non-limiting embodiments, processor 204 is implemented in hardware, software (e.g., firmware), or a combination of hardware and software. For example, processor 204 includes a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 includes random access memory (RAM), read only memory (ROM), and/or another type of dynamic or static storage device (e.g., flash memory, magnetic memory, optical memory, etc.) that stores information and/or instructions for use by processor 204.

In some non-limiting embodiments, storage component 208 stores information and/or software related to the operation and use of device 200. For example, storage component 208 includes a hard disk (e.g., a magnetic disk, an optical disk, a magneto-optic disk, a solid state disk, etc.), a compact disc (CD), a digital versatile disc (DVD), a floppy disk, a cartridge, a magnetic tape, a flash memory device (e.g., a flash drive), and/or another type of computer-readable medium, along with a corresponding drive.

In some non-limiting embodiments, input component 210 includes a component that permits device 200 to receive information, such as via user input (e.g., a touch screen display, a keyboard, a keypad, a mouse, a button, a switch, a microphone, etc.). Additionally or alternatively, input component 210 includes a sensor for sensing information (e.g., a temperature sensor, an accelerometer, a gyroscope, an actuator, a pressure sensor, etc.). Output component 212 includes a component that provides output information from device 200 (e.g., a display, a speaker, one or more light-emitting diodes (LEDs), etc.).

In some non-limiting embodiments, communication interface 214 includes a transceiver-like component (e.g., a transceiver, a separate receiver and transmitter, etc.) that enables device 200 to communicate with other devices, such as via a wired connection, a wireless connection, or a combination of wired and wireless connections. In some non-limiting embodiments, communication interface 214 permits device 200 to receive information from another device and/or provide information to another device. For example, communication interface 214 includes an Ethernet interface, an optical interface, a coaxial interface, an infrared interface, a radio frequency (RF) interface, a universal serial bus (USB) interface, a Wi-Fi® interface, a cellular network interface, a Bluetooth® interface, and/or the like.

In some non-limiting embodiments, device 200 performs one or more processes described herein. In some non-limiting embodiments, device 200 performs these processes based on processor 204 executing software instructions stored by a computer-readable medium, such as memory 206 and/or storage component 208. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions are read into memory 206 and/or storage component 208 from another computer-readable medium or from another device via communication interface 214. In some non-limiting embodiments, when executed, software instructions stored in memory 206 and/or storage component 208 cause processor 204 to perform one or more processes described herein. Additionally or alternatively, hardwired circuitry is used in place of or in combination with software instructions to perform one or more processes described herein. Thus, embodiments described herein are not limited to any specific combination of hardware circuitry and software.

The number and arrangement of components shown in FIG. 2 are provided as an example. In some non-limiting embodiments, device 200 includes additional components, fewer components, different components, or differently arranged components than those shown in FIG. 2. Additionally or alternatively, a set of components (e.g., one or more components) of device 200 may perform one or more functions described as being performed by another set of components of device 200.

Referring now to FIG. 3A, FIG. 3A is a flowchart of a non-limiting embodiment of a method 300A for determining a characteristic of an induction heating circuit (e.g., induction heating circuit 150) in a system, such as an induction heating system. In some non-limiting embodiments, one or more of the steps of method 300A are performed (e.g., completely, partially, etc.) by control device 110. In some non-limiting embodiments, one or more of the steps of method 300A are performed by another device or a group of devices separate from or including control device 110.

As shown in FIG. 3A, at step 302A, method 300A includes generating a plurality of lines. For example, control device 110 generates each line of the plurality of lines. Each line is a graphical representation of a phase response versus frequency of a signal with which the induction heating circuit is driven by control device 110. In some non-limiting embodiments, when generating each line of the plurality of lines, control device 110 determines a first phase value of a first AC voltage across an electrical component of the induction heating circuit and a second phase value of a second AC voltage response across the electrical component of the induction heating circuit. In some non-limiting embodiments, control device 110 determines the first phase of the first AC voltage across the electrical component, such as capacitor element 160, of induction heating circuit 150. For example, control device 110 drives induction heating circuit 150 with a first driving AC voltage at a first driving frequency and measures the first phase value of the first AC voltage across the electrical component of the induction heating circuit based on the first driving AC voltage at the first driving frequency. In some non-limiting embodiments, control device 110 determines the first phase of the first AC voltage across the electrical component, such as capacitor element 160, of induction heating circuit 150. For example, control device 110 drives induction heating circuit 150 with a second driving AC voltage at a second driving frequency and measures the second value of phase of the second AC voltage response across the electrical component of the circuit based on the second driving AC voltage at the second driving frequency. In some non-limiting embodiments, for each line of the plurality of lines, control device 110 generates a line of phase versus frequency based on the first phase value at the first driving frequency and the second phase value at the second driving frequency.

As shown in FIG. 3A, at step 304A, method 300A includes determining an average frequency of a line having a maximum slope. For example, control device 110 determines the average frequency of the line having a maximum slope. In some non-limiting embodiments, control device 110 determines the average frequency of the line having the maximum slope based on an average of a first driving frequency and a second driving frequency of the line. In some non-limiting embodiments, control device 110 determines the average frequency of the line having the maximum slope based on determining the line of the plurality of lines that has the maximum slope.

In some non-limiting embodiments, control device 110 determines a line of the plurality of lines that has a maximum slope. For example, control device 110 determines a slope of each line of the plurality of lines and compares the slope of each line of the plurality of lines to a slope of all other lines of the plurality of lines to provide the line having the maximum slope. In some non-limiting embodiments, control device 110 determines the slope of a line based on a difference of the first phase value at the first driving frequency and the second phase value at the second driving frequency divided by a difference of the first driving frequency and the second driving frequency.

As shown in FIG. 3A, at step 306A, method 300A includes determining a phase value corresponding to the average frequency. For example, control device 110 determines the phase value corresponding to the average frequency of the line having the maximum slope.

As shown in FIG. 3A, at step 308A, method 300A includes determining a time delay based on the average frequency and the phase value. For example, control device 110 determines the time delay based on the average frequency of the line having the maximum slope and the phase value corresponding to the average frequency of the line having the maximum slope. In some non-limiting embodiments, the time delay is an amount of time between the excitation of induction heating circuit 150 based on an input provided by control device 110 and the response of induction heating circuit 150. In some non-limiting embodiments, the time delay is equal to a difference of the phase value corresponding the maximum slope and an assumed phase value at quadrature divided by a product of a full period of phase and the average frequency of the line having the maximum slope. In some non-limiting embodiments, the assumed phase value at quadrature is a value in the range between 88 degrees and 92 degrees. In one example, the assumed phase value at quadrature is equal to 90 degrees.

In some non-limiting embodiments, control device 110 determines the difference of the phase value corresponding to the maximum slope and the assumed phase value at quadrature. In some non-limiting embodiments, control device 110 determines the product of a full period of phase and the average frequency of the line having the maximum slope. In some non-limiting embodiments, control device 110 divides the difference of the phase value corresponding to the maximum slope and the assumed phase value at quadrature by the product of a full period of phase and the average frequency of the line having the maximum slope to provide the time delay.

As shown in FIG. 3A, at step 310A, method 300A includes determining a self-resonant frequency based on the time delay. For example, control device 110 determines a self-resonant frequency (SRF) value of induction heating circuit 150 based on the time delay.

In one example, control device 110 measures a preliminary first phase of a first AC voltage across an electrical component, such as capacitor element 160, of induction heating circuit 150 based on a first driving AC voltage at a first driving frequency, adjusts the preliminary first phase using the time delay to provide a corrected preliminary first phase, and determines a first response phase of induction heating circuit 150 at the first driving frequency based on the corrected preliminary first phase. In some non-limiting embodiments, the first response phase is a value of phase difference between a phase value of a driving current at the first driving frequency and a phase value of the first AC voltage across the electrical component of induction heating circuit 150 at the first driving frequency. In the example above, control device 110 measures a preliminary second phase of a second AC voltage across the electrical component of induction heating circuit 150 based on a second driving AC voltage at a second driving frequency, adjusts the preliminary second phase using the time delay to provide a corrected preliminary second phase, and determines a second response phase of induction heating circuit 150 at the second driving frequency based on the corrected preliminary second phase. In some non-limiting embodiments, the second response phase is a value of phase difference between a phase value of a driving current at the second driving frequency and a phase value of the second AC voltage across the electrical component of the induction heating circuit 150 at the second driving frequency. Further, in the example above, control device 110 determines a function of phase versus frequency for induction heating circuit 150 based on the first response phase and the second response phase and determines the SRF value based on the function of phase versus frequency. In some non-limiting embodiments, the SRF value is equal to a frequency value corresponding to a phase value of the function that is in quadrature (e.g., corresponding to a phase value of 90 degrees).

As shown in FIG. 3A, at step 312A, method 300A includes determining a characteristic based on the self-resonant frequency. For example, control device 110 determines the characteristic of induction heating circuit 150 based on the SRF value of induction heating circuit 150. In some non-limiting embodiments, the characteristic of induction heating circuit 150 includes the magnetic field produced by inductor element 120 and hence the inductance of inductor element 120 of induction heating circuit 150. In some non-limiting embodiments, the characteristic of induction heating circuit 150 includes a change in temperature of susceptor element 140 which causes a change in the magnetization of susceptor element 140. In some non-limiting embodiments, the characteristic of induction heating circuit 150 includes a change in resistivity of susceptor element 140, which causes a change in the eddy currents induced in susceptor element 140 by the magnetic field produced by inductor element 120. In some non-limiting embodiments, the characteristic of induction heating circuit 150 includes a phase change of a material of susceptor element 140.

In some non-limiting embodiments, control device 110 performs an action based on the characteristic of the induction heating circuit. For example, control device 110 controls a desired power level to be output by induction heating circuit 150. In such an example, control device 110 may cause susceptor element 140 to generate heat. In another example, control device 110 may shut off the power output by induction heating circuit 150. In another example, control device 110 may determine whether susceptor element 140 is present. In some non-limiting embodiments, control device 110 may limit the power output by induction heating circuit 150 and/or provide a warning indication based on determining that the susceptor element 140 is not present.

Figure 3B:
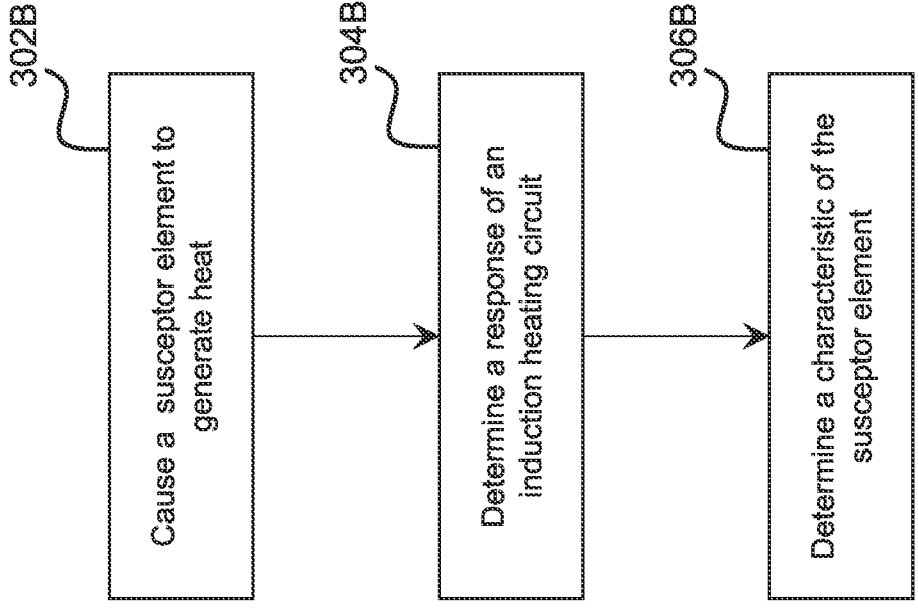
FIG. 3B is a flowchart of a non-limiting embodiment of a method of determining a characteristic of a susceptor element.

Referring now to FIG. 3B, FIG. 3B is a flowchart of a non-limiting embodiment of a method 300B for determining a characteristic of a susceptor element (e.g., susceptor element 140) in a system, such as an induction heating system. In some non-limiting embodiments, one or more of the steps of method 300B are performed (e.g., completely, partially, etc.) by control device 110. In some non-limiting embodiments, one or more of the steps of method 300B are performed by another device or a group of devices separate from or including control device 110.

As shown in FIG. 3B, at step 302B, method 300B includes causing a susceptor element to generate heat. For example, control device 110 causes inductor element 120 to provide electromagnetic energy that is received by susceptor element 140. In some non-limiting embodiments, susceptor element 140 generates heat within susceptor element 140 based on electric currents that are generated inside susceptor element 140 and/or magnetic hysteresis based on electromagnetic energy being received by susceptor element 140. In some non-limiting embodiments, control device 110 causes inductor element 120 to produce (e.g., radiate) a magnetic field based on an alternating electrical current provided to inductor element 120 as an input. In some non-limiting embodiments, inductor element 120 creates a magnetic field around susceptor element 140.

In some non-limiting embodiments, inductor element 120 is powered by power source 130. For example, inductor element 120 receives electrical energy from power source 130 based on control device 110 controlling an amount of electrical current and/or voltage provided to and received by inductor element 120. In some non-limiting embodiments, control device 110 controls an amount of electrical energy provided by power source 130. In some non-limiting embodiments, control device 110 causes inductor element 120 to produce a magnetic field to be received by (e.g., absorbed by) susceptor element 140. For example, control device 110 provides a control signal to inductor element 120, and inductor element 120 produces the magnetic field to be received by susceptor element 140 based on the control signal from control device 110.

In some non-limiting embodiments, the electrical energy received by inductor element 120 includes an alternating electrical current. For example, control device 110 receives a direct electrical current (e.g., a DC electrical current) from power source 130 and control device 110 converts the direct electrical current to an alternating electrical current (e.g., an AC electrical current). In some non-limiting embodiments, control device 110 provides the alternating electrical current to inductor element 120. In some non-limiting embodiments, a frequency value of the alternating electrical current is in the range between 10 kHz to 10 MHz. In some non-limiting embodiments, a frequency value of the alternating electrical current is in the range between 10 kHz to 100 GHz.

In some non-limiting embodiments, control device 110 provides an alternating electrical current with a frequency value in the range between 10 kHz to 10 MHz to induction heating circuit 150 (e.g., inductor element 120 of induction heating circuit 150) and inductor element 120 generates an electromagnetic field based on the alternating electrical current. In some non-limiting embodiments, susceptor element 140 includes an amount of ferromagnetic material so that a portion of heat generated by susceptor element 140 is generated based on magnetic hysteresis of the ferromagnetic material when an electromagnetic field having a frequency value in the range between 10 kHz to 10 MHz is received by susceptor element 140. In some non-limiting embodiments, control device 110 determines a predetermined configuration of susceptor element 140 that is associated with susceptor element 140 including an amount of ferromagnetic material so that a portion of heat generated by susceptor element 140 is generated based on magnetic hysteresis of the ferromagnetic material. In some non-limiting embodiments, control device 110 provides the alternating electrical current with the frequency value in the range between 10 kHz to 10 MHz based on determining that susceptor element 140 includes the predetermined configuration.

In some non-limiting embodiments, control device 110 provides an alternating electrical current with a frequency value in the range between 10 kHz to 100 GHz based on a configuration of susceptor element 140 that includes an amount of material, where the amount of material is such that a majority of heat generated by susceptor element 140 is generated based on resistive heating by eddy currents in the material. For example, control device 110 determines a predetermined configuration (e.g., a predetermined geometry, a predetermined type of one or more materials, and/or a predetermined amount of one or more materials) of susceptor element 140 that is associated with susceptor element 140 including an amount of material so that a majority of heat generated by susceptor element 140 is generated based on resistive heating by eddy currents in the material. In some non-limiting embodiments, control device 110 provides the alternating electrical current with the frequency value in the range between 10 kHz to 100 GHz based on determining that susceptor element 140 includes the predetermined configuration.

As further shown in FIG. 3B, at step 304B, method 300B includes determining a response of an induction heating circuit. For example, control device 110 determines the response of induction heating circuit 150 to a magnetic property of susceptor element 140. In some non-limiting embodiments, control device 110 determines an SRF value of induction heating circuit 150 as the response of induction heating circuit 150 to the magnetic property of susceptor element 140. In some non-limiting embodiments, control device 110 causes susceptor element 140 to generate heat based on susceptor element 140 receiving a first magnetic field from inductor element 120 of induction heating circuit 150. In some non-limiting embodiments, susceptor element 140 generates heat and/or produces a second magnetic field based on receiving the magnetic field from inductor element 120. In some non-limiting embodiments, inductor element 120 receives the second magnetic field produced by susceptor element 140 and the SRF value of induction heating circuit 150 changes from a first SRF value to a second SRF value based on inductor element 120 receiving the second magnetic field produced by susceptor element 140. Control device 110 determines the second SRF value of induction heating circuit 150 and/or a difference between the first SRF value and the second SRF value. In some non-limiting embodiments, control device 110 determines the SRF value of induction heating circuit 150 based on control device 110 causing susceptor element 140 to generate heat.

In some non-limiting embodiments, control device 110 determines a change in the magnetic property of susceptor element 140. For example, control device 110 determines a change in magnetization of susceptor element 140 and/or an amplitude of a magnetic field produced by susceptor element 140. In some examples, control device 110 determines the change in the magnetization of susceptor element 140 and/or an amplitude of a magnetic field produced by susceptor element 140 based on a change in temperature of susceptor element 140.

In some non-limiting embodiments, the SRF value of induction heating circuit 150 changes from a first SRF value based on susceptor element 140 not being near (e.g., being absent from) inductor element 120 to a second SRF value based on susceptor element 140 being near (e.g., being present to) inductor element 120. For example, the SRF value of induction heating circuit 150 is based on an inductance of inductor element 120. In some non-limiting embodiments, the inductance of inductor element 120 changes based on a magnetic field produced by susceptor element 140 when susceptor element 140 generates heat (e.g., generates heat based on electromagnetic energy provided to susceptor element 140 by inductor element 120). In some non-limiting embodiments, the SRF value of induction heating circuit 150 is a first SRF value when susceptor element 140 is not near inductor element 120 because a magnetic field produced by susceptor element 140 would not cause a change (e.g., a measurable change) in the inductance of inductor element 120. In some non-limiting embodiments, the SRF value of induction heating circuit 150 is a second SRF value when susceptor element 140 is near inductor element 120 because a magnetic field produced by susceptor element 140 causes a change in the inductance of inductor element 120. In some non-limiting embodiments, the second SRF value when susceptor element 140 is near inductor element 120 is an SRF value associated with susceptor element 140 being positioned within inductor element 120.

In some non-limiting embodiments, the SRF value of induction heating circuit 150 is a frequency value at which a maximum amount of electromagnetic energy is provided to susceptor element 140 by inductor element 120. In some non-limiting embodiments, the maximum amount of electromagnetic energy is provided to susceptor element 140 when an alternating electrical current of induction heating circuit 150 (e.g., the current through inductor element 120 of induction heating circuit 150) is at a maximum amplitude.

In some non-limiting embodiments, control device 110 determines the SRF value of induction heating circuit 150 when susceptor element 140 being within inductor element 120. For example, inductor element 120 includes an induction coil and at least a portion of susceptor element 140 (e.g., one quarter of a length of susceptor element 140, one half of a length of susceptor element 140, some of susceptor element 140, all of susceptor element 140, etc.) is positioned within (e.g., surrounded by) the induction coil. In some non-limiting embodiments, susceptor element 140 is positioned within a cartridge (e.g., a cartridge as disclosed herein) and the cartridge is positioned within inductor element 120. In some non-limiting embodiments, control device 110 determines the SRF value when susceptor element 140 (e.g., susceptor element 140 positioned within a cartridge) is positioned within inductor element 120.

In some non-limiting embodiments, control device 110 determines the SRF value of induction heating circuit 150 based on susceptor element 140 not being within inductor element 120. For example, inductor element 120 includes an induction coil and susceptor element 140 is positioned outside (e.g., no portion of susceptor element 140 is surrounded by) the induction coil. In some non-limiting embodiments, susceptor element 140 is positioned coaxially with the induction coil. Control device 110 determines the SRF value when susceptor element 140 (e.g., susceptor element 140 positioned within a cartridge) is not positioned within inductor element 120.

In some non-limiting embodiments, control device 110 determines the SRF value of induction heating circuit 150 based on a voltage across capacitor element 160 when an alternating electrical current having a predetermined frequency value (e.g., a drive frequency value) is provided to induction heating circuit 150. For example, control device 110 samples a voltage across capacitor element 160 and generates a voltage waveform based on the samples of the voltage. Control device 110 determines a phase (e.g., in degrees) of the voltage waveform and an amplitude of the voltage waveform at the predetermined frequency value of the alternating electrical current. Control device 110 determines the SRF value of induction heating circuit 150 based on the phase of the voltage waveform. In one example, control device 110 determines the SRF value of induction heating circuit 150 to be a frequency value at which a derivative (e.g., a rate of change) of the phase of the voltage waveform has a maximum value. In another example, control device 110 determines the SRF value of induction heating circuit 150 to be a frequency value at which the amplitude of the voltage waveform has a maximum value.

In some non-limiting embodiments, control device 110 determines the SRF value of induction heating circuit 150 based on a frequency value of an alternating electrical current in induction heating circuit 150. For example, control device 110 determines the frequency value of the alternating electrical current flowing in inductor element 120 and control device 110 determines the SRF value of induction heating circuit 150 based on the frequency value of the alternating electrical current. In some non-limiting embodiments, control device 110 determines the SRF value of induction heating circuit 150 based on a change in frequency value of the alternating electrical current in induction heating circuit 150. For example, control device 110 determines a first frequency value of the alternating electrical current flowing in inductor element 120 and control device 110 determines a second frequency value of the alternating electrical current flowing in inductor element 120. Control device 110 determines the change in frequency value of the alternating electrical current flowing based on a difference between the first frequency value and the second frequency value and control device 110 determines the SRF value of induction heating circuit 150 based on the change in frequency value of the alternating electrical current.

In some non-limiting embodiments, control device 110 determines the SRF value of induction heating circuit 150 based on an amplitude of an alternating electrical current in induction heating circuit 150. For example, control device 110 determines the amplitude of the alternating electrical current flowing in inductor element 120 and control device 110 determines the SRF value of induction heating circuit 150 based on the amplitude of the alternating electrical current. In some non-limiting embodiments, control device 110 determines the SRF value of induction heating circuit 150 based on a change in amplitude of the alternating electrical current in induction heating circuit 150. For example, control device 110 determines a first amplitude of the alternating electrical current flowing in inductor element 120 and control device 110 determines a second amplitude of the alternating electrical current flowing in inductor element 120. Control device 110 determines the change in amplitude of the alternating electrical current flowing based on a difference between the first amplitude and the second amplitude and control device 110 determines the SRF value of induction heating circuit 150 based on the change in amplitude of the alternating electrical current.

In some non-limiting embodiments, control device 110 determines the SRF value of induction heating circuit 150 based on a time interval. For example, control device 110 determines (e.g., continuously determine) the SRF value of induction heating circuit 150 at a time interval that is less than 2 seconds. In one example, control device 110 determines the SRF value of induction heating circuit 150 at a time interval that is equal to 0.1 second. In some non-limiting embodiments, control device 110 determines the SRF value of induction heating circuit 150 at a time interval that is in a milliseconds timescale. In one example, control device 110 determines the SRF value of induction heating circuit 150 at a time interval that is equal to 1 ms. In another example, control device 110 determines the SRF value of induction heating circuit 150 at a time interval that is equal to 2 ms.

In some non-limiting embodiments, control device 110 determines the SRF value of induction heating circuit 150 based on inductor element 120 and capacitor element 160. For example, control device 110 determines the SRF value of induction heating circuit 150 based on the equation:

$$SRF = \frac{1}{2\pi\sqrt{LC}}$$

where L is the inductance value of inductor element 120 and C is the capacitance value of capacitor element 160.

In some non-limiting embodiments, control device 110 determines the SRF value of induction heating circuit 150 based on a magnetic property of susceptor element 140. For example, control device 110 determines the SRF value of induction heating circuit 150 based on a magnetic field produced by susceptor element 140 that is received by inductor element 120. In some non-limiting embodiments, control device 110 causes inductor element 120 to produce a first magnetic field that is received by susceptor element 140. In some non-limiting embodiments, susceptor element 140 produces a second magnetic field based on receiving the first magnetic field from inductor element 120. In some non-limiting embodiments, inductor element 120 receives the second magnetic field from susceptor element 140 and the inductance of inductor element 120 changes based on the second magnetic field. Control device 110 determines the SRF value of induction heating circuit 150 based on the change in the inductance of inductor element 120. In some non-limiting embodiments, the second magnetic field includes a component of the first magnetic field that has a different frequency value than a frequency value of the first magnetic field.

In some non-limiting embodiments, control device 110 determines the SRF value of induction heating circuit 150 based on an input provided by control device 110 to induction heating circuit 150. In some non-limiting embodiments, the SRF value of induction heating circuit 150 is in a range between 100 kHz to 200 kHz based on a configuration of induction heating circuit 150 and susceptor element 140. In some non-limiting embodiments, control device 110 scans (e.g., provide an input current having a specific frequency value) a plurality of frequency values in a range between 100 kHz to 200 kHz. In some non-limiting embodiments, control device 110 scans 16 frequency values in the range between frequency values between 100 kHz to 200 kHz. In some non-limiting embodiments, control device 110 measures a time delay between an excitation of induction heating circuit 150 based on the input provided by control device 110 to induction heating circuit 150 (e.g., an alternating electrical current provided as an input to inductor element 120 of induction heating circuit 150) and a response from susceptor element 140 at each frequency value that is scanned. In some non-limiting embodiments, the excitation of induction heating circuit 150 and/or the response from susceptor element 140 is measured by control device 110 by measuring a voltage across capacitor element 160.

In some non-limiting embodiments, the time delay between excitation of induction heating circuit 150 based on the input provided by control device 110 and response from susceptor element 140 at each frequency value that is scanned is determined to be a measure of the phase of induction heating circuit 150 versus excitation at each frequency value that is scanned. Control device 110 determines a numerical derivative of the phase of induction heating circuit 150 and control device 110 determines a maximum value of the numerical derivative (e.g., a frequency value for induction heating circuit 150 at which the phase is equal to 90 degrees) as a value (e.g., an initial estimated value) of the SRF value of induction heating circuit 150.

In some non-limiting embodiments, control device 110 again scans frequency values (e.g., 16 frequency values) in a smaller range of frequency values between 100 kHz to 200 kHz than the initial scan and determine a derivative of the phase to determine a second value (e.g., an updated estimated value) of the SRF value of induction heating circuit 150. In some non-limiting embodiments, control device 110 determines the first value and the second value of the SRF value of induction heating circuit 150 in less than a quarter of a second.

In some non-limiting embodiments, control device 110 determines the SRF value of induction heating circuit 150 based on an initial estimated value of the SRF value of induction heating circuit 150. For example, control device 110 determines the initial estimated value of the SRF value of induction heating circuit 150 as described above. In some non-limiting embodiments, a desired power level to be output by induction heating circuit 150 is set by control device 110 based on control device 110 controlling a voltage that excites the half bridge. In some non-limiting embodiments, the voltage is controlled by a pulse width modulated signal provided by control device 110. In some non-limiting embodiments, once the desired power level is set, control device 110 continuously provides an alternating electrical current as an input to induction heating circuit 150 at a plurality of different frequency values. In some non-limiting embodiments, the plurality of frequency values includes 4 frequency values that are within a predetermined amount of and above the initial estimated value of the SRF value, and that have a period that is an integer number of clock cycles of a clock of control device 110. In some non-limiting embodiments, at each frequency value of the plurality of frequency values, control device 110 measures a time delay between the excitation of induction heating circuit 150 and the response from susceptor element 140, the time delay is measured by control device 110 and converted to a phase in degrees. In some non-limiting embodiments, the excitation is measured based on a driving square wave provided as an input current to induction heating circuit 150 (e.g., an input current provided to inductor element 120) and the response is measured based on a voltage response of induction heating circuit 150 (e.g., a voltage across capacitor element 160). In some non-limiting embodiments, control device 110 determines the SRF value by extrapolating a linear fit to the plurality of frequency values (e.g., the 4 frequency values) to the phase value at resonance that occurs at the SRF. Additionally or alternatively, control device 110 determines the SRF value by determining a derivative of a line formed by the plurality of frequency values (e.g., a derivative of the phase corresponding to the plurality of frequency values), where the SRF value is equal to the frequency value corresponding to a maximum of the derivative of the line.

In some non-limiting embodiments, as the temperature of susceptor element 140 changes, the magnetic susceptibility of susceptor element 140 changes based on the temperature change of susceptor element 140 or vice versa. In some non-limiting embodiments, the change of the magnetic susceptibility of susceptor element 140 causes a change in the inductance of inductor element 120 that is near susceptor element 140 and the change in the inductance of inductor element 120 causes a change in the SRF value of induction heating circuit 150.

In some non-limiting embodiments, once control device 110 determines the SRF value, control device 110 continuously scans through the plurality of frequency values and determines an updated value of the SRF value based on the plurality of frequency values. In some non-limiting embodiments, control device 110 determines a value of the SRF value of induction heating circuit 150 and control device 110 provides an alternating electrical current at the plurality of frequency values as an input to induction heating circuit 150. In some non-limiting embodiments, control device 110 determines that one or more frequency values of the plurality of frequency values correspond to a relative phase value (e.g., a phase value that is the difference between the driving phase and the measured phase) that is below 90 degrees. In some non-limiting embodiments, control device 110 changes the plurality of frequency values based on determining that one or more frequency values of the plurality of frequency values correspond to a relative phase value that is below 90 degrees. In some non-limiting embodiments, control device 110 changes the plurality of frequency values so that all of the plurality of frequency values correspond to a relative phase value that is above 90 degrees. In the example above, control device 110 determines the SRF value of induction heating circuit 150 to be a frequency value that is within a predetermined frequency range between the frequency value of the plurality of frequency values that corresponds to a phase value that is closest to a 90 degree phase. In some non-limiting embodiments, control device 110 determines the SRF value of induction heating circuit 150 to be a frequency value that is between a frequency value of the plurality of frequency values that corresponds to a phase value that is below a phase value equal to 90 degrees and a frequency value of the plurality of frequency values that corresponds to a phase value that is above a phase value equal to 90 degrees (e.g., a phase that is above a phase value equal to 90 degrees and closest to 90 degrees).

In some non-limiting embodiments, control device 110 changes the plurality of frequency values so that the plurality of frequency values remain close to (e.g., within a predetermined value of) but above the SRF value. In this way, control device 110 allows induction heating circuit 150 to operate close to the SRF value of induction heating circuit 150, which is more efficient than induction heating circuit 150 operating outside (e.g., outside a range between frequency values close to) the SRF value of induction heating circuit 150, while still being able to measure how the SRF value changes based on a temperature change of susceptor element 140.

In some non-limiting embodiments, control device 110 determines whether susceptor element 140 is near induction heating circuit 150 (e.g., inductor element 120 of induction heating circuit 150). For example, control device 110 determines whether susceptor element 140 is near induction heating circuit 150 based on an SRF value of induction heating circuit 150. In this way, a device that includes system 100 (e.g., control device 110 of system 100) allows a user of the device to determine whether susceptor element 140 is near induction heating circuit 150 of system 100 without having to open a housing of the device.

In some non-limiting embodiments, control device 110 determines the SRF value of induction heating circuit 150 and control device 110 compares the SRF value of induction heating circuit 150 to a frequency value (e.g., a threshold value of frequency) associated with susceptor element 140. In some non-limiting embodiments, the frequency value is a predetermined frequency value associated with susceptor element 140 or a measurement (e.g., a previous measurement) of the SRF value of induction heating circuit 150 when susceptor element 140 is near induction heating circuit 150. If control device 110 determines that the SRF value of induction heating circuit 150 corresponds to (e.g., matches, is within a predetermined threshold value of, etc.) the frequency value, control device 110 determines that susceptor element 140 is near induction heating circuit 150. If control device 110 determines that the SRF value of induction heating circuit 150 does not correspond to the frequency value, control device 110 determines that susceptor element 140 is not near induction heating circuit 150.

In some non-limiting embodiments, the predetermined frequency value is a measurement of the SRF value of induction heating circuit 150 when susceptor element 140 is not near induction heating circuit 150. In some non-limiting embodiments, if control device 110 determines that the SRF value of induction heating circuit 150 corresponds to the frequency value, control device 110 determines that susceptor element 140 is not near induction heating circuit 150. If control device 110 determines that the SRF value of induction heating circuit 150 does not correspond to the frequency value, control device 110 determines that susceptor element 140 is near induction heating circuit 150.

In some non-limiting embodiments, control device 110 determines whether a susceptor element (e.g., susceptor element 140) that has a specific configuration (e.g., a configuration for a heating a specific vaporizable substance, a standard configuration for use in a specific electronic vaporizer, a configuration that indicates a property of susceptor element 140, a configuration that indicates a property of a vaporizable substance associated with susceptor element 140, and/or the like) is near induction heating circuit 150 (e.g., inductor element 120 of induction heating circuit 150) based on an SRF value of induction heating circuit 150. In this way, a device that includes system 100 (e.g., control device 110 of system 100) may allow a user of the device to determine whether susceptor element 140 with a specific configuration is near induction heating circuit 150 of system 100 without having to open a housing of the device.

In some non-limiting embodiments, control device 110 determines the SRF value of induction heating circuit 150. In some non-limiting embodiments, control device 110 compares the SRF value of induction heating circuit 150 to a frequency value, where the frequency value is a predetermined frequency value or a measurement (e.g., a previous measurement) of the SRF value of induction heating circuit 150 when susceptor element 140 having the specific configuration is near induction heating circuit 150. If control device 110 determines that the SRF value of induction heating circuit 150 corresponds to the predetermined frequency value, control device 110 determines that susceptor element 140 with the specific configuration is near induction heating circuit 150. If control device 110 determines that the SRF value of induction heating circuit 150 does not correspond to the frequency value, control device 110 determines that susceptor element 140 with the specific configuration is not near induction heating circuit 150.

In some non-limiting embodiments, control device 110 performs an action based on determining that a SRF value of induction heating circuit 150 does not correspond to a frequency value associated with susceptor element 140. For example, control device 110 determines the SRF value of induction heating circuit 150. Control device 110 determines that a susceptor element is within proximity of induction heating circuit 150 based on the SRF value of induction heating circuit 150 and control device 110 determines that the susceptor element does not have a specific configuration associated with susceptor element 140 based on the SRF value of induction heating circuit 150. In some non-limiting embodiments, control device 110 determines that the susceptor element does not have the specific configuration based on comparing the SRF value of induction heating circuit 150 to a predetermined frequency value associated with susceptor element 140. In some non-limiting embodiments, control device 110 determines that the SRF value of induction heating circuit 150 does not correspond to a frequency value associated with susceptor element 140. In some non-limiting embodiments, control device 110 performs the action based on determining that the SRF value of induction heating circuit 150 does not correspond to the frequency value associated with susceptor element 140. In another example, control device 110 determines the SRF value of induction heating circuit 150 and control device 110 determines that a susceptor element (e.g., susceptor element 140) is not within proximity of induction heating circuit 150 based on the SRF value of induction heating circuit 150. In some non-limiting embodiments, control device 110 performs the action based on determining that a susceptor element is not within proximity of induction heating circuit 150.

In some non-limiting embodiments, control device 110 causes an indication of a warning to be displayed based on determining that the SRF value of induction heating circuit 150 does not correspond to the frequency value associated with susceptor element 140 and/or based on determining that a susceptor element is not within proximity of induction heating circuit 150. For example, control device 110 determines that the SRF value of induction heating circuit 150 does not correspond to the frequency value associated with susceptor element 140 and control device 110 generates a signal that causes a component (e.g., a component of a vaporizer device, such as a warning light) to display the indication of a warning. In some non-limiting embodiments, control device 110 determines that a susceptor element is not within proximity of induction heating circuit 150 and control device 110 generates a signal that causes a component to display the indication of a warning. In some non-limiting embodiments, a component of a vaporizer device (e.g., a vaporizer device as disclosed herein) displays the indication of a warning. For example, the component of the vaporizer device displays the indication of a warning based on receiving the signal that causes the component to display the indication of a warning from control device 110.

In some non-limiting embodiments, control device 110 disables induction heating circuit 150 based on determining that the SRF value of induction heating circuit 150 does not correspond to the frequency value associated with susceptor element 140 and/or based on determining that a susceptor element is not within proximity of induction heating circuit 150. For example, control device 110 determines that the SRF value of induction heating circuit 150 does not correspond to the frequency value associated with susceptor element 140 and control device 110 foregoes providing power to induction heating circuit 150. In another example, control device 110 determines that a susceptor element is not within proximity of induction heating circuit 150 and control device 110 foregoes providing power to induction heating circuit 150.

As further shown in FIG. 3B, at step 306B, method 300B includes determining a characteristic of the susceptor element. For example, control device 110 determines the characteristic of susceptor element 140 based on a response of induction heating circuit 150 to a magnetic property of susceptor element 140. In some non-limiting embodiments, control device 110 determines the characteristic of susceptor element 140 based on the SRF value of induction heating circuit 150. For example, control device 110 determines a characteristic of susceptor element 140 that corresponds to an SRF value of induction heating circuit 150. In some non-limiting embodiments, control device 110 determines the characteristic of susceptor element 140 based on the SRF value of induction heating circuit 150 and a measurement of amplitude of an electrical characteristic of induction heating circuit 150. In some non-limiting embodiments, the electrical characteristic of induction heating circuit 150 includes an alternating electrical current provided to induction heating circuit 150 (e.g., an alternating electrical current provided to inductor element 120 of induction heating circuit 150), a magnetic field produced by inductor element 120, and/or a voltage across capacitor element 160.

In some non-limiting embodiments, control device 110 determines the characteristic of susceptor element 140 based on a magnetic field produced by inductor element 120 and the SRF value of induction heating circuit 150. For example, control device 110 determines an amplitude of the magnetic field produced by inductor element 120 and the SRF value of induction heating circuit 150. Control device 110 determines a temperature curve that corresponds to the amplitude of the magnetic field produced by inductor element 120 and the SRF value of induction heating circuit 150, where the temperature curve indicates a temperature of susceptor element 140.

In some non-limiting embodiments, control device 110 determines a first SRF value of induction heating circuit 150 when susceptor element 140 is heated by inductor element 120 based on a first magnetic field produced by inductor element 120. In some non-limiting embodiments, control device 110 determines a second SRF value of induction heating circuit 150 when susceptor element 140 is heated by induction heating circuit 150 based on a second magnetic field produced by inductor element 120. In some non-limiting embodiments, control device 110 compares the first SRF value and the second SRF value to determine the temperature of susceptor element 140 based on a change in the SRF value of induction heating circuit 150 from the first SRF value to the second SRF value.

In some non-limiting embodiments, control device 110 determines a change of temperature that corresponds to changes in the SRF value of induction heating circuit 150. In some non-limiting embodiments, control device 110 receives a calibration for susceptor element 140 based on simultaneously measuring the SRF value of induction heating circuit 150 and the temperature of susceptor element 140 by an independent temperature sensing device (e.g., an infra-red thermometer). In some non-limiting embodiments, control device 110 determines the temperature of susceptor element 140 based on the calibration for susceptor element 140 and the SRF value of induction heating circuit 150. In some non-limiting embodiments, control device 110 receives a calibration for susceptor element 140 based on determining a first SRF value of induction heating circuit 150 at a first temperature of susceptor element 140 (e.g., at ambient temperature of susceptor element 140) and then determining a second SRF value of induction heating circuit 150 at the Curie temperature of susceptor element 140. In some non-limiting embodiments, the second SRF value of induction heating circuit 150 at the Curie temperature of susceptor element 140 is determined based on determining when the spontaneous magnetization of susceptor element 140 changes to zero (e.g., at the Curie temperature). In some non-limiting embodiments, control device 110 determines the temperature of susceptor element 140 at a temperature between the first temperature and the Curie temperature of susceptor element 140 based on the SRF value of induction heating circuit 150.

In some non-limiting embodiments, control device 110 determines a temperature of susceptor element 140 based on a change in a magnetic property of susceptor element 140. For example, control device 110 determines the temperature of susceptor element 140 based on a change in magnetization of susceptor element 140 and/or an amplitude of a magnetic field produced by susceptor element 140. In some non-limiting embodiments, the change in magnetization of susceptor element 140 and/or the amplitude of the magnetic field produced by susceptor element 140 corresponds to a change in temperature of susceptor element 140 and control device 110 determines a value of a change in temperature of susceptor element 140 based on determining a value of change in magnetization of susceptor element 140 and/or the amplitude of the magnetic field produced by susceptor element 140.

In some non-limiting embodiments, control device 110 causes susceptor element 140 to change from the first temperature to a second temperature. For example, control device 110 determines the first temperature of susceptor element 140. In some non-limiting embodiments, control device 110 causes the temperature of susceptor element 140 to change from the first temperature to the second temperature based on determining that the first temperature did not satisfy a threshold value of temperature. In some non-limiting embodiments, control device 110 causes susceptor element 140 to change from the first temperature to the second temperature based on adjusting an amount of alternating electrical current in induction heating circuit 150. For example, control device 110 causes susceptor element 140 to change from the first temperature to the second temperature based on control device 110 adjusting an amount of alternating electrical current provided to induction heating circuit 150.

In some non-limiting embodiments, control device 110 implements one or more control loop algorithms to measure the temperature of susceptor element 140 and keep the temperature of susceptor element 140 at a desired temperature value or within a desired range between temperature values.

In some non-limiting embodiments, control device 110 controls a temperature of susceptor element 140 based on a calibration measurement. For example, a plurality of curves of SRF values of induction heating circuit 150 and corresponding amplitude values of an alternating electrical current are provided as an input to induction heating circuit 150 for a predetermined temperature (e.g., room temperature or 20° C.) of susceptor element 140 as the calibration measurement. Then during operation of induction heating circuit 150, control device 110 determines a plurality of curves of SRF values of induction heating circuit 150 and corresponding amplitude values of an alternating electrical current at each temperature of a plurality of temperatures of susceptor element 140. In some non-limiting embodiments, control device 110 divides the plurality of curves by the calibration measurement to provide a plurality of linear plots that are compensated for based on the alternating electrical current. In some non-limiting embodiments, control device 110 determines the temperature of susceptor element 140 based on the plurality of linear plots. In some non-limiting embodiments, control device 110 determines the temperature of susceptor element 140 based on the plurality of linear plots using a proportional-integral-derivative (PID) controller. In some non-limiting embodiments, control device 110 controls the temperature of susceptor element 140 by adjusting the temperature of susceptor element 140 based on determining the temperature of susceptor element 140. In some non-limiting embodiments, control device 110 determines the temperature of susceptor element 140 for each of a plurality of SRF values of induction heating circuit 150 that correspond to a plurality of predetermined amplitudes of alternating electrical current provided as an input to induction heating circuit 150. In some non-limiting embodiments, control device 110 measures an amplitude of the voltage across capacitor element 160 and determines a present amplitude of the alternating electrical current provided as an input to induction heating circuit 150. Control device 110 determines a first temperature of susceptor element 140 based on the present amplitude. After determining the first temperature, control device 110 determines a predetermined amplitude of the plurality of predetermined amplitudes of alternating electrical current that is closest to the present amplitude. In some non-limiting embodiments, control device 110 determines the SRF value of induction heating circuit 150 and determines the second temperature of susceptor element 140 that corresponds to the predetermined amplitude that is closest to the present amplitude. In some non-limiting embodiments, control device 110 compares the first temperature and the second temperature and determines an amplitude of (e.g., an amperage of) alternating electrical current to provide or remove as an input to induction heating circuit 150. In some non-limiting embodiments, control device 110 provides or removes the amplitude of alternating electrical current as an input to induction heating circuit 150 based on determining the amplitude.

In some non-limiting embodiments, to increase the temperature of (e.g., heat up) susceptor element 140 to a desired temperature in a short duration of time, control device 110 estimates an alternating electrical current (e.g., an alternating electrical current that causes a heat pulse in susceptor element 140) for a desired gain in temperature of susceptor element 140 based on a calibration of induction heating circuit 150. In some non-limiting embodiments, control device 110 provides the alternating electrical current to inductor element 120 to operate inductor element 120 at a maximum power for a short duration of time.

Figure 3C:
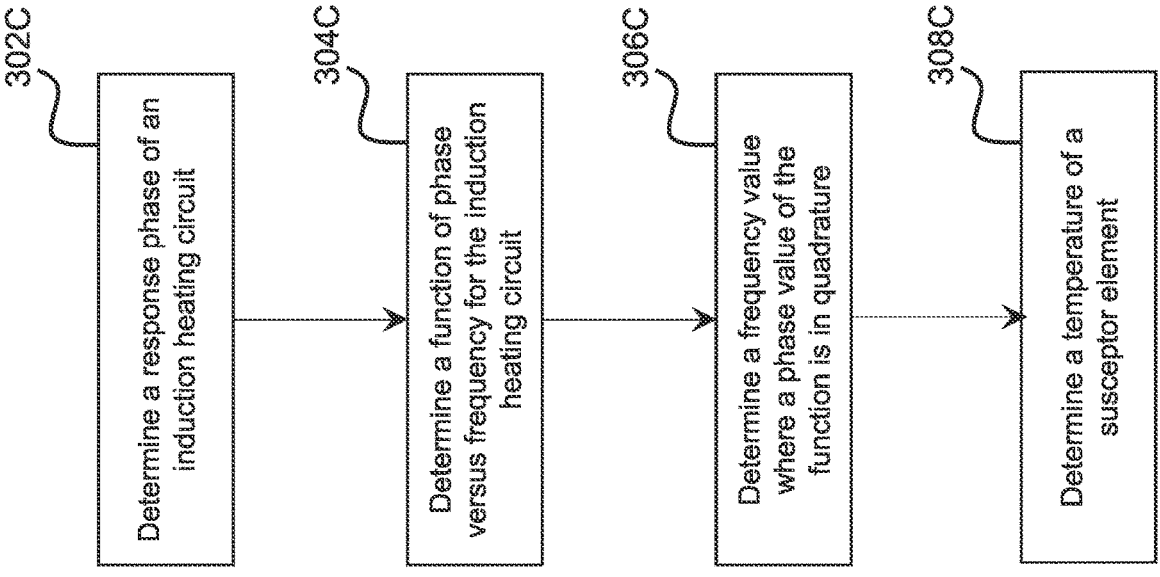
FIG. 3C is a flowchart of a non-limiting embodiment of a method for determining a temperature of a susceptor element.

Referring now to FIG. 3C, FIG. 3C is a flowchart of a non-limiting embodiment of a method 300C for determining a characteristic, such as temperature, of a susceptor element (e.g., susceptor element 140) in a system, such as an induction heating system. In some non-limiting embodiments, one or more of the steps of method 300C are performed (e.g., completely, partially, etc.) by control device 110. In some non-limiting embodiments, one or more of the steps of method 300C are performed by another device or a group of devices separate from or including control device 110. For example, an additional control device separate from control device 110.

As shown in FIG. 3C, at step 302C, method 300C includes determining a response phase of an induction heating circuit. For example, control device 110 determines a first response phase of an induction heating circuit. In some non-limiting embodiments, the first response phase is based on a magnetic property of susceptor element 140 at a first driving frequency. In some non-limiting embodiments, the first response phase includes a value of a phase difference between a phase of a driving current at the first driving frequency and a phase of a voltage across an electrical component (e.g., inductor element 120, capacitor element 160, etc.) of induction heating circuit 150 (e.g., a voltage response of induction heating circuit 150) at the first driving frequency.

In some non-limiting embodiments, control device 110 determines the phase of the voltage across the electrical component of induction heating circuit 150. For example, control device 110 may determine the phase of the voltage across the electrical component of induction heating circuit 150 at the second driving frequency. In some non-limiting embodiments, control device 110 may determine the phase of the voltage across the electrical component of induction heating circuit 150 at the second driving frequency based on a second measurement of voltage across capacitor element 160.

In some non-limiting embodiments, control device 110 determines a second response phase of induction heating circuit 150. For example, control device 110 determines a second response phase of induction heating circuit 150. In some non-limiting embodiments, the second response phase is based on a magnetic property of susceptor element 140 at a second driving frequency. In some non-limiting embodiments, the second response phase includes a value of a phase difference between a phase of a driving current at the second driving frequency and a phase of a voltage across an electrical component of induction heating circuit 150 at the second driving frequency.

As shown in FIG. 3C, at step 304C, method 300C includes determining a function of phase versus frequency for induction heating circuit 150. For example, control device 110 may determine a function of phase versus frequency for induction heating circuit 150. In some non-limiting embodiments, control device 110 may determine the function of phase versus frequency for induction heating circuit 150 based on the first response phase and the second response phase. In some non-limiting embodiments, control device 110 determines polynomial coefficients of a polynomial that is fit to the first response phase of induction heating circuit 150 and the second response phase of induction heating circuit 150. In some non-limiting embodiments, control device 110 may determine the frequency value where the phase value of the function is in quadrature. For example, control device 110 may determine the frequency value where the phase value of the function is in quadrature based on the polynomial coefficients of the polynomial.

In some non-limiting embodiments, control device 110 may determine a third response phase of induction heating circuit 150. For example, control device 110 may determine a third response phase of induction heating circuit 150, where the third response phase is based on a magnetic property of susceptor element 140 at a third driving frequency. In some non-limiting embodiments, the third response phase may include a value of phase difference between a phase of a driving current at the third driving frequency and a phase of a voltage across the electrical component of induction heating circuit 150 at the third driving frequency. In some non-limiting embodiments, control device 110 may determine a fourth response phase of induction heating circuit 150. For example, control device 110 may determine a fourth response phase of induction heating circuit 150, where the fourth response phase is based on a magnetic property of susceptor element 140 at a fourth driving frequency. In some non-limiting embodiments, the fourth response phase is a value of phase difference between a phase of a driving current at the fourth driving frequency and a phase of a voltage across the electrical component of induction heating circuit 150 at the fourth driving frequency. In some non-limiting embodiments, control device 110 may determine the function of phase versus frequency for induction heating circuit 150 based on the first response phase, the second response phase, the third response phase, and/or the fourth response phase.

In some non-limiting embodiments, the function may include a polynomial. In some non-limiting embodiments, control device 110 may determine polynomial coefficients of the polynomial that is fit to the first response phase of induction heating circuit 150, the second response phase of induction heating circuit 150, the third response phase of induction heating circuit 150, and/or the fourth response phase of induction heating circuit 150. In some non-limiting embodiments, control device 110 may determine the frequency value where the phase value of the function is in quadrature based on the polynomial coefficients of the polynomial.

As shown in FIG. 3C, at step 306C, method 300C includes determining a frequency value where a phase value of the function is in quadrature. For example, control device 110 may determine a frequency value where a phase value of the function is in quadrature. In some non-limiting embodiments, control device 110 may determine a frequency value where a phase value of the function is in quadrature based on the function of phase versus frequency.

In some non-limiting embodiments, control device 110 determines a function of phase versus frequency for induction heating circuit 150 by determining a slope of a line that includes the function of phase vs. frequency, wherein the line is based on the first response phase and the second response phase. In some non-limiting embodiments, control device 110 determines the frequency value where a phase value of the function is in quadrature based on the slope.

As shown in FIG. 3C, at step 308C, method 300C includes determining a temperature of a susceptor element. For example, control device 110 may determine a temperature of a susceptor element. In some non-limiting embodiments, control device 110 may determine a temperature of susceptor element 140 based on the frequency value. In some non-limiting embodiments, control device 110 determines the temperature of susceptor element 140 based on a measurement of a magnetic field. For example, control device 110 determines the temperature of susceptor element 140 based on a measurement of a magnetic field generated by inductor element 120. Additionally, or alternatively, control device 110 determines the temperature of susceptor element 140 based on a measurement of a magnetic field generated by inductor element 120 and the frequency value where the phase value of the function is in quadrature.

In some non-limiting embodiments, control device 110 determines a measurement of a magnetic field. For example, control device 110 may determine a measurement of a magnetic field generated by inductor element 120. In some non-limiting embodiments, control device 110 may determine the temperature of susceptor element 140 based on the measurement of the magnetic field. For example, control device 110 may determine the temperature of susceptor element 140 based on the measurement of the magnetic field generated by inductor element 120. Additionally, or alternatively, control device 110 may determine the temperature of susceptor element 140 based on the frequency value where the phase value of the function is in quadrature. For example, control device 110 may determine the temperature of susceptor element 140 based on the measurement of the magnetic field generated by inductor element 120 and the frequency value where the phase value of the function is in quadrature. In some non-limiting embodiments, control device 110 may determine a measurement of a magnetic field generated by inductor element 120 based on a measurement of an amplitude of an A/C voltage across capacitor element 160 and a frequency of the AC voltage across capacitor element 160. In some non-limiting embodiments, control device 110 may determine the temperature of susceptor element 140 based on the measurement of the magnetic field generated by inductor element 120 and the frequency value where the phase value of the function is in quadrature.

In some non-limiting embodiments, control device 110 determines an amplitude of an A/C voltage across capacitor element 160 and a frequency of the A/C voltage across capacitor element 160. In some non-limiting embodiments, control device 110 determines a measurement of a magnetic field generated by inductor element 120 based on the amplitude of an A/C voltage across capacitor element 160 and the frequency of the A/C voltage across capacitor element 160. In some non-limiting embodiments, control device 110 determines the temperature of susceptor element 140 based on the measurement of the magnetic field generated by inductor element 120 and the frequency value where the phase value of the function is in quadrature.

In some non-limiting embodiments, control device 110 determines the temperature of susceptor element 140 based on the frequency value where the phase value of the function is in quadrature and an output of the at least one temperature sensor. In some non-limiting embodiments, the at least one temperature sensor is in thermal contact (e.g., physical contact by which a transfer of heat can occur according to conduction) with at least one of inductor element 120, capacitor element 160, or any combination thereof. In some non-limiting embodiments, control device 110 determines the temperature of susceptor element 140 based on the frequency value where the phase value of the function is in quadrature and an output of the at least one temperature sensor. In some non-limiting embodiments, the at least one temperature sensor is coupled to (e.g., in proximity to such that temperature sensor can sense an environment of) or in thermal contact with a component of the system. In some non-limiting embodiments, control device 110 determines the temperature of susceptor element 140 based on the frequency value where the phase value of the function is in quadrature and a temperature of an inductor element, a capacitor element, or any combination thereof. In some non-limiting embodiments, control device 110 determines the temperature of susceptor element 140 based on an amount of power absorbed by susceptor element 140. In some non-limiting embodiments, control device 110 determines an amount of power absorbed by susceptor element 140 based on the function of phase versus frequency.

In some non-limiting embodiments, control device 110 may determine the amount of power absorbed by susceptor element 140 based on a slope of a function associated with a phase difference between a driving A/C current and a voltage across an electrical component (e.g., inductor element 120, capacitor element 160, etc.) of induction heating circuit 150. For example, control device 110 may determine the amount of power absorbed by susceptor element 140 based on a slope of a function associated with a phase difference between a driving A/C current (I(t)) and a voltage response associated with (e.g., evaluated at) a frequency where the phase difference between the phase of the driving A/C current (I(t)) and the phase of the voltage across the electrical component of induction heating circuit 150 are in quadrature. In such an example, control device 110 may determine the amount of power absorbed by susceptor element 140 based on control device 110 determining a result of a formula such as formula (1):

$$1/I(\omega_0^2 RC) \tag{1}$$

where $\omega_0$ is the frequency at which the driving A/C current and the voltage response are in quadrature, C is the capacitance in the induction heating system, and P is an effective resistance such that $I(t)^2 R$ is the instantaneous power (instantaneous as opposed to time averaged) dissipated as heat in the induction heating system. The power absorbed by susceptor element 140 may therefore be obtained from the difference between the value of R as obtained from formula (1) with a susceptor element present (e.g., in proximity to an induction heating circuit, in proximity to an inductor element of an induction heating circuit) and the value of R obtained from formula (1) with no susceptor element present. The value of R with no susceptor element can be obtained once during fabrication of one or more components of system 100. Additionally, or alternatively, the value of R with no susceptor element can be updated (e.g., corrected) based on the temperature of one or more components of the induction heating system where the components of the induction heating system are at a different temperature from when the value of R with no susceptor was measured for the device.

Referring now to FIGS. 4A-4C, FIGS. 4A-4C are diagrams of a non-limiting embodiment of vaporizer device 400 that includes a system, such as system 100, for determining a characteristic of a susceptor element. FIGS. 4A and 4B show assembled views of vaporizer device 400, and FIG. 4C shows a disassembled view of vaporizer device 400. As shown in FIG. 4A, vaporizer device 400 includes housing 402. For the purpose of illustration, FIG. 4B shows vaporizer device 400 with housing 402 being transparent. As shown in FIG. 4B, vaporizer device 400 includes induction heating assembly 420, housing 402, power source 416, and tube 444. As shown in FIG. 4C, vaporizer device 400 includes electronic control components 436, at least one activation button 438, induction heating assembly 420, cartridge 418, housing 402, power source 416, valve 442, tube 444, and mouthpiece component 446. In some non-limiting embodiments, electronic control components 436 include control device 110 or electronic control components 436 are the same as or substantially similar to control device 110.

In some non-limiting embodiments, induction heating assembly 420 includes chassis 448 (e.g., an internal frame to support components of induction heating assembly 420), inductor element 406, capacitor element 414, and/or heating element body 440. In some non-limiting embodiments, inductor element 406 and capacitor element 414 are electrically connected (e.g., in a parallel electrical connection) to provide an induction heating circuit. In some non-limiting embodiments, inductor element 406 is the same as or substantially similar to inductor element 120. In some non-limiting embodiments, capacitor element 414 is the same as or substantially similar to capacitor element 160.

In some non-limiting embodiments, heating element body 440 is sized and/or configured to hold inductor element 406 when inductor element 406 is positioned within heating element body 440. Additionally or alternatively, chassis 448 is sized and/or configured to hold inductor element 406 and heating element body 440 near electronic control components 436, which may allow for compact size and control of inductor element 406 with electronic control components 436. Additionally or alternatively, heating element body 440 acts as an insulator to the heat generated by induction heating of a susceptor element within cartridge 418 and also shields electronic components from radiation of electromagnetic energy generated by inductor element 406.

In some non-limiting embodiments, cartridge 418 is sized and/or configured to fit within inductor element 406, which may allow for compact construction of the vaporizer device 400. In some non-limiting embodiments, cartridge 418 has an aperture in one end that allows the vapor from the vaporizable substance to flow out of cartridge 418. In some non-limiting embodiments, cartridge 418 includes a reservoir and the reservoir is sized and/or configured to hold a vaporizable substance. In some non-limiting embodiments, a susceptor element is sized and/or configured to be contained within the reservoir, and susceptor element 140 contacts the vaporizable substance of the reservoir. In some non-limiting embodiments, inductor element 406 is sized and/or configured to be housed within heating element body 440. In some non-limiting embodiments, inductor element 406 is electromagnetically coupled (e.g., inductively coupled, magnetically coupled, etc.) to a susceptor element within cartridge 418 and susceptor element 140 generates heat based on electromagnetic induction (e.g., by eddy currents generated in susceptor element 140 and/or by magnetic hysteresis generated in susceptor element 140).

In some non-limiting embodiments, cartridge 418 is a replaceable and/or disposable container that is a component of vaporizer device 400. For example, cartridge 418 contains a predetermined amount of a vaporizable substance, and when the vaporizable is used up or near to be used up, a user may replace cartridge 418 with another cartridge 418.

In some non-limiting embodiments, a vaporizable substance includes a composition, material, or matter that produces a vapor for inhalation by a human being when heated to a predetermined temperature. In some non-limiting embodiments, vaporizer device 400 includes an indicator of the amount of vaporizable substance remaining in cartridge 418. In some non-limiting embodiments, the indicator is positioned on cartridge 418 and/or on the housing of vaporizer device 400. In some non-limiting embodiments, the indicator includes a display screen, such as a digital or analog output screen on vaporizer device 400 that is visible to a user. In some non-limiting embodiments, vaporizer device 400 has a second indicator that indicates when cartridge 418 is close to empty and acts as a low volume indicator for the vaporizable substance.

In some non-limiting embodiments, cartridge 418 is configured to be refilled with a vaporizable substance. Additionally or alternatively, cartridge 418 is configured to be refilled while positioned within vaporizer device 400 such as through a vent or aperture in housing 402. In some non-limiting embodiments, inductor element 406 is constructed as part of a cartridge structure, which includes cartridge 418, a susceptor element, and inductor element 406, such that the cartridge structure is replaceable. In some non-limiting embodiments, the cartridge structure (e.g., the replaceable cartridge structure) includes electrical connections (e.g., electrical contacts) so that inductor element 406 electrically connects to electronic control components 436 when the replaceable cartridge structure is positioned within vaporizer device 400.

In some non-limiting embodiments, replacement of cartridge 418 is accomplished by removing housing 402 and separating any additional components as desired. In some non-limiting embodiments, replacement of cartridge 418 is accomplished without removal of housing 402. In some non-limiting embodiments, vaporizer device 400 allows a user to remove cartridge 418 when cartridge 418 is empty and to replace cartridge 418 with a new, full cartridge 418 within induction heating assembly 420 without removing any other components of induction heating assembly 420. In some non-limiting embodiments, vaporizer device 400 includes a channel or chamber defined therein that allows for removal of an empty or near empty cartridge 418 and accepts a replacement cartridge 418. In some non-limiting embodiments, vaporizer device 400 includes a chamber or channel that is able to be manipulated (e.g., folded, twisted, and/or the like) to open to accept a new cartridge 418 and then able to be manipulated to close and place cartridge 418 in the appropriate position (e.g., to enable heating of the vaporizable substance within cartridge 418). In some non-limiting embodiments, housing 402 has a chamber or channel defined therein, and housing 402 is configured to receive cartridge 418 within the chamber or channel.

In some non-limiting embodiments, a susceptor element is positioned within cartridge 418 and susceptor element 140 is heated via induction without electrical connections to power source 410. Additionally or alternatively, cartridge 418 includes a body having an inside surface and susceptor element 140 is positioned adjacent to the inside surface of cartridge 418. Additionally or alternatively, the body and/or a neck of cartridge 418 acts as an insulating member between susceptor element 140 and the induction heating assembly 420. In some non-limiting embodiments, the insulating member removes (e.g., separates) the induction heating assembly 420 from contact with the vaporizable substance (e.g., a liquid) in cartridge 418. In some non-limiting embodiments, cartridge 418 is constructed of an appropriate insulating material, including but not limited to, glass, fiberglass, ceramic, and/or the like. In some non-limiting embodiments, an open end of cartridge 418 defines an air path through vaporizer device 400.

In some non-limiting embodiments, activation button 438 is configured to protrude through an aperture in housing 402 so that a user is able to activate vaporizer device 400. Additionally or alternatively, activation button 438 is configured such that a depression of a physical button is not necessary. In some non-limiting embodiments, activation button 438 includes a touchscreen component, such as a capacitive touchscreen. Additionally or alternatively, using such a touch screen, a user is able to use vaporizer device 400 to review and/or verify information such as age, number of uses, and other analytics. Additionally or alternatively, such touchscreen capability is combined with onboard sensors to thereby form a smart vaporizer, which are capable of being connected for communication and networked to local computers or the internet.

In some non-limiting embodiments, activation button 438 is integrated with another aspect and/or component of vaporizer device 400. In some non-limiting embodiments, activation button 438 is integrated with mouthpiece component 446. In some non-limiting embodiments, contact with a user's mouth to mouthpiece component 446 allows for activation (e.g., acts as activation button 438) of vaporizer device 400. Additionally or alternatively, activation button 438 includes a biometric identification device (e.g., a fingerprint scanner) and/or another form of identification device to identify the user. In some non-limiting embodiments, a user is able to personalize vaporizer device 400 and/or prevent others from using vaporizer device 400. Such features may be helpful in situations where monitoring of vaporizer device 400 is not always available and/or may prevent another unauthorized user (e.g., a child) from using the device.

In some non-limiting embodiments, housing 402 is sized and/or configured to substantially house (e.g., enclose) the components of vaporizer device 400, to provide an external appearance to vaporizer device 400, and/or allow vaporizer device 400 to fit ergonomically in the hand of a user. In some non-limiting embodiments, housing 402 includes upper housing 402a and lower housing 402b. In some non-limiting embodiments, upper housing 402a and lower housing 402b is constructed with an aesthetically pleasing appearance (e.g., to mimic the appearance of a wood grain) and/or includes colors, patterns, indicia, and/or the like, as desired. In some non-limiting embodiments, upper housing 402a and lower housing 402b is replaceable to allow for a user to customize a particular appearance of vaporizer device 400.

In some non-limiting embodiments, housing 402 is constructed from any suitable material, such as wood, metal, fiberglass, plastic, and/or the like. In some non-limiting embodiments, mouthpiece component 446 is interchangeable. In some non-limiting embodiments, variants of mouthpiece component 446 are configured such that mouthpiece component 446 restricts airflow to reproduce the pulling sensation that is similar to the sensation users may prefer and/or be familiar with in respect to smoking cigarettes, cigars, pipes, and/or the like. In some non-limiting embodiments, activation button 438 includes one or more control buttons, sensors, or switches, e.g., to allow a user to interact with vaporizer device 400. In some non-limiting embodiments, an interaction of activation button 438 includes turning vaporizer device 400 on and off.

In some non-limiting embodiments, valve 442 is configured to control airflow and/or seal off the reservoir when vaporizer device 400 is not in use. In some non-limiting embodiments, valve 442 is be sized and/or configured to fit over an end of cartridge 418 that has an aperture. Additionally or alternatively, valve 442 has a configuration that allows for precise attachment to cartridge 418 and/or that is sized and/or configured to contact (e.g., rest on) an end of inductor element 406 to place cartridge 418 within inductor element 406. In some non-limiting embodiments, cartridge 418 is positioned entirely within inductor element 406 or only a portion of cartridge 418 is positioned within inductor element 406. In some non-limiting embodiments, valve 442 is electronically controlled and is configured to remain closed until activation of vaporizer device 400 by a user (e.g., by way of activation button 438). In some non-limiting embodiments, valve 442 is manually controlled based on a thread and/or ramp in the mouthpiece. For example, the thread and/or ramp provides a gap between valve 442 and a top of cartridge 418. In some non-limiting embodiments, valve 442 is constructed of any suitable material, such as plastic, rubber, fiberglass, metal, glass, and/or the like. In some non-limiting embodiments, valve 442 is constructed from a suitable grade of silicone rubber.

In some non-limiting embodiments, tube 444 is sized and/or configured to be placed over an end of valve 442 that is distal from cartridge 418. Additionally or alternatively, tube 444 is sized and/or configured to direct the vapor, which is generated by heating a vaporizable substance, out of mouthpiece component 446. In some non-limiting embodiments, tube 444 is a cylinder. In some non-limiting embodiments, tube 444 is formed of any suitable material including, but not limited to, glass. In some non-limiting embodiments, tube 444 is configured to adjust airflow into and/or out of vaporizer device 400 (e.g., in association with valve 442). In some non-limiting embodiments, tube 444 and/or valve 442 is configured to prevent leakage of a vaporizable substance from cartridge 418.

In some non-limiting embodiments, power source 410 is a device that includes one or more electrochemical cells that convert stored chemical energy into electrical energy. In some non-limiting embodiments, power source 410 is sized and/or configured appropriately for an application, such as the placement of power source 410 within vaporizer device 400. In some non-limiting embodiments, power source 410 is the same as or substantially similar to power source 130. In some non-limiting embodiments, power source 410 includes a battery. In some non-limiting embodiments, the battery is a primary battery, a secondary battery, a rechargeable battery, and/or the like. Additionally or alternatively, the battery includes an alkaline battery, a watch battery, a Lithium Ion battery, and/or the like. In some non-limiting embodiments, power (e.g., in the form of an electrical energy, such as an electrical current and/or a voltage) is provided to inductor element 406 from power source 410.

In some non-limiting embodiments, electronic control components 436 of vaporizer device 400 includes a circuit that includes an alternating electrical current generating device (e.g., a circuit configured to provide an alternating electrical current based on receiving a direct electrical current from power source 410), a control device (e.g., control device 110), and/or at least one sensor. Additionally or alternatively, the control device controls the power provided to inductor element 406, which may provide precise monitoring and/or control of the power provided to inductor element 406 on a time scale that is as low as a few milliseconds.

In some non-limiting embodiments, the control device is configured to receive information (e.g., from a sensor) and adjust a heating profile (e.g., a profile associated with an amplitude of a magnetic field produced by inductor element 406 that varies or does not vary over time) to be applied to a susceptor element by inductor element 406. In some non-limiting embodiments, the at least one sensor is able to detect and/or calculate information, such as airflow from or into vaporizer device 400, pressure at locations within vaporizer device 400 or of the vapor exiting vaporizer device 400, temperature of the components or locations near the components of vaporizer device 400, such as the temperature of the induction coil, and/or the like. In some non-limiting embodiments, such features may allow the control device to determine that the user of vaporizer device 400 is beginning to inhale and/or that a power level is increased to compensate for a tendency of the incoming air to cool susceptor element 140 (e.g., below its ideal temperature, operating temperature range, and/or the like). In some non-limiting embodiments, when an active inhalation is not in progress, the control device is able to then reduce the power, which may improve the life of power source 410.

In some non-limiting embodiments, a control device of electronic control components 436 is able to use information to calculate and/or implement a temperature profile (e.g., a profile associated with a temperature of a susceptor element that varies or that does not vary over time) for heating a vaporizable substance. Additionally or alternatively, the control device is configured to adjust a heating profile applied to susceptor element 140 by inductor element 406 based on the vaporizable substance. In some non-limiting embodiments, the control device is able to implement a predetermined heating profile applied to susceptor element 140 by inductor element 406 according to the vaporizable substance.

In some non-limiting embodiments, the control device may allow a user to modify the settings and/or the entire algorithm for providing heat to a vaporizable substance in order to obtain an improved experience (e.g., a preferred experience, an optimal experience, and/or the like). In some non-limiting embodiments, the configuration of all of the electronic components (e.g., electronic control components 436) are sufficiently energy efficient to allow vaporizer device 400 to be handheld and battery operated. Additionally or alternatively, the electronic components include a printed circuit board and, in some non-limiting embodiments, the control device includes a processor, such as a microprocessor, a microcontroller, and/or the like.

In some non-limiting embodiments, cartridge 418 includes an identifier that includes information associated with the contents of cartridge 418. In some non-limiting embodiments, the identifier includes a marking, a barcode, a label, and/or the like that provides information associated with a vaporizable substance and/or information associated with susceptor element within cartridge 418. In some non-limiting embodiments, the identifier is incorporated into cartridge 418. For example, the identifier is etched into cartridge 418.

In some non-limiting embodiments, electronic control components 436 are connected to inductor element 406 and/or programmed to read the identifier and determine the information associated with the contents of cartridge 418 so that the information associated with the contents of cartridge 418 is used (e.g., by electronic control components 436) to set parameters and cause inductor element 406 to apply a heating profile to the vaporizable substance according to the content information of cartridge 418.

Figure 5:
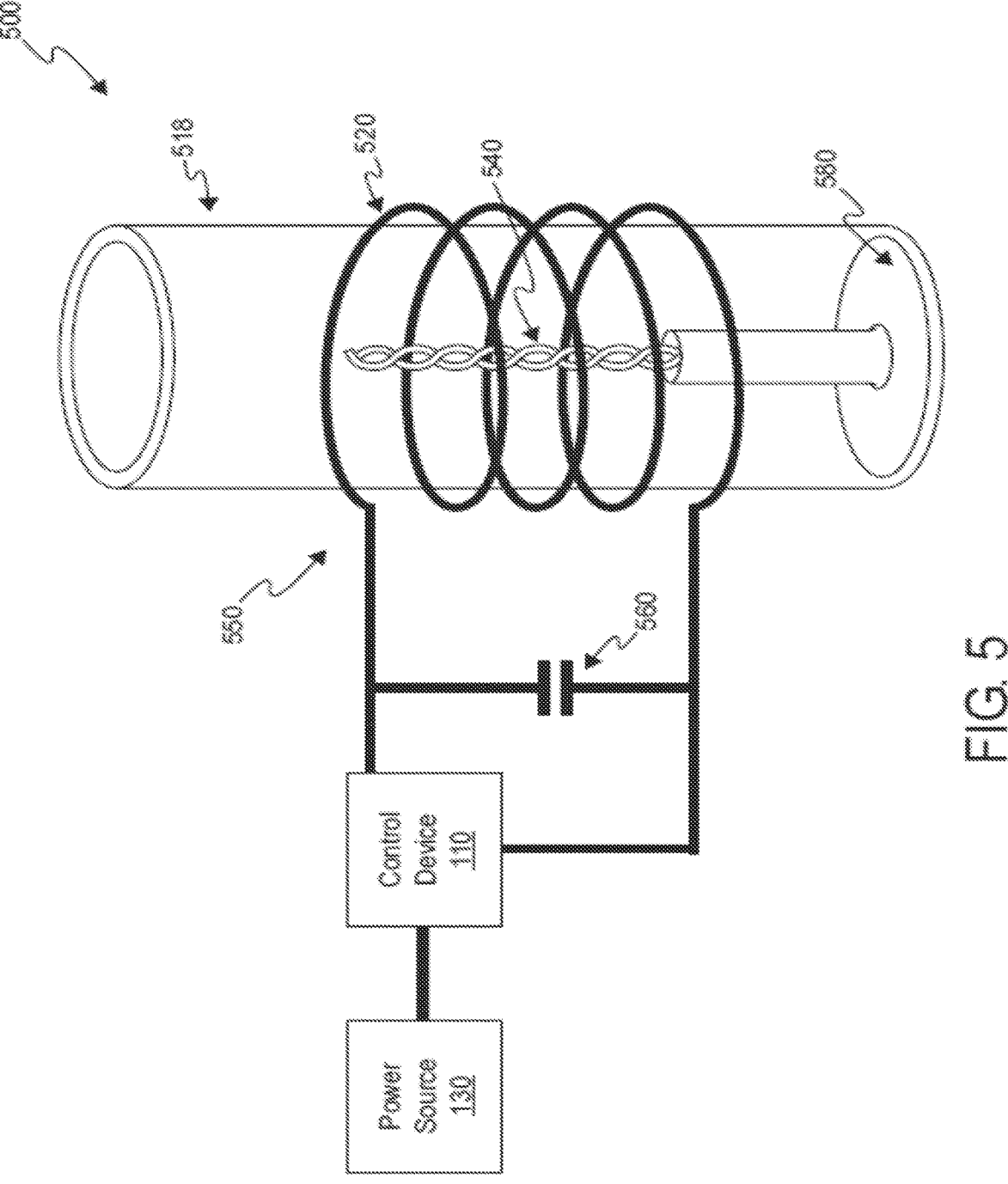
FIG. 5 is a diagram of a non-limiting embodiment of a system for determining a characteristic of an induction heating circuit.

Referring now to FIG. 5, FIG. 5 is a diagram of a non-limiting embodiment of induction heating system 500. As shown in FIG. 5, induction heating system 500 includes induction heating circuit 550, control device 110, power source 130, susceptor element 540, cartridge 518, and vaporizable substance 580. As further shown in FIG. 5, induction heating circuit 550 includes inductor 520 and capacitor 560. In some non-limiting embodiments, induction heating circuit 550 is the same as or substantially similar to induction heating circuit 150. In some non-limiting embodiments, capacitor 560 is the same as or substantially similar to capacitor element 160 and/or capacitor element 414. In some non-limiting embodiments, inductor 520 is the same as or substantially similar to inductor element 120 and/or inductor element 406. In some non-limiting embodiments, susceptor element 540 is the same as or substantially similar to susceptor element 140. In some non-limiting embodiments, cartridge 518 is the same as or substantially similar to cartridge 418.

In some non-limiting embodiments, control device 110 determines the SRF value of induction heating circuit 550 based on an input (e.g., an alternating electrical current having a frequency value) provided by control device 110 to induction heating circuit 550. In some non-limiting embodiments, the SRF value of induction heating circuit 550 is in a range between 100 kHz to 200 kHz based on a configuration of induction heating circuit 550 and susceptor element 540. In some non-limiting embodiments, control device 110 scans a plurality of frequency values in the range between frequency values based on the input provided to induction heating circuit 550. In some non-limiting embodiments, control device 110 measures a time delay between an excitation of induction heating circuit 550 based on the input provided by control device 110 to induction heating circuit 550 (e.g., an alternating electrical current provided as an input to inductor 520) and a response of induction heating circuit 550 to a magnetic property of susceptor element 540 (e.g., the SRF value of induction heating circuit 550) at each frequency value that is scanned. In some non-limiting embodiments, the excitation of induction heating circuit 550 and/or the response of induction heating circuit 550 to the magnetic property of susceptor element 540 is measured by control device 110 by measuring a voltage across capacitor 560.

Figure 6A:
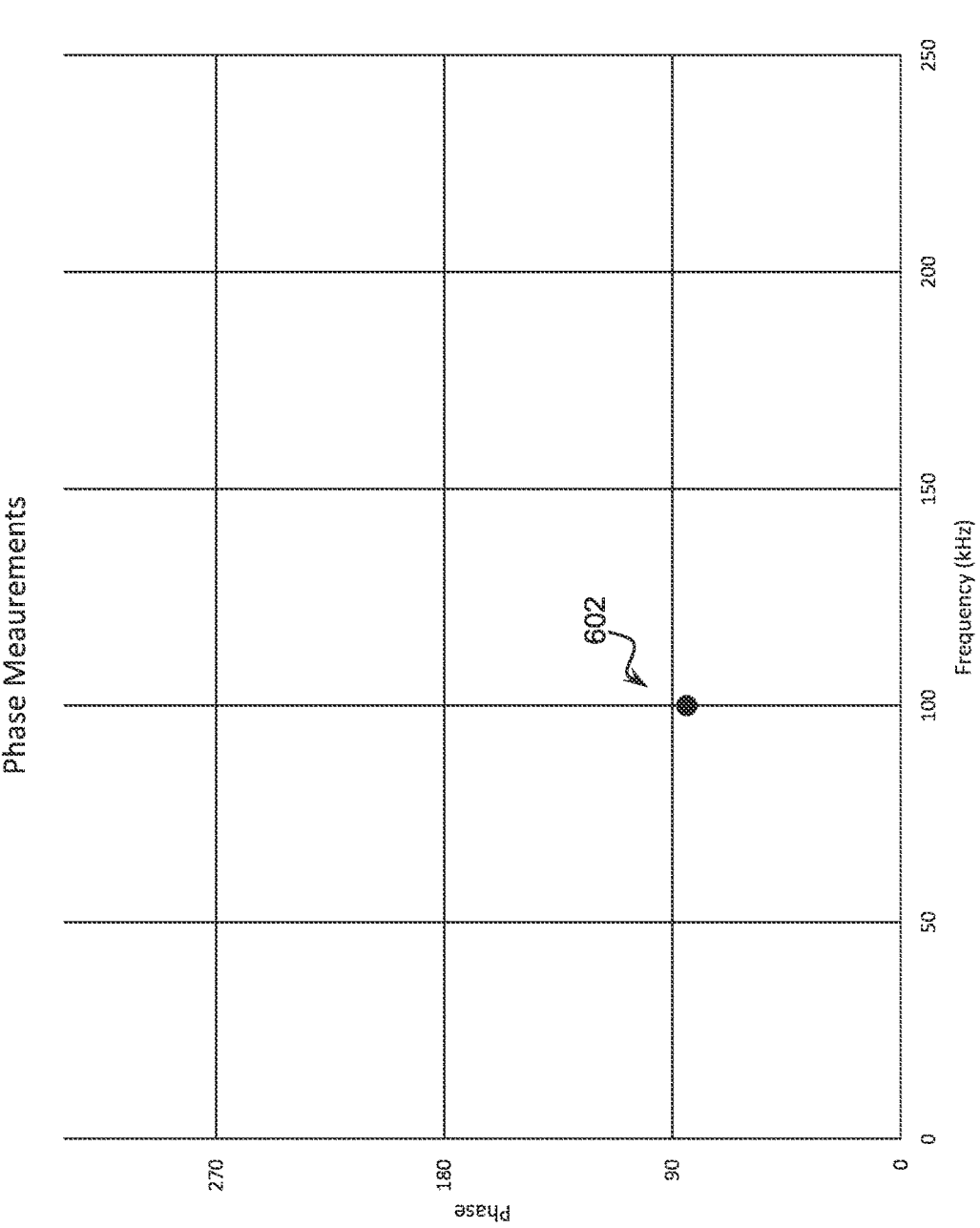
FIGS. 6A-6F are diagrams of a non-limiting embodiment of an implementation of a process for determining a response phase of an induction heating circuit.
Figure 6B:
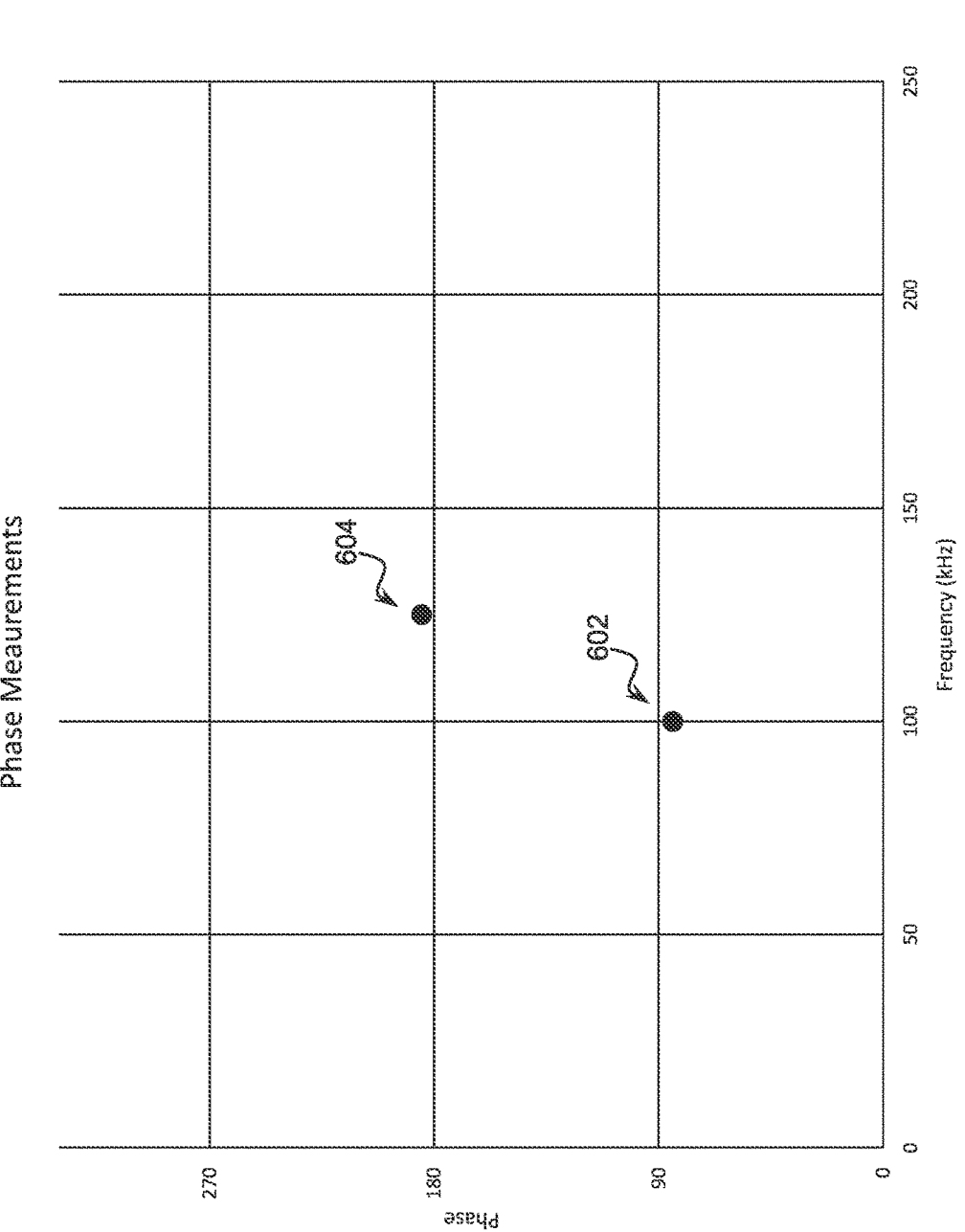

Referring now to FIGS. 6A-6F, FIGS. 6A-6F are diagrams of an implementation of a process for determining a response phase of an induction heating circuit based on a time delay between excitation of the induction heating circuit based on an input provided and a response of the induction heating circuit. As shown in FIG. 6A, data point 602 is a first phase value of a first AC voltage across capacitor 560 of induction heating circuit 550 based on a first driving AC voltage at a first driving frequency. In some non-limiting embodiments, control device 110 drives induction heating circuit 550 with the first driving AC voltage at the first driving frequency and measures data point 602 across capacitor 560 of induction heating circuit 550 based on the first driving AC voltage. As shown in FIG. 613, data point 604 is a second phase value of a second AC voltage across capacitor 560 of induction heating circuit 550 based on a second driving AC voltage at a second driving frequency. In some non-limiting embodiments, control device 110 drives induction heating circuit 550 with the second driving AC voltage at the second driving frequency and measures data point 604 across capacitor 560 of induction heating circuit 550 based on the second driving AC voltage.

Figure 6C:
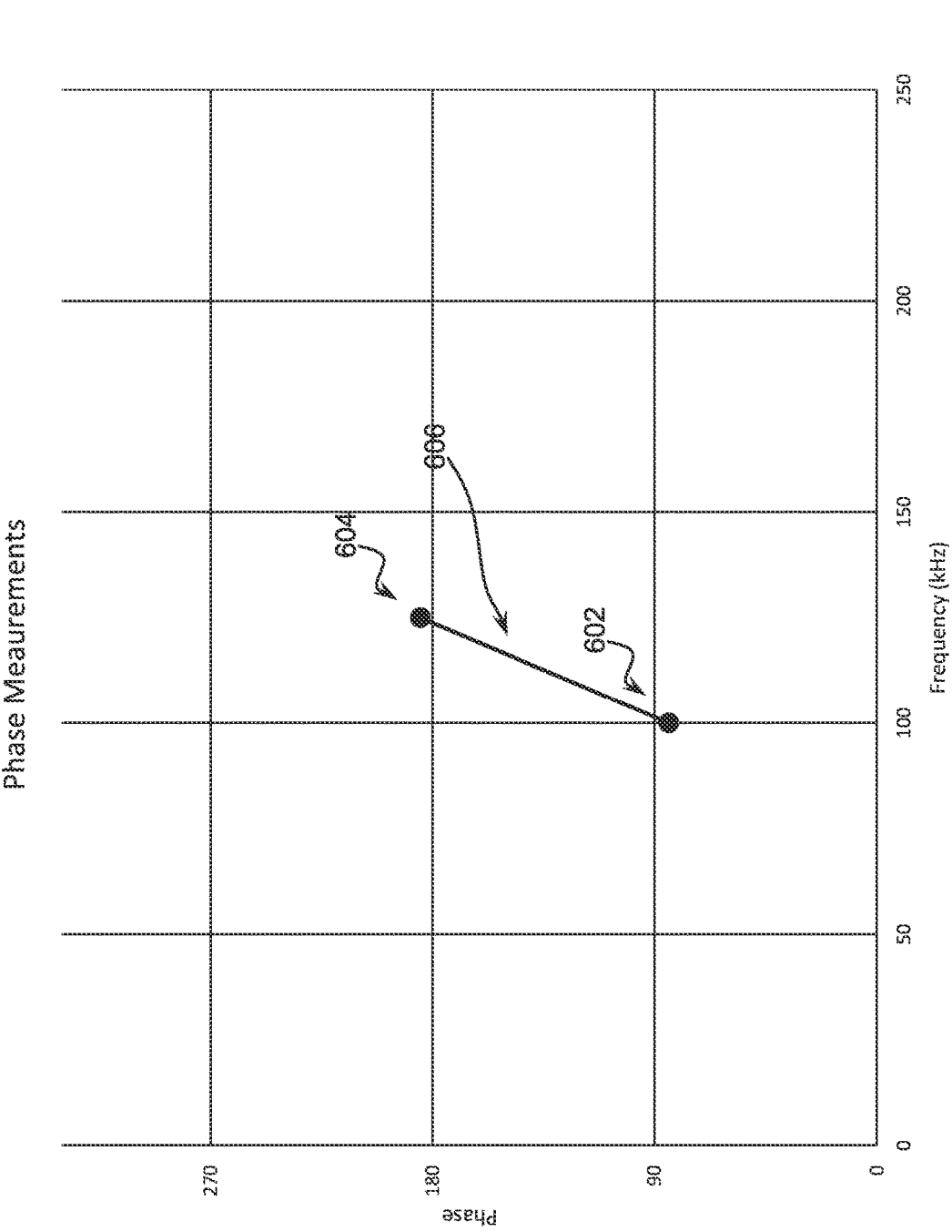
Figure 6D:
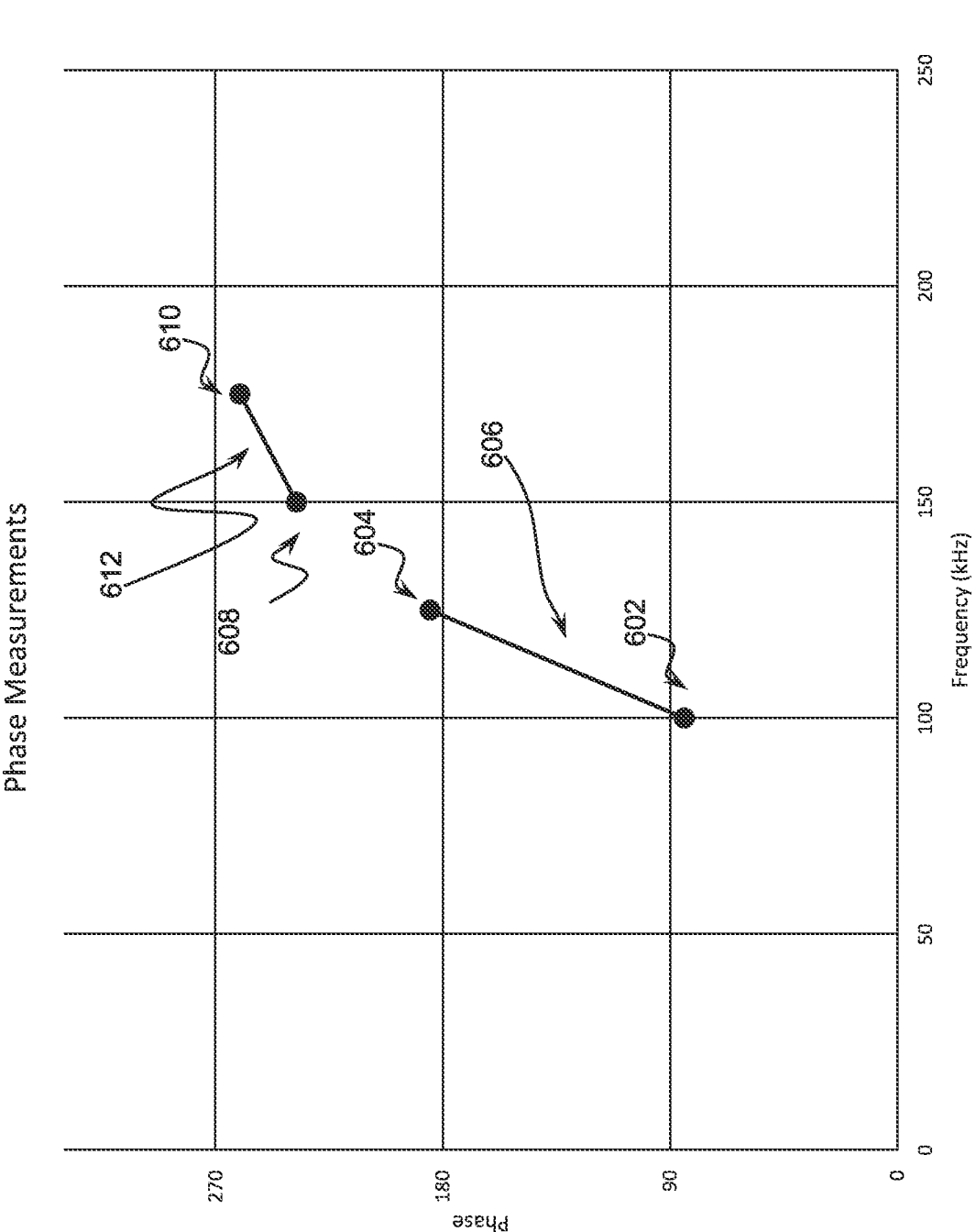
Figure 6E:
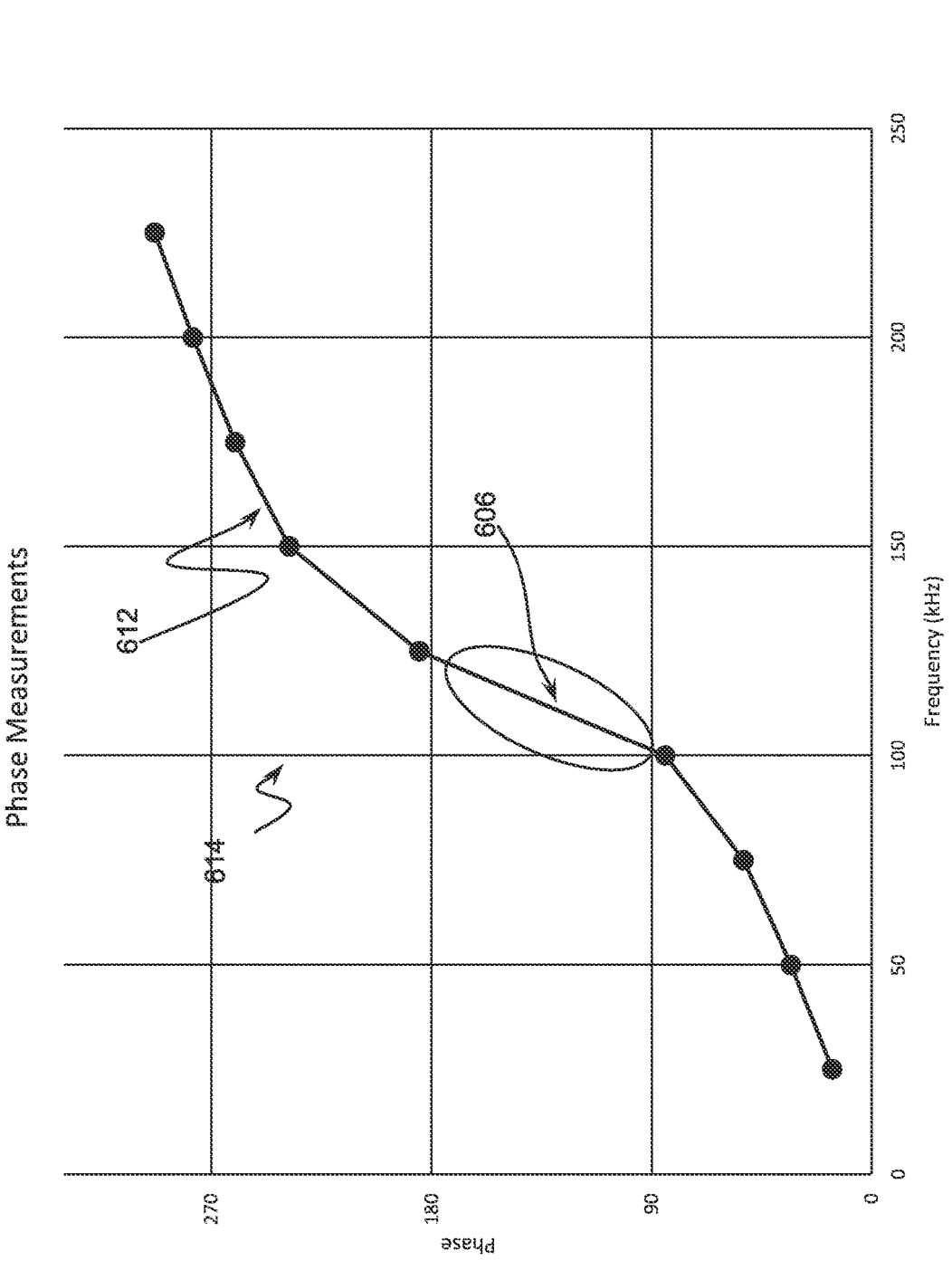

As shown in FIG. 6C, line 606 of phase versus frequency is based on data point 602 and data point 604. In some non-limiting embodiments, control device 110 generates line 606 based on the first phase value at the first driving frequency and the second phase value at the second driving frequency. As shown in FIG. 6D, additional data points 608 and 610 may be measured similar to data points 602 and 604. Additionally, line 612 may be generated similar to line 606.

As shown in FIG. 6D, a plurality of lines 614 may be generated similar to line 606 for each line of the plurality of lines 614. In some non-limiting embodiments, control device 110 determines a line of the plurality of lines 614 that has a maximum slope. As further shown in FIG. 6D, control device 110 determines that line 606 of the plurality of lines 614 that has the maximum slope. In some non-limiting embodiments, control device 110 determines an average frequency of line 606 having the maximum slope and determines a phase value corresponding to the average frequency of line 606 having the maximum slope. For example, control device 110 determines a first frequency value for data point 602 and a second frequency value for data point 604. In such an example, control device determines the average frequency of line 606 as the average frequency of the first frequency value and the second frequency value. Further, control device 110 determines a time delay that is equal to the difference of the phase value corresponding to the maximum slope and an assumed phase value at quadrature (e.g., 90 degrees) divided by a product of a full period of phase and the average frequency of the line having the maximum slope.

Figure 6F:
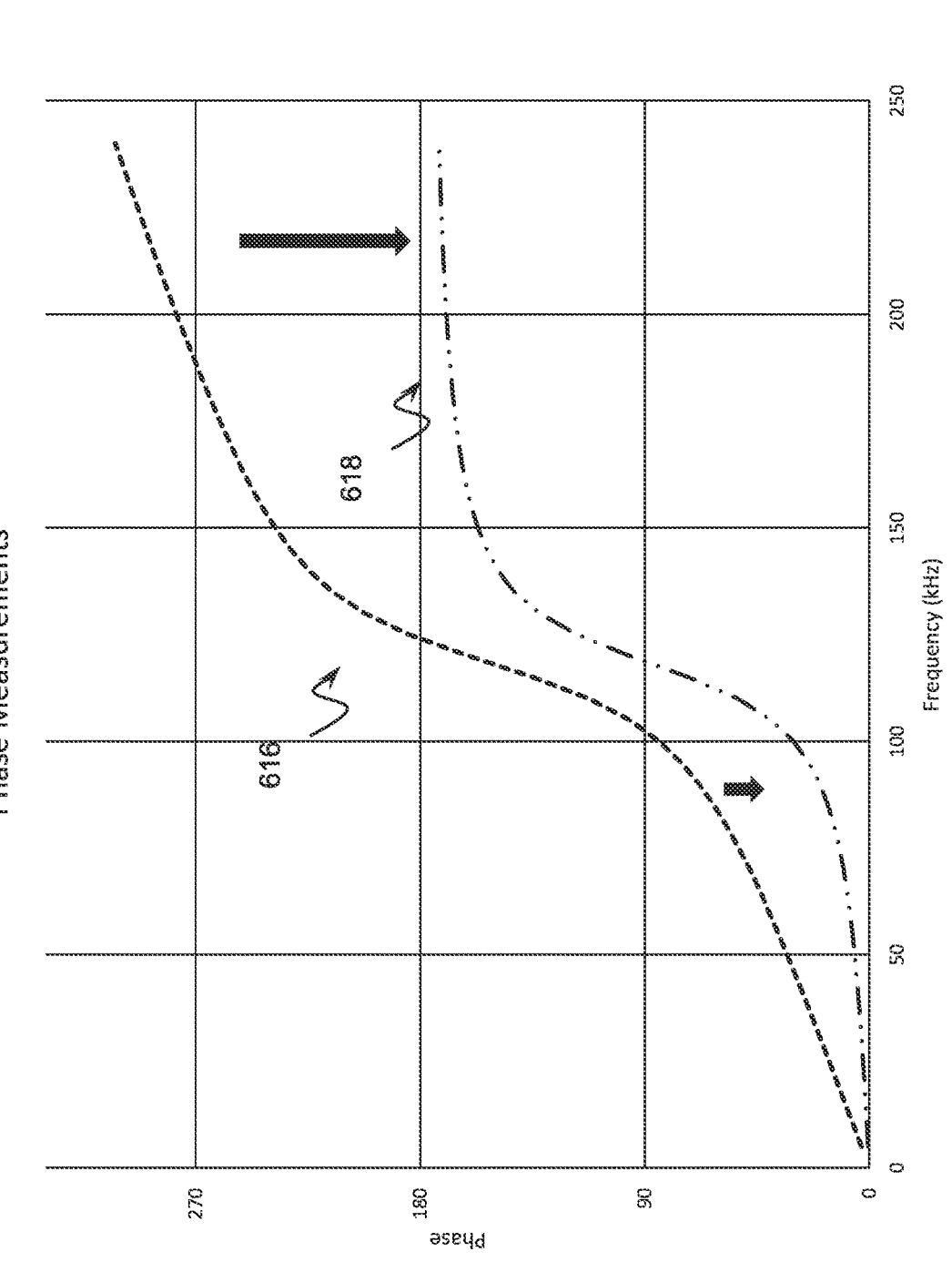

As shown in FIG. 6F, control device 110 may generate preliminary phase plot 616 of an AC voltage across capacitor 560 based on a driving AC voltage at a plurality of driving frequencies. As further shown in FIG. 6F, control device 110 may adjust preliminary phase plot 616 using the time delay to provide corrected preliminary phase plot 618 of the AC voltage across capacitor 560 based on the driving AC voltage at the plurality of driving frequencies. In some non-limiting embodiments, control device 110 may determine a plurality of response phases of induction heating circuit 550 at a plurality of driving frequencies based on corrected preliminary phase plot 618.

Figure 7:
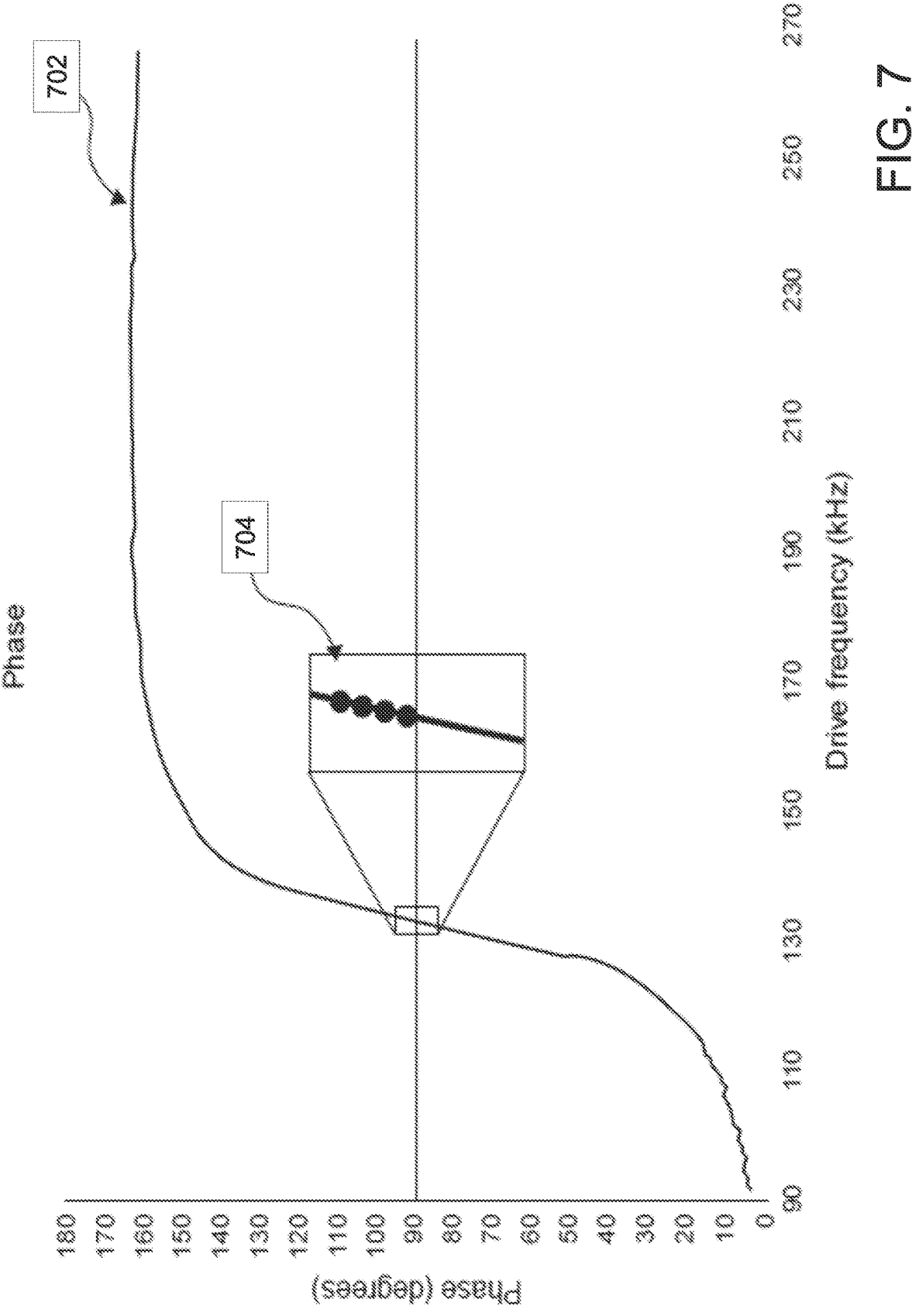
FIG. 7 is a non-limiting embodiment of a graph of phase values versus frequency that are used by a system for determining a characteristic of an induction heating circuit.

Referring now to FIG. 7, FIG. 7 is a non-limiting embodiment of a graph of phase values versus frequency that are used by a system for determining a characteristic of an induction heating circuit. As shown in FIG. 7, graph 702 includes values of phase for the difference in phase between an alternating electrical current provided as an input to induction heating circuit 550 (e.g., an alternating electrical current driving induction heating circuit 550) and a voltage (e.g., a voltage response) across capacitor 560 for frequency values associated with the alternating electrical current. In some non-limiting embodiments, the phase corresponds to a time delay between the excitation of induction heating circuit 550 based on the alternating electrical current provided by control device 110 as an input to induction heating circuit 550 (e.g., as an input to inductor 520 of induction heating circuit 550) and the response of induction heating circuit 550. The shape and position of this curve changes in response to the magnetic property of susceptor element 540 as measured based on a voltage across capacitor 560 in a range between 0 Hz to 300 kHz.

In some non-limiting embodiments, control device 110 determines the SRF value of induction heating circuit 550 based on the phase values of the voltage across capacitor 560 for the frequency values associated with the alternating electrical current that drives (e.g., that is provided as the input to) induction heating circuit 550. In some non-limiting embodiments, control device 110 determines a numerical derivative of the phase of the voltage across capacitor 560, where the phase is shown in graph 702. As shown in FIG. 7, graph 706 includes the numerical derivative of the phase versus frequency values shown in graph 702. Control device 110 determines a maximum value 707 of the numerical derivative (e.g., a frequency value for induction heating circuit 550 at which the phase is equal to 90 degrees) as an initial estimated value of the SRF value of induction heating circuit 550.

In some non-limiting embodiments, control device 110 determines the SRF value of induction heating circuit 550 based on an initial estimated value of the SRF value of induction heating circuit 550. For example, control device 110 determines the initial estimated value of the SRF value of induction heating circuit 550 as described above. In some non-limiting embodiments, a desired power level to be output by induction heating circuit 550 is set by control device 110 based on control device 110 controlling a voltage across capacitor 560. Once the desired power level is set, control device 110 continuously provides an alternating electrical current at a plurality of different frequency values as an input to induction heating circuit 550. In some non-limiting embodiments, the plurality of frequency values includes 4 frequency values that are within a predetermined amount of and above the initial estimated value of the SRF value, and that have a period that is an integer number of clock cycles of a clock of control device 110.

As further shown in FIG. 7, the initial estimated value of the SRF value is 145 kHz and control device 110 includes a 16 MHz clock, the plurality of frequency values 704 includes 4 frequency values that correspond to 110, 109, 108, and 107 periods of the 16 MHz clock: 145.45 kHz, 146.78 kHz, 148.15 kHz, and 149.53 kHz. At each frequency value of the plurality of frequency values, control device 110 measures a time delay between the excitation of induction heating circuit 550 and the response from susceptor element 540 and control device 110 may convert the time delay to measurement of phase in degrees. Control device 110 determines the SRF value of induction heating circuit 550 based on the time delay between the excitation of induction heating circuit 550 and the response from susceptor element 540.

In some non-limiting embodiments, as the temperature of susceptor element 540 changes, the magnetic properties of susceptor element 540, such as the magnetic susceptibility of susceptor element 540, change based on the temperature change of susceptor element 540 or vice versa. The change of the magnetic susceptibility of susceptor element 540 may cause a change in the inductance of inductor 520 that is near susceptor element 540. The change in the inductance of inductor 520 causes a change in the SRF value of induction heating circuit 550. In some non-limiting embodiments, control device 110 determines the temperature of susceptor element 540 based on the SRF value of induction heating circuit 550 and a measurement of amplitude of an electrical characteristic of induction heating circuit 550. In some non-limiting embodiments, the electrical characteristic of induction heating circuit 550 includes an electrical current provided to induction heating circuit 550 (e.g., an alternating electrical current provided to inductor 520 of induction heating circuit 550), a magnetic field produced by inductor 520, and/or a voltage across capacitor 560.

Figure 8:
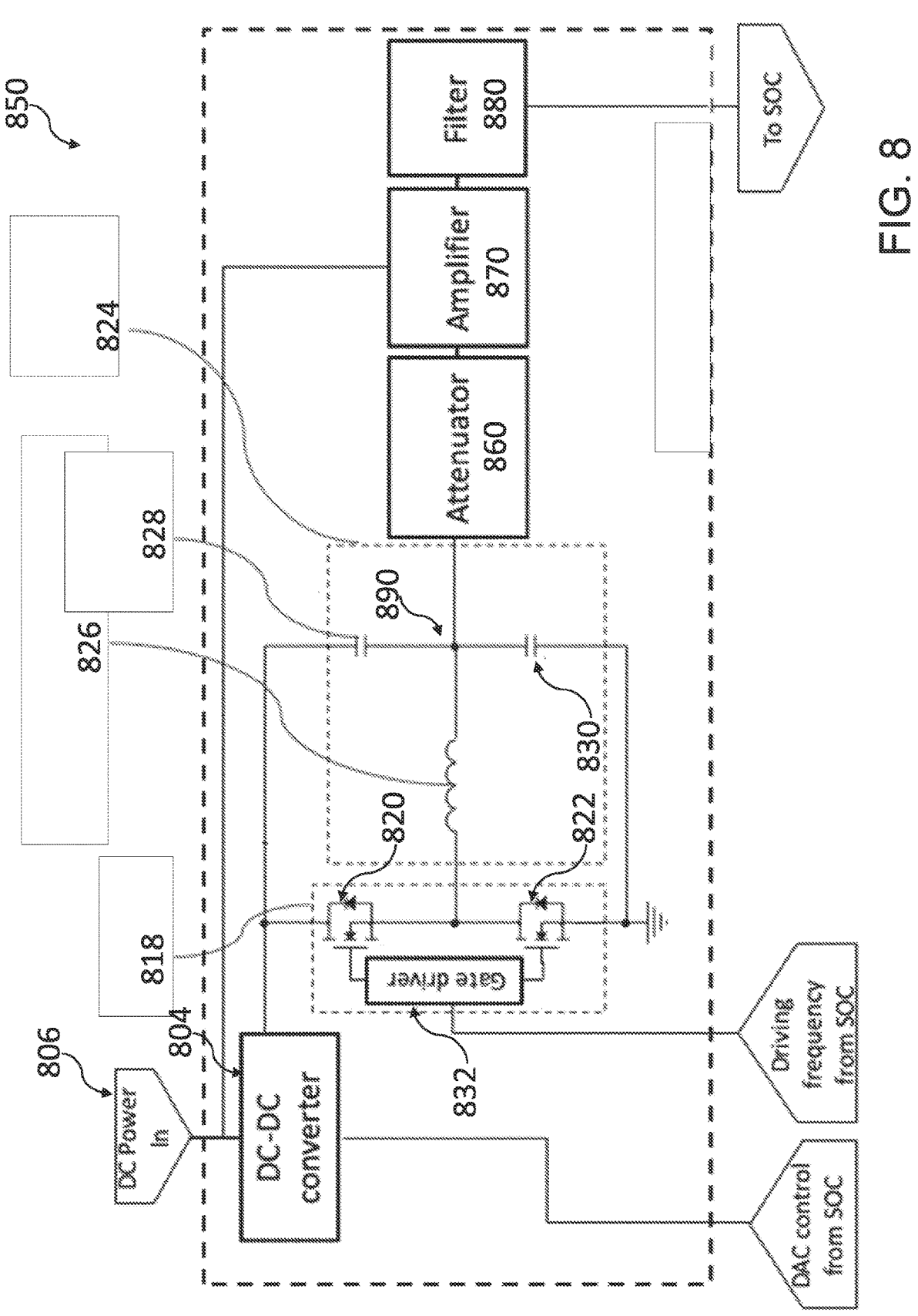
FIG. 8 is a diagram of a non-limiting embodiment of an induction heating circuit.

Referring now to FIG. 8, FIG. 8 is a diagram of induction heating circuit 850. In some non-limiting embodiments, induction heating circuit 850 is the same as or substantially similar to induction heating circuit 150 or induction heating circuit 550. In some non-limiting embodiments, half bridge 818 is configured to provide alternating electrical current to inductor-capacitor (LC) tank circuit 824. In some non-limiting embodiments, control device 110 detects a response of induction heating circuit 850 to a characteristic of a susceptor element, such as susceptor element 140. Examples of such a characteristic may be a change in a magnetic property or in the resistivity of the material of the susceptor element. Any characteristic that has an effect on the inductance of the inductor 826 may elicit a response that can be measured. In some non-limiting embodiments, a control device, such as control device 110, is electrically connected to induction heating circuit 850 to determine the self-resonant frequency (SRF) value of induction heating circuit 850 from the phase of an alternating electrical current provided to induction heating circuit 850 with sufficient accuracy to determine a temperature of susceptor element 140 (e.g., based on a configuration of susceptor element 140).

As further shown in FIG. 8, components of induction heating circuit 850, such as DC-DC converter 804 and half bridge 818 are configured to provide power to LC tank circuit 824. In some non-limiting embodiments, LC tank circuit 824 includes inductor 826, capacitor 828, and capacitor 830. In some non-limiting embodiments, inductor 826 is the same as or substantially similar to inductor element 120 and/or inductor 520. In some non-limiting embodiments, inductor 826 includes a 0.9 μH inductor. In some non-limiting embodiments, each of capacitor 828 and capacitor 830 is the same as or substantially similar to capacitor element 160. In some non-limiting embodiments, a combination of capacitor 828 and capacitor 830 is the same as or substantially similar to capacitor element 160. In some non-limiting embodiments, capacitor 828 and capacitor 830 each include a 680 nF capacitor. In some non-limiting embodiments, capacitor 828 and capacitor 830 are electrically connected in series or in parallel with the coil.

In some non-limiting embodiments, LC tank circuit 824 is configured with capacitor 828 and capacitor 830 electrically connected in series to ground with inductor 826 connected to a point between capacitor 828 and capacitor 830. In this way, capacitor 828 and capacitor 830 have half the voltage across each of capacitor 828 and capacitor 830 as compared to a situation where a single capacitor is used that has a capacitance equal to the capacitance of the sum of capacitor 828 and capacitor 830. Since the capacitance of a capacitor is related to voltage capacity, splitting the total capacitance requirement into a plurality of capacitors allows the use of capacitors that have smaller dimensions, providing a smaller form factor for a device that incorporates induction heating circuit 850 as compared to a device that incorporates a circuit that includes a single capacitor having larger dimensions.

As further shown in FIG. 8, induction heating circuit 850 includes DC-DC converter 804, half bridge 818, and LC tank circuit 824. In some non-limiting embodiments, DC-DC converter 804 is a buck converter, a boost converter, or a buck-boost converter. In some cases, the half bridge 818 includes field-effect transistor (FET) 820 and FET 822. In some non-limiting embodiments, FET 820 and/or FET 822 include a metal-oxide-semiconductor FET (MOSFET).

In some non-limiting embodiments, DC-DC converter 804 provides a variable voltage to adjust the power (e.g., electrical energy) in the LC tank circuit 824 and half bridge 818 excites LC tank circuit 824 at close to the SRF value of LC tank circuit 824 (e.g., the SRF value of induction heating circuit 850 that includes LC tank circuit 824).

In some non-limiting embodiments, half bridge 818 includes FET 820 and FET 822 driven in opposition at a 50% or about a 50% duty cycle. In some non-limiting embodiments, a gate driver 832 is used so that both FET 820 and FET 822 are never on at the same time, as well as maximizing FET efficiency. In some non-limiting embodiments, a gate driver and a control signal (e.g., a logic signal) to control the gate driver are provided by a control device (e.g., control device 110).

In some non-limiting embodiments, with the use of half bridge 818, power provided by a power source (e.g. power source 130) at electrical connection 806 is maximum at the SRF value, $f_0$, of LC tank circuit 824. The SRF value, $f_0$, can be calculated based on the equation:

$$2\pi f_0 = 1/\sqrt{L \cdot (C_1 + C_2)}$$

In some non-limiting embodiments, half bridge 818 is used to control power supplied to a susceptor element by varying an excitation frequency away from the SRF of the LC tank circuit 824 and, thereby, decreasing the amplitude of an alternating electromagnetic field produced by inductor 826. In some non-limiting embodiments, half bridge 818 maintains the frequency value of the alternating electrical current through LC tank circuit 824 close to the SRF value of LC tank circuit 824 for making measurements of a characteristic or property of a susceptor element. In some non-limiting embodiments, this characteristic may be the temperature of the susceptor. In some non-limiting embodiments, DC-DC converter 804 is used to control (e.g., regulate) the power provided to half bridge 818.

In some non-limiting embodiments, DC-DC converter 804 is a buck convertor that uses a fixed frequency value with varying duty cycle. In some non-limiting embodiments, the switching frequency of DC-DC converter 804 is set at a frequency value significantly higher than the SRF of the LC tank circuit 824. In some non-limiting embodiments, the switching frequency DC-DC converter 804 is in a range between 300 kHz to 10 MHz based on an SRF of LC tank circuit 824 of about 150 kHz.

In some non-limiting embodiments, FET 820 and FET 822 are driven through a gate driver 832 from a square wave having a frequency value and that is generated by a Pulse Width Modulation (PWM) circuit in a control device (e.g., control device 110). In some non-limiting embodiments, half bridge 818 uses a 50% duty cycle with a variable frequency value. In some non-limiting embodiments, duty cycles other than a 50% duty cycle produce a DC offset in the output waveform of half bridge 818 are provided to inductor 826. In some non-limiting embodiments, the control device controls (e.g., regulates) electrical energy (e.g., electrical current and/or voltage) provided to DC-DC converter 804 at electrical connection 806.

In some non-limiting embodiments, to control an alternating electrical current within induction heating circuit 850, a control device samples a voltage between the output of inductor 826 and ground (e.g., voltage is sampled across capacitor 830) to generate a voltage waveform and the voltage waveform is provided to the control device for adjustment of power (e.g., in the form of a magnetic field)

produced by inductor 826. In some non-limiting embodiments, the voltage waveform will provide a phase and amplitude of the voltage at the same frequency value of the drive frequency value of the alternating electrical current through inductor 826.

In some non-limiting embodiments, after correction of the phase based on time delays (e.g., time delays introduced by components of induction heating circuit 850), the phase is used to compute the SRF value of LC tank circuit 824 while the amplitude of the voltage is used to compute the amplitude of the alternating electrical current. In some cases, the SRF value of the LC tank circuit 824 is measured by determining the drive frequency value at which the amplitude of the alternating electrical current is at maximum. In some non-limiting embodiments, the SRF value of the LC tank circuit 824 is a function of both the magnitude of the magnetic field produced by inductor 826 and the temperature of a susceptor element. In some non-limiting embodiments, the amplitude of the alternating electrical current, which is proportional to the amplitude of the voltage across capacitor 830, and the SRF value of the LC tank circuit 824 are used to determine the temperature of susceptor element 140.

In some non-limiting embodiments, control device 110 is configured to detect a response of LC tank circuit 824 to a magnetic property of a susceptor element (e.g., susceptor element 140). As further shown in FIG. 8, induction heating circuit 850 includes attenuator 860, amplifier 870 and filter 880. In some non-limiting embodiments, filter 880 includes a 3-pole Bessel low pass filter (LPF).

In some embodiments, attenuator 860 receives, as an input, a time varying voltage across capacitor 830. In some non-limiting embodiments, attenuator 860 includes a plurality of resistors configured as a voltage divider such that the output of the attenuator 860 is a fixed fraction of the input voltage. This is desirable in embodiments where the voltage across the capacitor exceeds the maximum voltage that components downstream can withstand. In some embodiments, amplifier 870 provides a high impedance to an input signal of amplifier 870 and a low impedance to an output signal of amplifier 870. In some non-limiting embodiments, amplifier 870 includes an operational amplifier. In some non-limiting embodiments, the output voltage of amplifier 870 is configured to be proportional to the input voltage. In some embodiments, amplifier 870 has a gain that is variable such that the gain can be changed by a control device to improve a resolution of a digital signal provided by analog to digital convertor (ADC) 950 (show in FIG. 9) to the control device (The signal that would change the gain is not shown in FIG. 8). In some non-limiting embodiments, filter 880 receives a signal from amplifier 870 and filters out unwanted noise at frequencies higher than a specified frequency (e.g., the SRF value) while leaving the phase and amplitude of the signal unchanged.

In some non-limiting embodiments, an output of attenuator 860 is amplified and/or buffered through to filter 880. As further shown in FIG. 8, the output of filter 880 is provided to the controller, which may be a system on a chip (SOC) which is comprised of functional blocks one of which may be an ADC. In some non-limiting embodiments, the output of filter 880 is additionally buffered before providing the output to the SOC.

To determine the SRF value of the LC tank circuit 824, a phase difference between an excitation signal (e.g., an alternating electrical current) provided by alternately turning on FET 820 and FET 822 and the response of the LC tank circuit 824 to a property of a susceptor element (e.g., a magnetic field produced by a susceptor element) is determined by a control device (e.g., control device 110). At resonance, the phase difference is 90 degrees. In some cases, induction heating circuit 850 is used under control of a control device (e.g., control device 110) to determine the response of the LC tank circuit 824.

Figure 9:
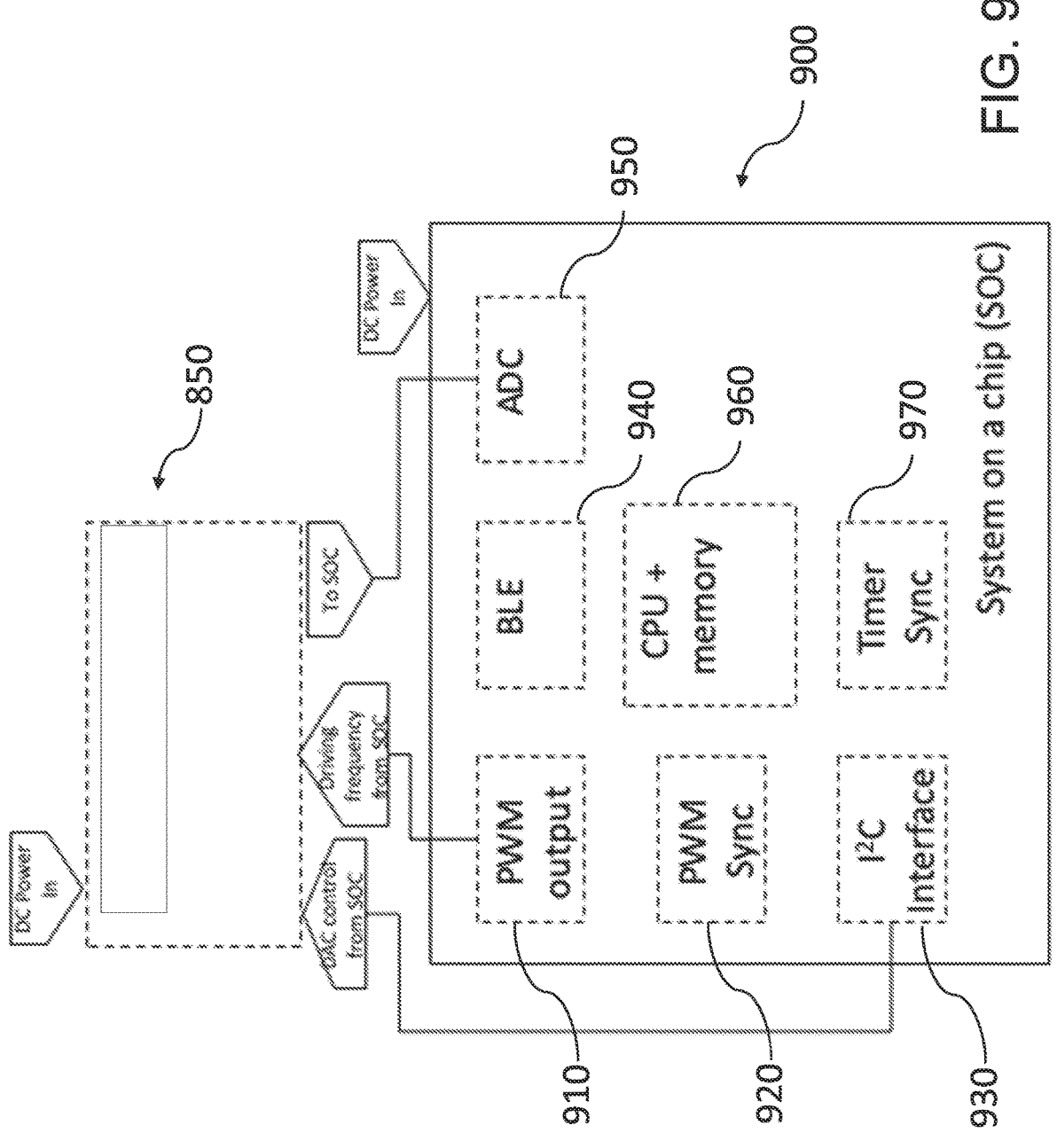
FIG. 9 is a diagram of a non-limiting embodiment of a system on a chip.

Referring now to FIG. 9, FIG. 9 is a diagram of system on a chip (SOC) 900. As shown in FIG. 9, SOC 900 includes functional blocks 910, 920, 930, 940, 950, 960, and 970. In some non-limiting embodiments, SOC 900 may be the same as or similar to control device 110. In some non-limiting embodiments, CPU+memory 960 executes computer code or firmware that controls all the other blocks and is configured to achieve the desired sequence of operations. In some non-limiting embodiments, PWM output 910 produces a square wave voltage signal whose frequency is configured by the execution of a CPU instruction. In some non-limiting embodiments, PWM sync 920 causes the phase of the PWM output 910 to be known relative to the computer clock so that the phase of the PWM output with respect to any other signal may be ascertained. In some non-limiting embodiments, I²C interface 930 is a serial interface standard often used to send digital instructions from one chip to another. In one example, I²C interface 930 is used for SOC 900 to send an instruction to control the output of DC-DC converter 804. In some non-limiting embodiments, Bluetooth Low Energy (BLE) interface 940 is a radio interface functional block that allows the firmware in CPU+memory 960 to send information to and from another BLE enabled device such as a smart phone or computer. This information may include updates to the firmware itself. In some non-limiting embodiments, a firmware update may be performed via Bluetooth using BLE interface 940. In some non-limiting embodiments, Timer Sync 970 is a functional block that together with PWM Sync 930 and ADC 950 allows accurate relative timing information to be available for the firmware algorithm to use. In some non-limiting embodiments, ADC 950 is an analog to digital converter which converts a continuous AC voltage input to a sequence of digital values. Not shown are other functional blocks that may be included as appropriate. Examples of other functional blocks include light emitting diode control and push button inputs.

As further shown FIG. 9, electrical signals are transmitted to and from SOC 900 and vice versa with regard to induction heating circuit 850 of FIG. 8. In some non-limiting embodiments, the electrical signals include the digital to analog converter (DAC) control, which is a control that determines the output voltage of DC-DC converter 704; the driving frequency, which is a square wave signal the frequency of which CPU+memory 960 is configured to calculate and output via PWM output 910; and the AC voltage from the measuring circuit consisting of attenuator 860, amplifier 870, and filter 880, which is converted to a digital value by ADC 950.

The firmware instructions stored in memory and executed by CPU+memory 960 are configured to use several algorithms. In some non-limiting embodiments, CPU+memory 960 uses a first algorithm to determine the time delay of the voltage signal caused by the voltage signal's progress from the measurement point 890 (as shown in FIG. 8) through attenuator 860, amplifier 870, filter 880 and ADC 950 until the digital value of that voltage is received by CPU+memory 960. This first algorithm consists of the following steps (e.g., which are executed by SOC 800): the resonant frequency is in a frequency range between 100 kHz to 200 kHz by design; when first turned on, SOC 800 scans the frequency range (e.g., scans based on 8 points) and a time delay between an excitation of induction heating circuit 850 and response of induction heating circuit 850 is measured by SOC 800 at each frequency that was scanned; a numerical derivative (e.g., a slope) of this data is then calculated by SOC 800; a maximum of the numerical derivative may be determined by SOC 800, the maximum of the numerical derivative provides an estimate of a self-resonant frequency (SRF) value; and SOC 800 may repeat a scan and calculate derivative method with progressively smaller frequency ranges until an adequately accurate estimate of the SRF value is obtained. In some non-limiting embodiments, the first algorithm takes less than a quarter of a second.

A second algorithm may be used to obtain a more accurate value of the time delay than a value of time delay calculated using the first algorithm and consists of the following steps (e.g., which are executed by SOC 800): Once there is an estimate of the SRF value, SOC 800 determines the time delay between the drive signal to the half bridge (e.g., half bridge 818) and the measured phase of the voltage across a capacitor (e.g., the voltage across capacitor 830 measured at point 890) of induction heating circuit 850; then SOC 800 determines an accurate measure of the phase difference between a phase of the driving signal and a phase of the voltage measured across the capacitor using an estimate of the time delay (e.g., an estimate of the time delay as provided by the first algorithm), the phase difference is measured at a plurality of frequencies (e.g., a series of 8 frequencies) around the estimate of the SRF value (e.g., the estimate of the SRF value from the first algorithm), for example within ±5 kHz of the estimate of the SRF value; SOC 800 determines a linear fit with a range of values of the time delay and the standard error of the linear fit is calculated and SOC 800 determines a value of the time delay that is the value of the time delay that gives the smallest standard error between the phase differences measured at the plurality of frequencies and the linear fit; SOC 800 may find the extrema (e.g., the minimum) of a plot of standard error versus values of time delay using an optimization method such as the golden-section search to quickly and efficiently find the minimum.

A third algorithm may be used to use the accurate value of the time delay from the algorithm above to follow the progression in time of the SRF and consists of the following steps (e.g., which are executed by SOC 800): The desired power level is set by SOC 800 by controlling the voltage provided to the half bridge (e.g., the voltage switched by the gates), and the voltage is controlled by SOC 800 by SOC 800 providing a control signal to a DC-DC converter; the desired power level is provided by the output of one of the control strategies outlined below; SOC 800 then cycles through 4 frequencies continuously, these frequencies are chosen as the 4 frequencies closest to, but above the SRF value that have a period that is an integral number of clock cycles of the microprocessor (e.g., with a tank resonant frequency of 145 kHz and a microprocessor with a 16 MHz clock, the 4 frequencies would correspond to 110, 109, 108 and 107 periods of the 16 MHz clock giving frequencies of 145.45 kHz, 146.78 kHz, 148.15 kHz and 149.53 kHz respectively) of SOC 800; at each frequency, the time delay between the driving square wave and the voltage response of the tank circuit is converted by SOC 800 to a phase and amplitude; the phase and amplitude at each frequency may be computed by SOC 800 with a windowed discrete Fourier transform (DFT) or set of windowed matched filters and then phase corrected for any duty cycle error, and the sampling is normally triggered off the edges of the square wave all samples will be 90 degrees out of phase; as resonance occurs at 90 degrees (e.g., phase quadrature) the 90 degree shift causes the resonance to occur at 0 degrees, allowing a contiguous linear fit around quadrature.

The SRF value is determined by extrapolating a linear fit to the measured values at quadrature (e.g., 90 degrees); as the temperature of the ferromagnetic susceptor changes, the susceptor's magnetic permeability changes and this in turn changes the inductance of the coil surrounding the susceptor, the change in inductance causes a change in the SRF value of the tank circuit; once the SRF value has been determined by SOC 800 as above, the 4 sampled frequencies that are cycled through are then changed so that the 4 sampled frequencies remain the closest to but higher than the SRF value, this allows the system to operate close to resonance while still being able to measure how that resonant frequency is changing.

Figure 10:
FIG. 10 is a non-limiting embodiment of a chart of SRF values versus susceptor temperatures that illustrates a method for converting SRF values to a susceptor temperature.

Referring now to FIG. 10, FIG. 10 is a chart of SRF values versus susceptor temperatures that illustrates a method for converting SRF values to a susceptor temperature. In some non-limiting embodiments, control device 110 determines a first SRF value at a low AC current through the induction heating coil and a high AC current through the induction heating coil. The difference between the first SRF value and the second SRF value is labeled as "SRF delta" in the chart of FIG. 10. In some non-limiting embodiments, control device 110 determines the temperature of a susceptor element on a time scale much less than a second, for example, such as two milliseconds. To obtain the data for the chart of FIG. 10, a thermocouple temperature sensor was placed in contact with a susceptor element. The thermocouple temperature sensor was chosen to be small with a heat capacity that is less than a heat capacity of the susceptor element. The SRF delta values are plotted in FIG. 10 against the contemporaneous readings from the thermocouple temperature sensor as the susceptor element is heated. In some non-limiting embodiments, control device 110 determines temperature of the susceptor element based on an equation (e.g., a linear equation, a quadratic equation, etc.) fitted to the data.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and the claims, the singular form of "a," "an," and "the" include plural referents unless the context clearly dictates otherwise.

What is claimed is:

1. An induction heating system, comprising:
   an induction heating circuit; and at least one processor programmed or configured to:
   generate data corresponding to phase value versus frequency of a signal with which the induction heating circuit is driven,
   determine a line from the data that has a maximum slope,
   determine an average frequency of the line from the data having the maximum slope,
   determine a phase value corresponding to the average frequency of the line from the data having the maximum slope,
   determine a time delay, wherein the time delay is equal to a difference of the phase value corresponding to the average frequency of the line from the data having the maximum slope and an assumed phase value at quadrature divided by a product of a full period of phase and the average frequency of the line from the data having the maximum slope,
   determine a self-resonant frequency (SRF) value of the induction heating circuit based on the time delay,
   determine a characteristic of the induction heating circuit based on the SRF value, and
   control a desired power level to be output by induction heating circuit based on the characteristic of the induction heating circuit, shut off a power output by induction heating circuit based on the characteristic of the induction heating circuit, and/or provide a warning indication based on the characteristic of the induction heating circuit.

2. The induction heating system according to claim 1, wherein when determining the SRF value of the induction heating circuit, the at least one processor is further programmed or further configured to:
   measure a preliminary first phase of a first alternating current (AC) voltage across an electrical component of the induction heating circuit based on a first driving AC voltage at a first driving frequency,
   adjust the preliminary first phase using the time delay to provide a corrected preliminary first phase,
   determine a first response phase of the induction heating circuit at the first driving frequency based on the corrected preliminary first phase, wherein the first response phase is a value of phase difference between a phase value of a driving current at the first driving frequency and a phase value of the first AC voltage across the electrical component of the induction heating circuit at the first driving frequency,
   measure a preliminary second phase of a second AC voltage across the electrical component of the induction heating circuit based on a second driving AC voltage at a second driving frequency,
   adjust the preliminary second phase using the time delay to provide a corrected preliminary second phase,
   determine a second response phase of the induction heating circuit at the second driving frequency based on the corrected preliminary second phase, wherein the second response phase is a value of phase difference between a phase value of a driving current at the second driving frequency and a phase value of the second AC voltage across the electrical component of the induction heating circuit at the second driving frequency,
   determine a function of phase versus frequency for the induction heating circuit based on the first response phase and the second response phase, and
   determine the SRF value where a phase value of the function of phase versus frequency is in quadrature.

3. The induction heating system according to claim 2, wherein the induction heating circuit comprises:

an inductor element, and a capacitor element.

4. The induction heating system according to claim 3, wherein the at least one processor is further programmed or further configured to determine a temperature of a susceptor element.

5. The induction heating system according to claim 4, wherein, when determining the temperature of the susceptor element, the at least one processor is programmed or configured to determine the temperature of the susceptor element based on a measurement of a magnetic field generated by the inductor element and a frequency value where the phase value of the function of phase versus frequency is in quadrature.

6. The induction heating system according to claim 4, wherein the at least one processor is further programmed or further configured to determine a measurement of a magnetic field generated by the inductor element, and wherein, when determining the temperature of the susceptor element, the at least one processor is programmed or configured to determine the temperature of the susceptor element based on the measurement of the magnetic field generated by the inductor element and the frequency value where the phase value of the function of phase versus frequency is in quadrature.

7. The induction heating system according to claim 4, wherein, when determining the temperature of the susceptor element, the at least one processor is further programmed or further configured to determine a measurement of a magnetic field generated by the inductor element based on a measurement of:

an amplitude of an A/C voltage across the capacitor element, and a frequency of the A/C voltage across the capacitor element, and wherein, when determining the temperature of the susceptor element, the at least one processor is further programmed or further configured to determine the temperature of the susceptor element based on the measurement of the magnetic field generated by the inductor element and the frequency value where the phase value of the function is in quadrature.

8. The induction heating system according to claim 4, wherein, when determining the temperature of the susceptor element, the at least one processor is programmed or configured to:

determine an amplitude of an A/C voltage across the capacitor element and a frequency of the A/C voltage across the capacitor element, determine a measurement of a magnetic field generated by the inductor element based on the amplitude of an A/C voltage across the capacitor element and the frequency of the A/C voltage across the capacitor element, and determine the temperature of the susceptor element based on the measurement of the magnetic field generated by the inductor element and the frequency value where the phase value of the function is in quadrature.

9. The induction heating system according to claim 4, further comprising at least one temperature sensor, wherein, when determining the temperature of the susceptor element, the at least one processor is programmed or configured to determine the temperature of the susceptor element based on a frequency value where the phase value of the function of phase versus frequency is in quadrature and an output of the at least one temperature sensor.

10. The induction heating system according to claim 4, further comprising at least one temperature sensor in thermal contact with at least one of the inductor element, the capacitor element, or any combination thereof, wherein, when determining the temperature of the susceptor element, the at least one processor is further programmed or further configured to determine the temperature of the susceptor element based on the frequency value where the phase value of the function is in quadrature and an output of the at least one temperature sensor.

11. The induction heating system according to claim 4, wherein the at least one processor is further programmed or further configured to control the temperature of the susceptor element.

12. The induction heating system according to claim 3, wherein the at least one processor is further programmed or further configured to determine a temperature of a susceptor element, and wherein, when determining the temperature of the susceptor element, the at least one processor is further programmed or further configured to determine the temperature of the susceptor element based on an amount of power absorbed by the susceptor element.

13. The induction heating system according to claim 2, wherein the induction heating circuit comprises an electrical component, and wherein the electrical component of the induction heating circuit comprises:

an inductor element, a capacitor element, or a component of the induction heating circuit that provides a phase that is the same as the phase of a voltage across the inductor element or the capacitor element.

14. The induction heating system according to claim 2, wherein the at least one processor is further programmed or further configured to:

measure a preliminary third phase of a third AC voltage across the electrical component of the induction heating circuit based on a fourth driving AC voltage at a third driving frequency, adjust the preliminary third phase using the time delay to provide a corrected preliminary third phase, determine a third response phase of the induction heating circuit at the third driving frequency based on the corrected preliminary third phase, wherein the third response phase is a value of phase difference between a phase of a driving current at the third driving frequency and a phase of a voltage across the electrical component of the induction heating circuit at the third driving frequency, measure a preliminary fourth phase of a fourth AC voltage across the electrical component of the induction heating circuit based on a fourth driving AC voltage at a fourth driving frequency, adjust the preliminary fourth phase using the time delay to provide a corrected preliminary fourth phase, determine a fourth response phase of the induction heating circuit, wherein the fourth response phase is a value of phase difference between a phase of a driving current at the fourth driving frequency and a phase of a voltage across the electrical component of the induction heating circuit at the fourth driving frequency, and wherein, when determining the function of phase versus frequency for the induction heating circuit, the at least one processor is further programmed or further configured to determine the function of phase versus frequency for the induction heating circuit based on the first response phase, the second response phase, the third response phase, and the fourth response phase.

15. The induction heating system according to claim 14, wherein the function of phase versus frequency comprises a polynomial, and wherein, when determining the function of phase versus frequency, the at least one processor is further programmed or further configured to determine polynomial coefficients of the polynomial that is fit to the first response phase of the induction heating circuit, the second response phase of the induction heating circuit, the third response phase of the induction heating circuit, and the fourth response phase of the induction heating circuit, and wherein, when determining the frequency value where the response phase value of the function is in quadrature, the at least one processor is further programmed or further configured to determine a frequency value where the phase value of the function of phase versus frequency is in quadrature based on the polynomial coefficients of the polynomial.

16. The induction heating system according to claim 2, wherein, when determining the function of phase versus frequency based on the first response phase and the second response phase, the at least one processor is further programmed or further configured to determine polynomial coefficients of a polynomial that is fit to the first response phase of the induction heating circuit and the second response phase of the induction heating circuit, and wherein, when determining the frequency value where the response phase value of the function is in quadrature, the at least one processor is further programmed or further configured to determine the frequency value where the phase value of the function of phase versus frequency is in quadrature based on the polynomial coefficients of the polynomial.

17. The induction heating system according to claim 1, wherein when generating the data, the at least one processor is further programmed or further configured to:

determine a first phase value of a first alternating current (AC) voltage across an electrical component of the induction heating circuit, wherein when determining the first phase of the first AC voltage across the electrical component of the induction heating circuit, the at least one processor is further programmed or further configured to:

drive the induction heating circuit with a first driving AC voltage at a first driving frequency, and measure the first phase value of the first AC voltage across the electrical component of the induction heating circuit based on the first driving AC voltage at the first driving frequency, determine a second phase value of a second AC voltage across the electrical component of the induction heating circuit, wherein when determining the second phase value of the second AC voltage across the electrical component of the induction heating circuit, the at least one processor is further programmed or further programmed or configured to:

drive the induction heating circuit with a second driving AC voltage at a second driving frequency, and measure the second phase value of the second AC voltage across the electrical component of the induction heating circuit based on the second driving AC voltage at the second driving frequency, and generate a line from the data of phase versus frequency based on the first phase value at the first driving frequency and the second phase value at the second driving frequency.

18. The induction heating system according to claim 17, wherein when determining the line from the data that has the maximum slope, the at least one processor is further programmed or further configured to:

determine a slope of each line of a plurality of lines from the data, wherein when determining the slope of each line of the plurality of lines from the data, the at least one processor is further programmed or further configured to determine the slope of the line from the data based on a difference of the first phase value and the second phase value divided by a difference of the first driving frequency and the second driving frequency, and compare the slope of each line of the plurality of lines from the data to a slope of all other lines of the plurality of lines from the data to provide the line from the data having the maximum slope.

19. The induction heating system according to claim 17, wherein the at least one processor is further programmed or further configured to:

determine the first phase value of the voltage across the electrical component of the induction heating circuit at the first driving frequency based on a first measurement of voltage across a capacitor element of the induction heating circuit, and determine the second phase value of the voltage across the electrical component of the induction heating circuit at the second driving frequency based on a second measurement of voltage across the capacitor element.

20. The induction heating system according to claim 1, wherein the at least one processor is further programmed or further configured to determine a temperature of a susceptor element, and wherein, when determining the temperature of the susceptor element, the at least one processor is further programmed or further configured to determine the temperature of the susceptor element based on the frequency value where the phase value of the function is in quadrature and a temperature of an inductor element, a capacitor element, or any combination thereof.

\* \* \* \* \*